(12) United States Patent
Armstrong et al.

(10) Patent No.: US 11,166,936 B2
(45) Date of Patent: *Nov. 9, 2021

(54) PHARMACEUTICAL COMPOSITIONS AND METHODS FOR COUNTERING CHEMOTHERAPY INDUCED CARDIOTOXICITY

(71) Applicants: Auransa Inc., Palo Alto, CA (US); SCT II LLC, Naperville, IL (US)

(72) Inventors: Christopher G. Armstrong, Madison, WI (US); Kevin J. Kim, Menlo Park, CA (US); Lisa Maria Lucia Pham, San Mateo, CA (US); Eunhye Park, Oakland, CA (US); Zhong Zhong, Hingham, MA (US); Guanyi Huang, Fremont, CA (US); Joseph C. Wu, Palo Alto, CA (US); Sidney Paul Elmer, Palo Alto, CA (US); Viwat Visuthikraisee, Palo Alto, CA (US); Eithon Michael G. Cadag, Seattle, WA (US); Thomas Bernard Freeman, San Bruno, CA (US); Pek Yee Lum, Palo Alto, CA (US)

(73) Assignees: Auransa Inc., Palo Alto, CA (US); SCT II LLC, Naperville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/064,576

(22) Filed: Oct. 6, 2020

(65) Prior Publication Data
US 2021/0121436 A1   Apr. 29, 2021

Related U.S. Application Data

(63) Continuation of application No. 16/737,849, filed on Jan. 8, 2020, now Pat. No. 10,874,633, which is a (Continued)

(51) Int. Cl.
| | |
|---|---|
| *A61K 31/352* | (2006.01) |
| *A61K 31/136* | (2006.01) |
| *A61K 31/353* | (2006.01) |
| *A61K 31/4545* | (2006.01) |
| *A61K 31/4439* | (2006.01) |
| *A61K 31/47* | (2006.01) |

(Continued)

(52) U.S. Cl.
CPC .......... *A61K 31/352* (2013.01); *A61K 9/0019* (2013.01); *A61K 9/0053* (2013.01); *A61K 9/127* (2013.01); *A61K 9/20* (2013.01); *A61K 9/48* (2013.01); *A61K 31/136* (2013.01); *A61K 31/353* (2013.01); *A61K 31/4439* (2013.01); *A61K 31/4545* (2013.01); *A61K 31/47* (2013.01); *A61K 31/496* (2013.01); *A61K 31/506* (2013.01); *A61K 31/517* (2013.01); *A61K 31/704* (2013.01); *A61K 31/7048* (2013.01); *A61K 38/005* (2013.01); *A61K 38/05* (2013.01); *A61K 45/06* (2013.01); *A61P 35/00* (2018.01); *A61K 31/404* (2013.01); *A61K 31/44* (2013.01); *A61P 9/00* (2018.01)

(58) Field of Classification Search
CPC .. A61K 31/352; A61K 31/136; A61K 31/353; A61K 31/4545; A61K 31/4439; A61K 31/47; A61K 31/496; A61K 31/406; A61K 31/517; A61K 31/704; A61K 31/7048; A61K 9/0019; A61K 9/127; A61K 9/20; A61K 9/48; A61K 38/05; A61K 38/005; A61K 45/06
See application file for complete search history.

(56) References Cited

U.S. PATENT DOCUMENTS

| 10,806,716 B2 | 10/2020 | Armstrong et al. |
| 10,874,633 B2 | 12/2020 | Armstrong et al. |

(Continued)

FOREIGN PATENT DOCUMENTS

| CN | 101485655 A | 7/2009 |
| CN | 102697795 A | 10/2012 |

(Continued)

OTHER PUBLICATIONS

Bandele, O.J. et al. (Jun. 2008, e-pub May 8, 2008). "Dietary Polyphenols As Topoisomerase II Poisons: B Ring And C Ring Substituents Determine The Mechanism Of Enzyme-Mediated DNA Cleavage Enhancement," Chemical Research In Toxicology 21(6):1253-1260.

(Continued)

*Primary Examiner* — Timothy R Rozof
(74) *Attorney, Agent, or Firm* — Morrison & Foerster LLP

(57) ABSTRACT

This disclosure provides methods and pharmaceutical compositions for reducing or eliminating cardiotoxicity, particularly cardiotoxicity induced by a cancer treatment or other therapy. In some cases, the methods and compositions prevent or reduce cardiotoxicity caused by anthracycline treatment. The methods provided herein often comprise administering a protective agent such as myricetin, tricetin, robinetin, ficetin, vitexin, quercetin, dihydrorobinetin, kaempferol, 7,3',4',5'-tetrahydroxyflavone, and myricitrin in conjunction with the administration of a cancer drug or other treatment. They may comprise administering a protective agent in combination with dexrazoxane. The compositions provided herein include co-formulations of a protective agent with a different protective agent or with a cancer treatment (e.g., anthracycline drug).

19 Claims, 29 Drawing Sheets

Related U.S. Application Data continuation of application No. 16/075,569, filed as application No. PCT/US2017/016582 on Feb. 3, 2017, now Pat. No. 10,806,716.

(60) Provisional application No. 62/348,102, filed on Jun. 9, 2016, provisional application No. 62/291,480, filed on Feb. 4, 2016.

(51) Int. Cl.

| | | |
|---|---|---|
| A61K 31/496 | (2006.01) | |
| A61K 31/506 | (2006.01) | |
| A61K 31/517 | (2006.01) | |
| A61K 31/704 | (2006.01) | |
| A61K 31/7048 | (2006.01) | |
| A61K 9/127 | (2006.01) | |
| A61K 9/20 | (2006.01) | |
| A61K 9/48 | (2006.01) | |
| A61K 38/05 | (2006.01) | |
| A61K 45/06 | (2006.01) | |
| A61K 9/00 | (2006.01) | |
| A61P 35/00 | (2006.01) | |
| A61K 38/00 | (2006.01) | |
| A61P 9/00 | (2006.01) | |
| A61K 31/404 | (2006.01) | |
| A61K 31/44 | (2006.01) | |

(56) References Cited

U.S. PATENT DOCUMENTS

| | | |
|---|---|---|
| 2002/0147353 A1 | 10/2002 | Vijgh et al. |
| 2004/0018987 A1 | 1/2004 | Hoffman et al. |
| 2009/0274746 A1 | 11/2009 | Gupta et al. |
| 2009/0281047 A1 | 11/2009 | Brown |
| 2013/0095124 A1 | 4/2013 | Szathmany et al. |
| 2015/0018294 A1 | 1/2015 | DeBenedetti et al. |
| 2017/0224654 A1 | 8/2017 | Armstrong et al. |
| 2019/0175544 A1 | 6/2019 | Armstrong et al. |
| 2020/0253920 A1 | 8/2020 | Armstrong et al. |

FOREIGN PATENT DOCUMENTS

| | | |
|---|---|---|
| CN | 103315993 A | 9/2013 |
| CN | 107595802 A | 1/2018 |
| KR | 20150084535 A | 7/2015 |
| WO | WO-2001/021608 A2 | 3/2001 |
| WO | WO-2001/021608 A3 | 3/2001 |
| WO | WO-2001/080855 A1 | 11/2001 |
| WO | WO-2014/077409 A1 | 5/2014 |
| WO | WO-2015/138186 A2 | 9/2015 |
| WO | WO-2017/136774 A1 | 8/2017 |

OTHER PUBLICATIONS

Bozza, W.P. et al. (2021). "Anthracycline-Induced Cardiotoxicity: Molecular Insights Obtained from Human-Induced Pluripotent Stem Cell-Derived Cardiomyocytes (hiPSC-CMs)," The AAPS journal 23(2): 1-12.
Crawford, L.J. et al. (2011). "Proteasome Inhibitors In Cancer Therapy," Journal Of Cell Communication And Signaling 5(2):101-110.
Dang, Y. et al. (2014). "Quantitative Determination Of Myricetin In Rat Plasma By Ultra Performance Liquid Chromatography Tandem Mass Spectrometry And Its Absolute Bioavailability," Drug Research 64(10):516-522.
European Medicines Agency Science Medicines Health (Mar. 5, 2007). "Nexavar: EPAR—Scientific Discussion," European Medicines Agency, 49 pages, as retrieved from https://www.ema.europa.eu/en/medicines/human/EPAR/nexavar.
European Medicines Agency Science Medicines Health (Mar. 5, 2007). "Nexavar: EPAR—Scientific Discussion," European Medi.
Jin, Y. et al. (2020). "A Comprehensive Review Of Clinical Cardiotoxicity Incidence Of FDA-Approved Small-Molecule Kinase Inhibitors," Frontiers in Pharmacology 11, 16 pages.
Kim, A. et al. (Apr. 2012, e-pub Jul. 17, 2019). "The Plasma And Cerebrospinal Fluid Pharmacokinetics Of Sorafenib After Intravenous Administration In Non-Human Primates," Investigational New Drugs 30(2):524-528.
Maillet, A. et al. (May 4, 2016). "Modeling Doxorubicin-Induced Cardiotoxicity in Human Pluripotent Stem Cell Derived-Cardiomyocytes," Sci Rep. 6:25333.
Russu, W.A. (Oct. 28, 2015). "Kinase Inhibitors—Targeted Personalized Cancer Therapy," Updates on Cancer Treatment, 20 pages.
Sawyer, D.B. (Mar. 21, 2013). "Anthracyclines And Heart Failure," New England Journal of Medicine 368(12):1154-1156.
Adams, M.J. et al. (Jun. 15, 2005). "Pathophysiology Of Anthracycline-And Radiation-Associated Cardiomyopathies: Implications For Screening And Prevention," Pediatr Blood Cancer 44(7):600-606.
American Cancer Society. (2014). "Cancer Treatment and Survivorship: Facts & Figures: 2014-2015," Publication, 48 pages.
Angsutararux, P. et al. (e-pub Sep. 29, 2015). "Chemotherapy-Induced Cardiotoxicity: Overview of the Roles of Oxidative Stress," Oxid Med Cell Longev. 2015:795602, 13 pages.
Bandele, O.J. et al. (May 22, 2007, e-pub. Apr. 26, 2007). "Bioflavonoids as Poisons of Human Topoisomerase IIa and IIB," Biochemistry 46(20):6097-6108.
Bast, A. et al. (May 26, 2007). "Protection By Flavonoids Against Anthracycline Cardiotoxicity: From Chemistry To Clinical Trials," Cardiovasc Toxicol. 7(2):154-159.
Batra, P. et al. (2013, e-pub. Feb. 12, 2013). "Anti-Cancer Potential Of Flavonoids Recent Trends And Future Perspectives," Biotech 3(6):439-459.
Cantero, G. et al. (2006, e-pub. Sep. 1, 2006). "Topoisomerase II Inhibition and High Meld of Endoreduplication Induced by the Flavonoids Luteolin and Quercetin," Mutagenesis 21(5):321-326.
Cardinale, D. et al. (Jun. 2, 2015). "Early Detection of Anthracycline Cardiotoxicity and Improvement with Heart Failure Therapy," Circulation 131(22):1981-1988.
Chatterjee, K. (Jan. 2010, e-pub. Dec. 2009). "Doxorubicin Cardiomyopathy," Cardiology 115(2):155-162.
Chen, L. (2015) "Study On Molecular Mechanism Of Quercetin Alleviating Cardiotoxicity Of Adriamycin," Master Thesis, Zhejiang University (Abstract Only with Machine Translation), 2 pages.
Chen, J.Y. et al. (May 10, 2012). "Proteomic analysis of quercetin-induced cardioprotective effects," Genomic Medicine, Biomarkers, and Health Sciences 4:51-53.
Choi, et al. (2011). "Effects of Myricetin on the Bioavailability of Doxorubicin for Oral Drug Delivery in Rats: Possible of CYP3A4 and P-glycoprotein Inhibition by Myricetin," Arch. Pharm. Res. 34(2):309-315.
Chu, T.F. et al. (Dec. 15, 2007). "Cardiotoxicity Associated with the Tyrosine Kinase Inhibitor Sunitinib," Lancet 370(9604):2011-2019.
Colombian Opposition filed by Laboratorios Legrand S.A., mailed Apr. 16, 2019, against Colombian Patent Application No. NC2018/0009132, filed Feb. 3, 2017, 13 pages (including English Translation).
Czepas, J. et al. (Oct. 30, 2014, e-pub. Oct. 30, 2014). "The Flavonoid Quercetin: Possible Solution For Anthracycline-Induced Cardiotoxicity And Multidrug Resistance", Biomed. Pharmacother. 68(8):1149-1159.
Deng et al. (Nov. 18, 2014). "Dexrazoxane May Prevent Doxorubicin-Induced DNA Damage via Depleting Both Topoisomerase II Isoforms" BMC Cancer 14:842, 11 pages.
Dresdale, A.R. et al. (Dec. 1982). "Prospective randomized study of the role of N-acetyl cysteine in reversing doxorubicin-induced cardiomyopathy," Am J Clin Oncol. 5(6):657-663. (Abstract Only).
Du, G. et al. (May 26, 2009). "Quercetin Greatly Improved Therapeutic Index of Doxorubicin Against 4T1 Breast Cancer by its Opposing Effects on HIF-1a in Tumor and Normal Cells," Cancer Chemotherapy and Pharmacology 65:277-287.

(56) References Cited

OTHER PUBLICATIONS

Duran, R.M. et al. (December 1992-1993). "INFORMATION: Antioxidant Activity of Phenolic Compounds," *Grasas y Aceites* 44(2):101-106, 13 pages, (including English Translation).

European Partial Search Report and Provisional Opinion dated Oct. 8, 2019, for European Patent Application No. 17748307.0, filed Feb. 3, 2017, 14 pages.

Extended European Search Report dated Jan. 10, 2020, for European Patent Application No. 17748307.0, filed Feb. 3, 2017, 14 pages.

Fullbright, J.M. (Nov. 2010). "Can Anthracycline Therapy for Pediatric Malignancies Be Less Cardiotoxic?," Curr Oncol Rep 12(6):411-419.

Hasinoff, D. et al. (Dec. 1, 2003). "The Oral Iron Chelator ICL670A (deferasirox) Does Not Protect Myocytes Against Doxorubicin," Free Radic Biol Med 35(11):1469-1479. (Abstract Only).

International Preliminary Report on Patentability Chapter dated Aug. 7, 2018, for Patent Application No. PCT/US2017/16582, filed Feb. 3, 2017, 15 pages.

International Search Report dated May 25, 2017 for Patent Application No. PCT/US2017/16582, filed Feb. 3, 2017, 5 pages.

Jayakumar, J.K. et al. (Apr. 2014) "Evaluation Of Protective Effect Of Myricetin, A Bioflavonoid In Dimethyl Benzanthracene-Induced Breast Cancer In Female Wistar Rats," *South Asian J Cancer.* 3(2):107-111.

Jo, S.H. et al. (Epub Mar. 31, 2013) "Evaluation of Short-Term Use of N-Acetylcysteine as a Strategy for Prevention of Anthracycline-Induced Cardiomyopathy: EPOCH Trial—A Prospective Randomized Study," Korean Circ J. 43:174-181.

Jordan, K. et al. (2009). "Anthracycline Extravasation Injuries: Management With Dexrazoxane," Therapeutics and Clinical Risk Management 5:361-369.

Kaiserová, H. et al. (Sep. 2007). "Flavonoids As Protectors Against Doxorubicin Cardiotoxicity: Role Of Iron Chelation, Antioxidant Activity And Inhibition Of Carbonyl Reductase," Biochimica et Biophysica Acta (BBA)—Molecular Basis of Disease 1772(9):1065-1074.

Kalepu, S. et al. (Sep. 2015, e-pub. Aug. 24, 2015). "Insoluble Drug Delivery Strategies: Review of Recent Advances and Business Prospects," Acta Pharm Sin B 5(5):442-453.

Kane, R.C. et al. (Apr. 2008). "Dexrazoxane (Totect$^{tm}$): FDA Review and Approval for the Treatment of Accidental Extravasation Following Intravenous Anthracycline Chemotherapy," The Oncologist 13:445-450.

Kerkela, R. et al. (Aug. 2006, e-pub. Jul. 23, 2006). "Cardiotoxicity of the Cancer Therapeutic Agent Imatinib Mesylate," *Nature Medicine* 12(8):908-916.

Knekt, P. et al. (Sep. 2002). "Flavonoid Intake and Risk of Chronic Diseases," *Am J Clin Nutr.* 76(3):560-568.

Krusch, M. et al. (Dec. 15, 2009). "The Kinase Inhibitors Sunitinib and Sorafenib Differentially Affect NK Cell Antitumor Reactivity In Vitro," *Journal of Immunology* 183:8286-8294.

Lefrak, E.A. et al. (Aug. 1973). "A Clinicopathologic Analysis Of Adriamycin Cardiotoxicity," Cancer 32(2):302-314.

Li, Y. et al. (Dec. 2012). "Minireview: Therapeutic Potential of Myricetin in Diabetes Mellitus," *Toxicology Letters* 1(2012):19-25.

Lipshultz, S.E. et al. (Apr. 20, 2005). "Chronic Progressive Cardiac Dysfunction Years After Doxorubicin Therapy for Childhood Acute Lymphoblastic Leukemia," *Pediatric Oncology* 23(12):2629-2636.

Lopez-Lazaro, M. et al. (Feb. 2010, e-pub. Dec. 16, 2009). "The Dietary Flavonoids Myricetin and Fisetin Act as Dual Inhibitors of DNA Topoisomerases I and II in Cells," *Mutation Research* 696(1):41-47.

Ma, Z. et al. (Dec. 2015, e-pub. Nov. 30, 2015). "Myricetin Attenuates Depressant-Like Behavior in Mice Subjected to Repeated Restraint Street," Int J. Mol. Sci. 16(12):28377-28385.

Manuela, S. et al. (Nov. 2007). "The Kinase Inhibitors Sunitinib (Sutent®) and Sorafenib (Nexavar®) Differentially Affect Reactivity of NK Cells Against Renal Cell Cancer," *Blood* 110(11):4182, 3 pages.

Martin, E. et al. (Jan. 8, 2009). "Evaluation of the Topoisomerase II-inactive Bisdioxopiperazine ICRF-161 as a Protectant Against Doxorubicin-Induced Cardiomyopathy," Toxicology 255(1-2):72-79. (Abstract Only).

Menna, P. et al. (Apr. 1, 2008). "Cardiotoxicity of Antitumor Drugs," *Chemical Research in Toxicology* 21(5):978-989.

Mirza, Y.A. et al. (2015). "Long-Term Response Of Classic Kaposi's Sarcoma To Intralesional Doxorubicin: A Case Report," Case Reports in Dermatology 7(1):17-19.

Muñoz, C. et al. (Jul. 2016). "Cytotoxic Compounds From Plant Sources And Their Relationship With Inhibitor Of Apoptosis Proteins," Revista Colombiana de Cancerologia 20(3):124-134. (Machine Translation).

Nowis, D. et al. (Jun. 2010). "Cardiotoxicity of the Anticancer Therapeutic Agent Bortezomib," *The American Journal of Pathology* 176(6):2658-2668.

Parabathina, R.K. et al. (2010). "Cardioprotective effects of vitamin E, morin, rutin and quercetin against Doxorubicin induced oxidative stress of rabbits: A biochemical study," *J. Chem. Pharm. Res.*, 2(3):754-765.

Pfizer. (Oct. 2013). "Highlights of Prescribing Information: Doxorubicin Hydrochloride," Pfizer Labs, Reference ID #3399075, 26 pages.

Sadzuka, Y et al. (Jun. 16, 1997). "Protective Effect of Flavonoids on Doxorubicin-Induced Cardiotoxicity," *Toxicology Letters* 92(1):1-7.

Saeki, Y. et al. (2010). "Proteasome Inhibitors," Nihon Rinpen 68(10):1818-1822. (English Abstract).

Šmůnek, T. et al. (Jan.-Feb. 2009) "Anthracycline-Induced Cardiotoxicity: Overview of Studies Examining the Roles of Oxidative Stress and Free Cellular Iron," Pharmacological Reports 61:154-171.

Singapore Search Report and Written Opinion, dated Nov. 6, 2019, for Singapore Patent Application No. 11201805375P, filed Feb. 3, 2017.

Soucek, P. et al. (Feb. 1, 2011). "New Model System For Testing Effects Of Flavonoids On Doxorubicin-Related Formation Of Hydroxyl Radicals", Anti-Cancer Drugs 22(2):176-184.

Swain, S.M. et al. (Apr. 1997). "Cardioprotection with Dexrazoxane for Doxorubicin-Containing Therapy in Advanced Breast Cancer," *Journal of Clinical Oncology* 15(4): 1318-1332.

Swain, S.M. et al. (May 19, 2003). "Congestive Heart Failure in Patients Treated with Doxorubicin," *Cancer* 97(11):2869-2879.

Tebbi, C.K. et al. (Feb. 10, 2007). "Dexrazoxane-Associated Risk for Acute Myeloid Leukemia/Myelodysplastic Syndrome and Other Secondary Malignancies in Pediatric Hodgkin's Disease," *J Clin Oncol.* 25(5):493-500.

Tiwari, R. et al. (Oct. 2009). Cardioprotective Potential of Myricetin in Isoproterenol-induced Myocardial Infarction in Wistar Rats, *Phytotherapy Research* 23(10):1361-1366.

U.S. Appl. No. 16/737,849, filed Jan. 8, 2020, for Christopher G. Armstrong, et al.

U.S. Department of Health and Human Services, Food and Drug Administration, Center for Drug Evaluation and Research (CDER). (Oct. 2015). "Liposome Drug Products Chemistry, Manufacturing, and Controls; Human Pharmacokinetics and Bioavailability; and Labeling Documentation, Guidance for Industry, (Draft Guidance)," Publication, 17 pages.

Udhrain, A. et al. (Sep. 2007, e-pub. Sep. 2007). "Pegylated Liposomal Doxorubicin in the Treatment of AIDS-Related Kaposi's Sarcoma," *International Journal of Nanomedicine* 2(3):345-352.

Vejpongsa, P. et al. (Sep. 2014) "Prevention of anthracycline-induced cardiotoxicity: challenges and opportunities." J Am Coll Cardiol. 64(9):938-945.

Wouters, K.A. (Dec. 2005). Protecting Against Anthracycline-induced Myocardial Damage: A Review of the Most Promising Strategies, Br J Haematol 131(5):561-578.

Written Opinion International Searching Authority dated May 25, 2017, for Patent Application No. PCT/US2017/016582, filed Feb. 3, 2017, 14 pages.

Xiao,J. et al. (Feb. 5, 2012). "Kaempferol Protects Against Doxorubicin-Induced Cardiotoxicity In Vivo And In Vitro," Toxicology 292(1):53-62.

(56) References Cited

OTHER PUBLICATIONS

Xu, Z. et al. (Mar. 1, 2009, e-pub. Mar. 13, 2009). "Cardiotoxicity of Tyrosine Kinase Inhibitors in Chronic Myelogenous Leukemia Therapy," *Hematol Rev.* 1(1):e4, 5 pages.

Yao, Y. (Jan. 2014). "Preformulation Studies of Myricetin: A Natural Antioxidant Flavonoid," Pharmazie. 69(1):19-26.

Yeh, E.T.H. et al. (Dec. 1, 2016). "Oncocardiology—Past, Present, and Future: A Review," JAMA Cardiol. 1(9):1066-1072.

Yuan, X. et al. (2015, e-pub. Nov. 2, 2015). "Myricetin Ameliorates the Symptoms of Collagen-Induced Arthritis in Mice by Inhibiting Cathepsin K Activity," *Immunopharmacol Immunotoxicol* 37(6):513-519.

Zhang, S, et al. (Nov. 2012). "Identification of the Molecular Basis of Doxorubicin-Induced Cardiotoxicity," Nat Med 18(11):1639-1642.

Zhang, S. et al. (Mar. 20, 2014). "Enhancement of Recombinant Myricetin on the Radiosensitivity of Lung Cancer A549 and H1299 Cells," Diagn Pathol. 9(68):1-7.

FIG. 6A

Total Cell Count

| DOX Concentration (µM) | AVERAGE | | STDEV | |
|---|---|---|---|---|
| | 0 | 1.25 | 0 | 1.25 |
| No Treatment | 8543.50 | 3195.67 | 251.02 | 241.42 |
| Myricetin (79 µM) | 8586.33 | 6187.67 | 285.98 | 194.28 |

FIG. 6B

% Cells

| DOX Concentration (µM) | AVERAGE | | STDEV | |
|---|---|---|---|---|
| | 0 | 1.25 | 0 | 1.25 |
| No Treatment | 100.00% | 37.40% | 2.94% | 2.83% |
| Myricetin (79 µM) | 100.50% | 72.43% | 3.35% | 2.27% |

FIG. 6C

Beat Rate (BPM)

| DOX Concentration (µM) | AVERAGE | | STDEV | |
|---|---|---|---|---|
| | 0 | 1.25 | 0 | 1.25 |
| DMSO | 33.33 | 0.00 | 5.13 | 0.00 |
| Myricetin (79 µM) | 39.33 | 37.33 | 9.45 | 3.21 |

DOX = Doxorubicin; MYR = Myricetin

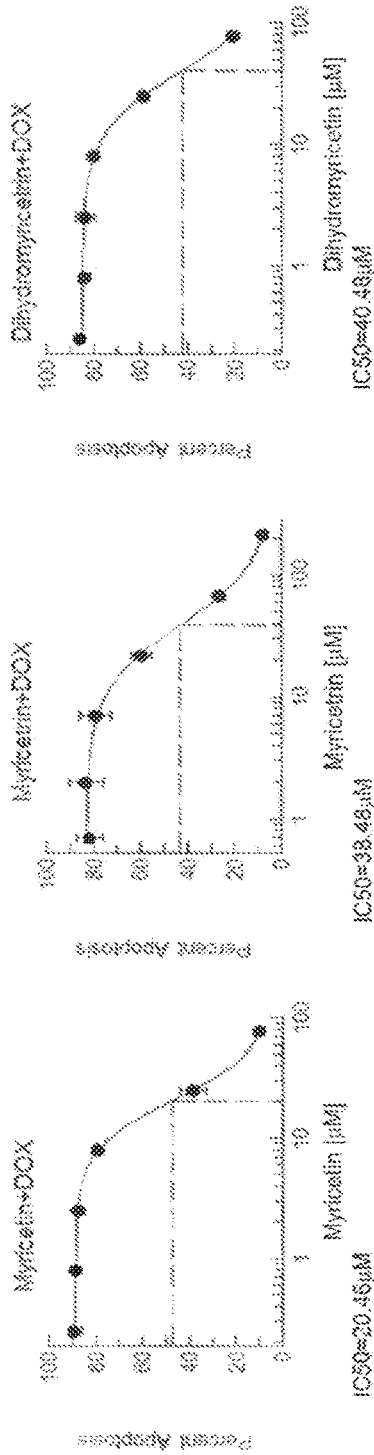

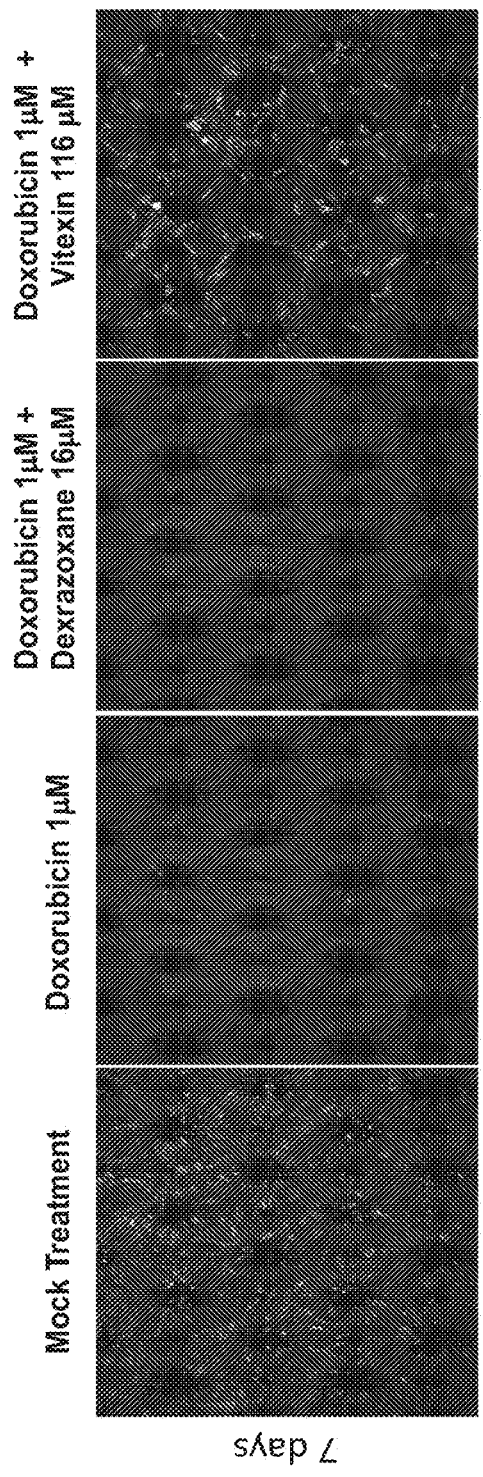

Dox = Doxorubicin; KAE = Kaempferol; VIT = Vitexin

PHARMACEUTICAL COMPOSITIONS AND METHODS FOR COUNTERING CHEMOTHERAPY INDUCED CARDIOTOXICITY

CROSS-REFERENCE TO RELATED APPLICATIONS

This application is a continuation of U.S. patent application Ser. No. 16/737,849, filed Jan. 8, 2020, now issued as U.S. Pat. No. 10,874,633 on Dec. 29, 2020, which is a continuation of U.S. patent application Ser. No. 16/075,569, filed Aug. 3, 2018 and adopts International filing date of Feb. 3, 2017, now issued as U.S. Pat. No. 10,806,716 on Oct. 20, 2020, which is a National Stage application under 35 U.S.C. § 371 of International Application No. PCT/US2017/016582, filed Feb. 3, 2017, which claims the priority benefits of U.S. provisional application Ser. No. 62/291,480, filed Feb. 4, 2016, and U.S. provisional application Ser. No. 62/348,102, filed Jun. 9, 2016, the disclosure of each of which is incorporated herein by reference in its entirety.

BACKGROUND

Cardiotoxicity and congestive heart failure are serious side-effects of oncological therapies, most prominently those comprising anthracyclines, which are administered to greater than one million cancer patients per year and half of all childhood cancer patients. Adverse cardiac side effects are also observed in patients treated with protein kinase inhibitors and antibody-based biologics that target protein kinase. Certain reductions in heart failure rates have been achieved by capping the maximal doses of anthracyclines and by changing their administration schedules, all of which severely limits the therapeutic potentials of these anticancer agents. The cardiotoxicity of cancer drugs can also preclude those patients with pre-existing cardiac conditions from receiving treatment.

Anthracyclines are generally a class of compounds that have the structural core of anthracene. They often are highly effective chemotherapeutics and therefore are used for the treatment of many cancers, including leukemias, lymphomas, breast, uterine, ovarian, bladder cancer, and lung cancers and are often used in childhood cancer treatment regimens. Some anthracycline drugs include doxorubicin, daunorubicin, idarubicin, and epirubicin. Although the exact mechanisms may yet to be validated, anthracyclines have been reported to work by inhibiting DNA and RNA synthesis, promoting free radical formation through redox cycling, with iron promoting the conversion of superoxide into hydroxyl radicals; inhibiting topoisomerases (e.g., topoisomerases IIα and/or IIβ); and evicting histones from open chromosomal areas.

A common side effect of anthracycline use is associated with cardiotoxicity, which is dose dependent and may also result from cumulative exposures. Cardiotoxicity, in some instances, may result from the formation of toxic reactive oxygen species through redox cycling during the metabolism of anthracyclines and from the formation of double-stranded DNA breaks caused by inhibition of topoisomerase II. The reactive oxygen species (ROS) may activate apoptotic pathways, leading to cell death in both cancer and normal cells. Cardiomyocytes may be sensitive to the oxidative stress. Cardiac mitochondria can be easily injured by anthracycline and anthracycline-iron complexes, which have a high affinity for dianionic phospholipid cardiolipin that is present at a high concentration in the inner mitochondrial membrane.

Some protein kinase inhibitors-including small molecule and biologic inhibitors may also cause cardiotoxicity. Protein kinase inhibitors are a wide class of compounds that inhibits the activity of protein kinases and can be used in cancer treatments. Tyrosine kinases regulate a variety of cellular functions including cell growth (e.g., epidermal growth factor ("EGFR") and dysregulation may lead to certain forms of cancer. Inhibition of such tyrosine protein kinases may be accomplished by using small molecules that bind to the ATP pocket of a given protein kinase, blocking it from catalyzing the phosphorylation of target proteins. Small molecules may cause cardiotoxicity by: (1) selectively inhibiting kinases that also play a role in heart cells (e.g., on-target side effects); (2) targeting multiple kinases in the same pathway (e.g., impacting off-target kinases); and (3) inhibiting non-kinase targets that play a role in heart function; small molecules may also cause cardiotoxicity through a different mechanism. Cardiotoxicity of TK1 inhibitors such as imatinib mesylate (Gleevec®), Nilotinib (Tasigna®), sorafenib (Nexavar®), sunitinib (Sutent®) and dasatinib (Sprycel®) has been reported previously (Chu et al., Lancet (2007) 370:2011-2019; Xu et al., Hematol Rev. (2009) Mar1; 1(1): e4 Kerketla et al., Nature Medicine (2006) 12:908-916).

Protein kinase activity may also be inhibited by biologic drugs such as monoclonal antibodies against receptor protein kinases. These therapeutics may exert efficacy, by preventing receptor protein kinases from activating and are generally able to bind cell surface antigens with high specificity. Several monoclonal antibodies target receptor protein kinases that play an important role in heart function and thus may cause cardiotoxicity as a result. Trastuzumab and bevacizumab are examples of monoclonal antibodies that can cause cardiotoxicity (e.g., heart failure resulting from cardiac tissue damage, electrophysiological dysfunction, mitochondrial toxicity, apoptosis, or oxidative stress). Proteasome inhibitor chemotherapy compounds (e.g., bortezomib) are also known to be associated with cardiotoxicity and heart failure.

Currently, the bisdioxopiperazine dexrazoxane (DEX) is the only drug approved for reducing the incidence of cardiotoxicity and heart failure in cancer patients receiving anticancer agents. Despite its clinical effect, DEX is only approved for the treatment of patients with metastatic breast cancer who have already received accumulated dose of 300-500 mg/m² anthracyclines like doxorubicin or epirubicin. DEX is not approved for use in children and adolescents, it is particularly disheartening to find reports of high incidences of heart failure in anthracycline-treated young children in their later life of post-cancer. Further, the limited indication approval and use are also testament of DEX's shortcomings, which include interfering with antitumor efficacy of anthracyclines, inducing secondary malignancies, and causing blood and bone marrow disorders.

Given the serious impact that many cancer therapies exert on heart function, there exists a clear clinical need for developing an effective drug that prevents, alleviates, or eliminates cardiotoxicity caused by anthracyclines, protein kinase inhibitors (e.g., tyrosine kinase inhibitor), proteasome inhibitors and other cancer treatments. Of particular importance is the development of drugs that can prevent or reduce cancer drug-induced cardiotoxicity without significantly interfering with the anticancer action of the cancer drug. Also important is the development of cardioprotective drugs that do not cause serious side effects such as neutropenia, worsening of heart problems, or increased risk of secondary malignancies. These potential drugs will significantly improve existing cancer therapy, not only by protecting from potential heart injuries in cancer patients, but also by enabling chemotherapy doses optimized to achieve maximum-anti-cancer effects.

BRIEF DESCRIPTION OF THE DRAWINGS

FIG. 6A-C depict a chart providing the raw data (6A) or normalized data (6B) for the experiments depicted in FIG. 3, or the raw data for the experiments depicted in FIG. 5 (6C).

FIG. 7A-C depict the effects of myricetin (7A), myricitrin/myricetrin (7B), or dihydromyricetin (7C) on doxorubicin-induced apoptosis at increasing concentrations in human induced pluripotent stem cell-derived cardiomyocytes (iPSC-CM) at 3 days following treatment.

FIG. 27A-D depict the effects of mock treatment (27A), DEX (27B), a co-administration of doxorubicin and dexrazoxan (27C), or a co-administration of doxorubicin and vitexin (27D), on mitochondrial health in human induced pluripotent stem cell-derived cardiomyocytes.

BRIEF SUMMARY

Figure 1:
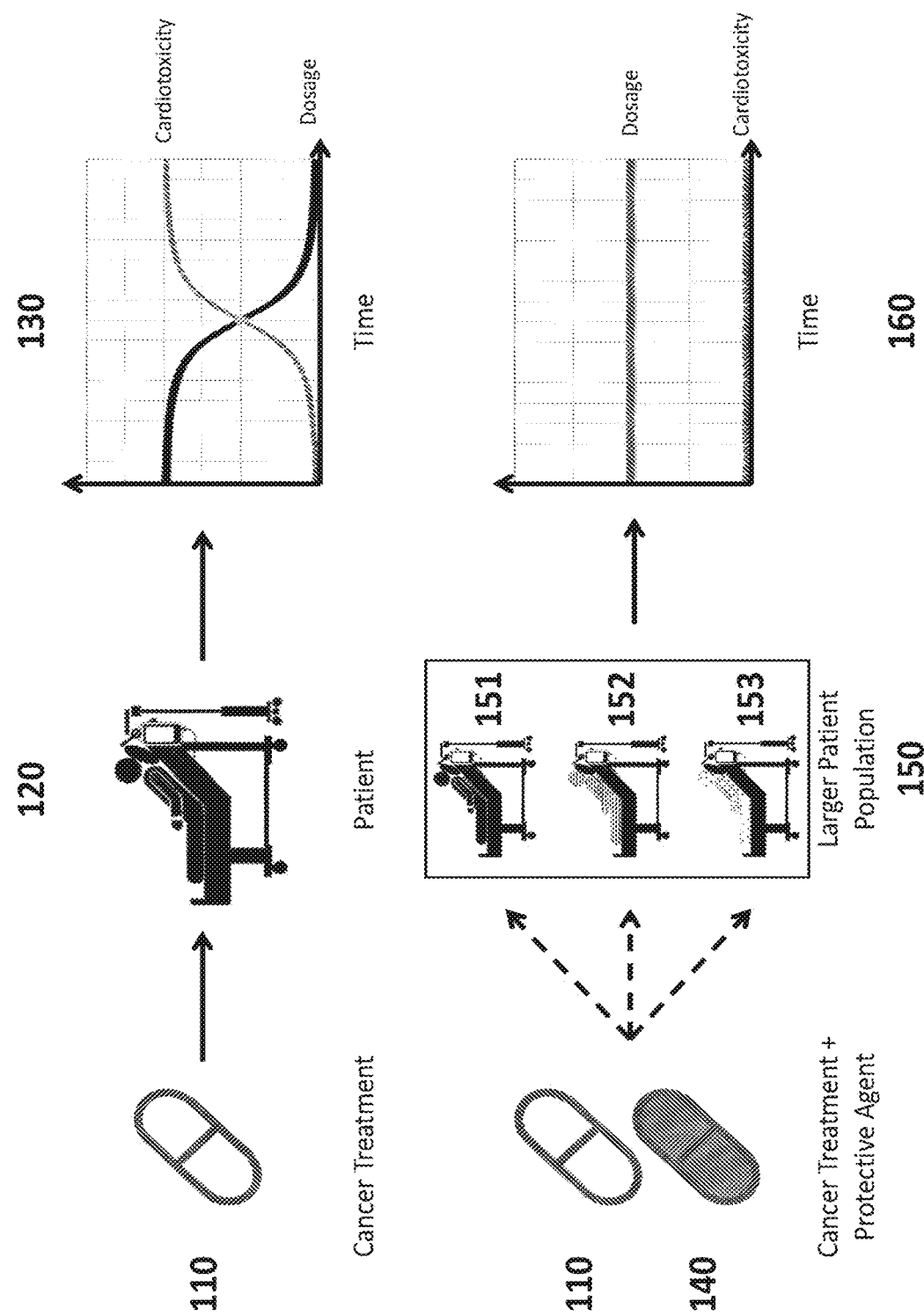
FIG. 1 generally depicts a method of reducing cancer treatment-induced cardiotoxicity in a patient by co-administering a cancer treatment and protective agent to the patient.

This disclosure provides composition, kits; and methods for protecting the heart and for preventing heart failure in patients treated with anthracyclines, protein kinase inhibitors and/or biologic agents. By minimizing the risk of potentially devastating heart failure in cancer patient under chemotherapy, conventional cancer treatment can achieve improved efficacy and safety with the invention described herein.

The compositions include one or more protective agents with or without an anticancer agent. The kits often include one or more protective agents, and sometimes anticancer agents as well. The methods include methods of reducing, preventing, or eliminating cardiotoxicity induced by a drug or other therapy including cancer treatments.

In some aspects, this disclosure provides a pharmaceutical composition comprising a protective agent of according to Formula 1,

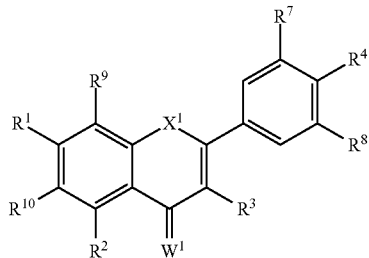

Formula 1 wherein:

$X^1$ is $CR^5R^6$, $NR^5$, O, S, C=O, or C=S;

each of $R^1$, $R^2$, $R^3$, $R^5$, $R^6$, $R^9$, and $R^{10}$ is independently alkyl, alkenyl, alkynyl, alkoxy, acyl, acyloxy, carboxylic acid, ester, amine, amide, carbonate, carbamate, nitro, thioether, thioester, cycloalkyl, heteroalkyl, heterocyclyl, monosaccharide, aryl, or heteroaryl, any of which is substituted or un substituted, halogen, hydroxyl sulfhydryl nitro nitroso cyano, azido, or H;

$R^4$, $R^7$ and $R^8$ are alkoxy, hydroxyl or H;

$W^1$ is O or S; or a salt thereof.

In some aspects, $X^1$ can be O or S; each of $R^1$, $R^2$, $R^3$, $R^9$, and $R^{10}$ can be independently alkoxy, cycloalkyl, halogen, hydroxyl, sulfhydryl, nitro, nitroso, cyano, azido, or H; and each of $R^4$, $R^7$ and $R^8$ can be independently alkoxy, hydroxyl or H.

In some aspects, $X^1$ is O; each of $R^1$, $R^2$, $R^1$, $R^9$, and $R^{10}$ can be independently alkoxy, cycloalkyl, halogen, hydroxyl, sulfhydryl, nitro, nitroso, cyano, azido, or H; and each of $R^4$, $R^7$ and $R^8$ can be independently alkoxy, hydroxyl or H.

In yet other aspects, $X^1$ is O; each of $R^1$ and $R^2$ can be independently hydroxyl or H; each of $R^3$, $R^9$ and $R^{10}$ can be independently cycloalkyl, heterocyclyl, hydroxyl, or H; $R^4$ is hydroxyl; and each of $R^7$ and $R^8$ can be independently hydroxyl or H.

In yet other aspects, $X^1$ is O; $R^1$ is hydroxyl; each of $R^2$ and $R^3$ can be independently hydroxyl or H; $R^9$ and $R^{10}$ are H; $R^4$ is hydroxyl; and each of $R^7$ and $R^8$ can be independently hydroxyl or H.

In yet other aspects, $X^1$ is O; $R^1$ is hydroxyl; each of $R^2$ and $R^3$ can be independently hydroxyl or H; $R^9$ can be heterocyclyl or H; of $R^{10}$ is H; $R^4$ can be independently hydroxyl or H; and each of $R^7$ and $R^8$ can be independently hydroxyl or H.

In yet other aspects, $X^1$ is O; $R^1$ is hydroxyl; each of $R^2$ and $R^9$ can be independently hydroxyl or H; $R^3$ can be cycloalkyl, hydroxyl or H; $R^{10}$ is H; R4 is hydroxyl; and each of $R^7$ and $R^8$ can be independently hydroxyl or H. In one embodiment, cycloalkyl of $R^3$ can be a monosaccharide.

In some embodiments, the pharmaceutical composition may comprise myricetin and is a compound according to the following formula.

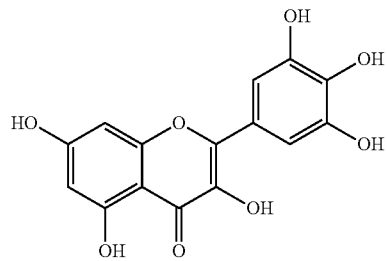

In some embodiments, the pharmaceutical composition may comprise myricetrin/myricitin and is a compound according to the following formula.

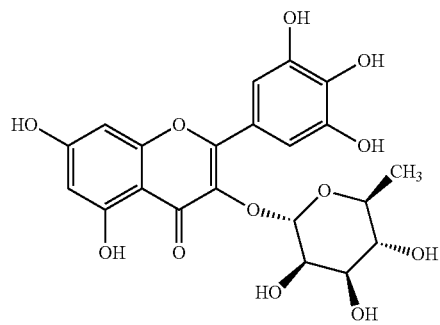 [SMILES: C[C@@H]1O[C@@H](Oc2c(-c3cc(O)c(O)c(O)c3)oc3cc(O)cc(O)c3c2=O)[C@H](O)[C@H](O)[C@H]1O]

In some embodiments, the pharmaceutical composition may comprise robinetin and is a compound according to the following formula.

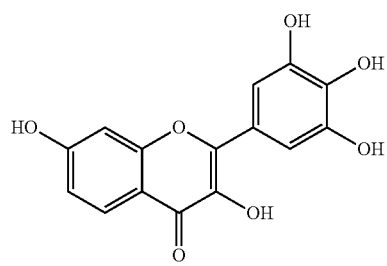 [SMILES: O=c1c(O)c(-c2cc(O)c(O)c(O)c2)oc2cc(O)ccc12]

In some embodiments, the pharmaceutical composition may comprise tricetin and is a compound according to the following formula.

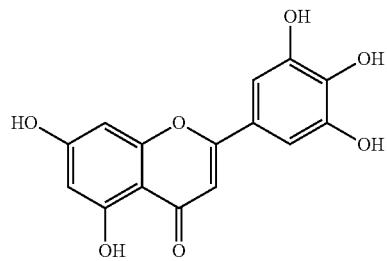 [SMILES: O=c1cc(-c2cc(O)c(O)c(O)c2)oc2cc(O)cc(O)c12]

In some embodiments, the pharmaceutical composition may comprise 7,3',4',5'-tetrahydroxyflavone and is a compound according to the following formula.

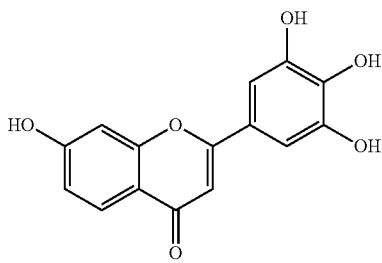 [SMILES: O=c1cc(-c2cc(O)c(O)c(O)c2)oc2cc(O)ccc12]

In some embodiments, the pharmaceutical composition comprises ficetin. In some embodiments, the pharmaceutical composition comprises quercetin. In some embodiments, the pharmaceutical composition comprises kaempferol. In some embodiments, the protective agent within the pharmaceutical composition can be a compound with the following structure:

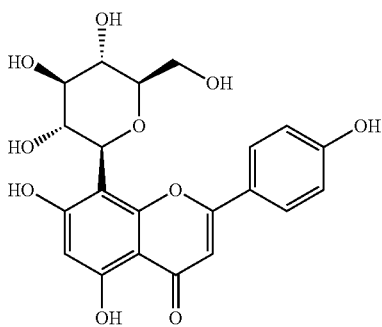 [SMILES: O=c1cc(-c2ccc(O)cc2)oc2c([C@@H]3O[C@H](CO)[C@@H](O)[C@H](O)[C@H]3O)c(O)cc(O)c12]

In a particular example, the protective agent within the pharmaceutical composition can be vitexin.

In some embodiments, the pharmaceutical composition may include one or more chemotherapy drug(s) (anticancer agent) or biologic agent(s) In some embodiments, the pharmaceutical composition can include a chemotherapy drug. In some embodiments, the pharmaceutical composition may include one or more chemotherapy drug(s) (anticancer agent) and one or more of the protective agent(s) selected from the group consisting of myricetin, tricetin (5,7,3',4',5'-pentahydroxyflavone), robinetin, ficetin, vitexin, 7,3',4',5'-tetrahydroxyflavone, and myricetrin.

In some embodiments, the pharmaceutical composition may comprise an anthracycline or salt thereof. In some embodiments, the anthracycline can be daunorubicin, doxorubicin, epirubicin, idarubicin, mitoxantrone, or valrubicin. In some embodiments, the anthracycline is doxorubicin. In some embodiments, the anthracycline is epirubicin. In some embodiments, the anthracycline is idarubicin.

In some embodiments, the chemotherapy drug can be a protein kinase inhibitor. In some embodiments, the protein kinase inhibitor is afatinib, axitinib, bosutinib, cabozantinib, carfilzomib, ceritinib, cobimetanib, crizotinib, dabrafenib, dasatinib, erlotinib, everolimus, gefitinib, ibrutinib, imatinib, lapatinib, lenvatinib, nilotinib, nintedanib, osimertinib, palbociclib, pazopanib, pegaptanib, ponatinib, regorafenib, ruxolitinib, sirolimus, sorafenib, sunitinib, tofacitinib, tofacitinib, temsirolimus, trametinib, vandetanib, vemurafenib, or vismodegib.

In some embodiments, the chemotherapy drug can be a proteasome inhibitor. In a particularly example, the proteasome inhibitor can be bortezomib.

In some embodiments, the protein kinase inhibitor can be a tyrosine kinase inhibitor. In some embodiments, for example, the tyrosine kinase inhibitor is selected from the group consisting of sorafenib, sunitinib, bosutinib, gefitinib, dasatinib, dabrafenib, vemurafenib, imatinib, lapatinib, mesylate, and nilotinib. In a particular example, the tyrosine kinase inhibitor is sorafenib. In another particular example, the tyrosine kinase inhibitor is sunitinib.

In some embodiments, the chemotherapy drug can be a biologic agent. In some embodiments, the biologic agent is an antibody. In some embodiments, the antibody can be adotrastuzumabemtansine, alemtuzumab, bevacizumab, blinatumomab, brentuximab vedotin, catumaxomab, cetuximab, gemtuzumab ozogamicin, ibritumomab tiuxetan, ipilimumab, necitumumab, nivolumab, obinutuzumab, ofatumumab, panitumumab, pembrolizumab, pertuzumab, ramucirumab, rituximab, tositurnomab-I131, or trastuzumab. In one particular example, the antibody is trastuzumab.

In some embodiments, the pharmaceutical composition can be a liquid composition. In some embodiments, the pharmaceutical composition can be a capsule, a gel capsule, or a liposome. In some embodiments, the pharmaceutical composition can be a tablet.

In some embodiments, the pharmaceutical composition may also include dexrazoxane as an additional protective agent.

In some embodiments, the pharmaceutical composition can comprise at least 1 mg of one or more protective agents. In some embodiments, the pharmaceutical composition can comprise between 0.1 mg and 200 mg of one or more protective agents. In some embodiments, the pharmaceutical composition can comprise between 0.1 mg and 300 mg of one or more protective agents.

In some embodiments, two protective agents are present and co-formulated together. In some embodiments, the two protective agents can be present as distinct entities within the pharmaceutical composition. In some embodiments, the pharmaceutical composition can comprise the chemotherapy drug and the chemotherapy drug is co-formulated with one of the two protective agents.

In some aspects, this disclosure provides a pharmaceutical composition comprising
(a) a protective agent selected from the group consisting of: a compound according to Formula 2,

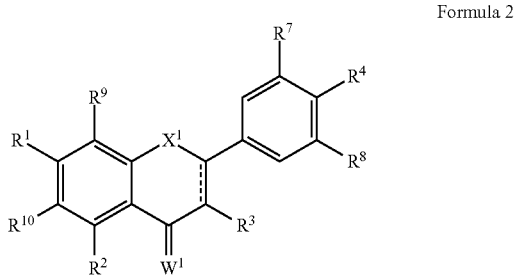

Formula 2 wherein:
===== represents a single or double bond;
$X^1$ is $CR^5R^6$, $NR^5$, O, S, C=O, or C=S;
each of $R^1$, $R^2$, $R^3$, $R^5$, $R^6$, $R^9$, and $R^{10}$ is independently alkyl, alkenyl, alkynyl, alkoxy, acyl, acyloxy, carboxylic acid, ester, amine, amide, carbonate, carbamate, nitro, thioether, thioester, cycloalkyl, heteroalkyl, heterocyclyl, aryl, or heteroaryl, any of which is substituted or unsubstituted, halogen, hydroxyl, sulfhydryl, nitro, nitroso, cyano, azido, or H;

$R^4$, $R^7$ and $R^8$ are hydroxyl;

$W^1$ is O or S;

or a salt thereof; and (b) a chemotherapy drug or a biologic agent.

In some embodiments, the pharmaceutical composition may comprise an anticancer agent or a chemotherapy drug. In some embodiments, the protective agent is selected from the group consisting of myricetin, tricetin, robinetin, ficetin, vitexin, dihydrorobinetin, 7,3',4',5'-tetrahydroxyflavone, and myricetrin.

In some embodiments, the pharmaceutical composition may comprise one or more protective agents. In some embodiments, the pharmaceutical composition may comprise myricetin. In some embodiments, the pharmaceutical composition may comprise myricetrin. In some embodiments, the pharmaceutical composition may comprise robinetin. In some embodiments, the pharmaceutical composition may comprise dihydrorobinetin. In some embodiments, the pharmaceutical composition may comprise vitexin. In some embodiments, the pharmaceutical composition may comprise tricetin. In some embodiments, the pharmaceutical composition comprises quercetin. In some embodiments, the pharmaceutical composition comprises kaempferol.

In some embodiments, the pharmaceutical composition comprises an anthracycline or salt thereof. In some embodiments, the anthracycline is daunorubicin, doxorubicin, epirubicin, idarubicin, mitoxantrone, or valrubicin. In some embodiments, the anthracycline is doxorubicin. In some embodiments, the anthracycline is epirubicin. In some embodiments, the anthracycline is idarubicin.

In some embodiments, the chemotherapy drug can be a protein kinase inhibitor. In some embodiments, the protein kinase inhibitor is afatinib, axitinib, bosutinib, cabozantinib, carfilzomib, ceritinib, cobimetanib, crizotinib, dabrafenib, dasatinib, erlotinib, everolimus, gefitinib, ibrutinib, imatinib, lapatinib, lenvatinib, nilotinib nintedanib, osimertinib, palbociclib, pazopanib, pegaptanib, ponatinib, regorafenib, ruxolitinib, sirolimus, sorafenib, sunitinib, tofacitinib, tofacitinib, temsirolimus, trametinib, vandetanib, vemurafenib, or vismodegib.

In some embodiments, the chemotherapy drug is a proteasome inhibitor. In a particular example, the proteasome inhibitor is bortezomib.

In some embodiments, the protein kinase, inhibitor is a tyrosine kinase inhibitor. In some embodiments, the tyrosine kinase inhibitor is selected from the group consisting of sorafenib, sunitinib, bosutinib, gefitinib, dasatinib, dabrafenib, vemurafenib, imatinib, lapatinib, mesylate, and nilotinib. In a particular example, the tyrosine kinase inhibitor is sorafenib. In another particular example, the tyrosine kinase inhibitor is sunitinib.

In some embodiments, the chemotherapy drug is a biologic agent. In some embodiments, the biologic agent is an antibody. In some embodiments, the antibody is adotrastuzumabemtansine, alemtuzumab, bevacizumab, blinatumomab, brentuximab vedotin, catumaxomab, cetuximab, gemtuzumab ozogamicin, ibritumomab tiuxetan, ipilimumab, necitumumab nivolumab, obinutuzumab, ofatumumab, panitumumab, pembrolizumab, pertuzumab, ramucirumab, rituximab, tositumomab-I131, or trastuzumab. In a particular example, the antibody is trastuzumab. In a particular example, the antibody is bevacizumab.

In some embodiments, the pharmaceutical composition may comprise at least 1, 2, 3, 4, 5, 6, 7, 8, 9, 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 mg of one or more protective agents.

In some embodiments, the pharmaceutical composition may comprise between 0.1 mg and 50 mg of the protective agent. In some embodiments, the pharmaceutical composition may comprise between 1 mg and 10 mg of the protective agent. In some embodiments, the pharmaceutical composition may comprise between 1 mg and 20 mg of the protective agent. In some embodiments, the pharmaceutical composition may comprise between 1 mg, and 30 mg of the protective agent. In some embodiments, the pharmaceutical composition may comprise between 1 mg and 40 mg of the protective agent. In some embodiments, the pharmaceutical composition may comprise between 1 mg and 50 mg of the protective agent. In some embodiments, the pharmaceutical composition may comprise between 1 mg and 100 mg of the protective agent. In some embodiments, the pharmaceutical composition may comprise between 1 mg and 200 mg of the protective agent. In some embodiments, the pharmaceutical composition may comprise between 40 mg and 300 tug of the protective agent. In some embodiments, the pharmaceutical composition may comprise between 50 mg and 400 mg of the protective agent.

In some embodiments, the pharmaceutical composition may comprise the chemotherapy drug; and the chemotherapy drug and the protective agent are mixed within the pharmaceutical composition.

In some embodiments, the pharmaceutical composition comprises the chemotherapy drug wherein the dose of the chemotherapy drug is at least 0.1 mg. In some embodiments, the pharmaceutical composition comprises the chemotherapy drug wherein the dose of the chemotherapy drug is between 0.01 mg and 50 mg. In some embodiments, the pharmaceutical composition comprises the chemotherapy drug wherein the dose of the chemotherapy drug is between 0.01 mg and 100 mg. In some embodiments, the pharmaceutical composition comprises the chemotherapy drug wherein the dose of the chemotherapy drag is between 0.01 mg and 200 mg.

In some embodiments, the pharmaceutical composition comprises the biologic agent at a dose of at least 50 mg. In some embodiments, the pharmaceutical composition comprises a biologic agent at a dose of between 0.1 mg and 100 mg. In some embodiments, the pharmaceutical composition comprises a biologic agent at a dose of between 0.1 mg and 200 mg.

In some embodiments, the pharmaceutical composition comprises the chemotherapy drug and a molar ratio of the protective agent to the chemotherapy drug is at least 1:1. In some embodiments, the pharmaceutical composition comprises the chemotherapy drug and a molar ratio of the protective agent to the chemotherapy drug is at least 2:1. In some embodiments, the pharmaceutical composition comprises the chemotherapy drug and a molar ratio of the protective agent to the chemotherapy drug is at least 3:1. In some embodiments, the pharmaceutical composition comprises the chemotherapy drug and a molar ratio of the protective agent to the chemotherapy drug is at least 4:1. In some embodiments, the pharmaceutical composition comprises the chemotherapy drug and a molar ratio of the protective agent to the chemotherapy drug is at least 5:1. In some embodiments, the pharmaceutical composition comprises the chemotherapy drug and a molar ratio of the protective agent to the chemotherapy drag is at least 6:1. In some embodiments, the pharmaceutical composition comprises the chemotherapy drug and a molar ratio of the protective agent to the chemotherapy drag is at least 7:1. In some embodiments, the pharmaceutical composition comprises the chemotherapy drug and a molar ratio of the protective agent to the chemotherapy drug is at least 8:1. In some embodiments, the pharmaceutical composition comprises the chemotherapy drag and a molar ratio of the protective agent to the chemotherapy drug is at least 9:1. In some embodiments, the pharmaceutical composition comprises the chemotherapy drug and a molar ratio of the protective agent to the chemotherapy drag is at least 10:1. In some embodiments, the pharmaceutical composition comprises the chemotherapy drug and a molar ratio of the protective agent to the chemotherapy drug is at least 20:1. In some embodiments, the pharmaceutical composition comprises the chemotherapy drug and wherein a molar ratio of the protective agent to the chemotherapy drug is at least 100:1. In some embodiments, the pharmaceutical composition comprises the chemotherapy drug and wherein a molar ratio of the protective agent to the chemotherapy drag is at least 1:2. In some embodiments, the pharmaceutical composition comprises the chemotherapy drug and wherein a molar ratio of the protective agent to the chemotherapy drug is at least 1:3. In some embodiments, the pharmaceutical composition comprises the chemotherapy drug and wherein a molar ratio of the protective agent to the chemotherapy drug is at least 1:4. In some embodiments, the pharmaceutical composition comprises the chemotherapy drug and wherein a molar ratio of the protective agent to the chemotherapy drug is at least 1:5.

This disclosure provides methods for administering to a subject any of the pharmaceutical compositions disclosed herein. In some aspects, this disclosure provides a method for preventing, reducing, or eliminating cardiotoxicity or heart failure in general. In some aspects, this disclosure provides a method for preventing, reducing, or eliminating cardiotoxicity induced by a chemotherapy drug or biologic agent in a subject, the method comprising: administering one or more protective agent according to Formula 1, to the subject, thereby preventing, reducing, or eliminating the cardiotoxicity induced by the chemotherapy drug or biologic agent in the subject. In some cases, the pharmaceutical composition comprises a compound selected from the group consisting of such as myricetin, vitexin, robinetin, tricetin, ficetin, 7,3',4',5'-tetrahydroxyflavone, and myricitrin.

In some aspects, this disclosure provides a method for preventing, reducing, or eliminating cardiotoxicity induced by a chemotherapy drag or biologic agent in a subject, the method comprising: administering at least one protective agent according to Formula 1 or Formula 2, to the subject, thereby preventing, reducing, or eliminating the cardiotoxicity induced by the chemotherapy drug or biologic agent in the subject.

In some embodiments, the subject is administered a chemotherapy drag or biologic agent prior to the administering of one or more protective agent(s) according Formula 1 or 2, to the subject.

In some embodiments, the subject is administered a chemotherapy drug or biologic agent following the administering of at least two protective agents of Formula 1 or 2 to the subject.

In some aspects, this disclosure provides a method for treating cancer, the method comprising: (a) administering a chemotherapy drug or biologic agent to a subject, wherein the subject has cancer and the chemotherapy drug or biologic agent is capable of causing cardiotoxicity in the subject; and (b) administering at least one protective agent according to Formula 1 or Formula 2 to the subject, wherein the protective agent prevents, reduces, or eliminates the cardiotoxicity in the subject.

In some embodiments, the subject has a human suffering from cancer. In some embodiments, the cancer is bladder cancer, bone cancer, a brain tumor, breast cancer, esophageal cancer, gastrointestinal cancer, leukemia, liver cancer, lung cancer, lymphoma, myeloma, ovarian cancer, prostate cancer, a sarcoma, stomach cancer, or thyroid cancer.

In some embodiments, prior to the administration of the protective agent, the subject has a cardiac condition or has a history of having a cardiac condition. In some embodiments, the administration of the protective agent reduces the risk of the subject experiencing cardiotoxicity induced by the chemotherapy drug or biologic agent. In some embodiments, the administration of the protective agent reduces the risk of the subject experiencing cardiotoxicity induced by the chemotherapy drug or biologic agent by at least 30%, 40%, 50%, 60%, 70%, 80%, 90%, or 95%. In some embodiments, the cardiotoxicity may comprise cardiac tissue damage, electrophysiological dysfunction, mitochondrial toxicity, apoptosis, or oxidative stress. In some embodiments, the cardiotoxicity is cardiac tissue damage. In some embodiments, the cardiotoxicity is electrophysiological dysfunction.

In some embodiments, the chemotherapy drug used in the methods described herein may comprise an anthracycline or a salt thereof. In some embodiments, the anthracycline is daunorubicin, doxorubicin, epirubicin, idarubicin, mitoxantrone, or valrubicin. In some embodiments, the anthracycline is doxorubicin. In some embodiments, the anthracycline is epirubicin. In some embodiments, the anthracycline is idarubicin.

In some embodiments, the chemotherapy drug used in the methods described herein is a protein kinase inhibitor. In some embodiments, the protein kinase inhibitor is afatinib, axitinib, bosutinib, cabozantinib, carfilzomib, ceritinib, cobimetanib, crizotinib, dabrafenib, dasatinib, erlotinib, everolimus, gefitinib, ibrutinib, imatinib, lapatinib, lenvatinib, nilotinib, nintedanib, osimertinib, palbociclib, pazopanib, pegaptanib, ponatinib, regorafenib, ruxolitinib, sirolimus, sorafenib, sunitinib, tofacitinib, tofacitinib, temsirolimus, trametinib, vandetanib, vemurafenib, or vismodegib.

In some embodiments, the protein kinase inhibitor is a tyrosine kinase inhibitor. In some embodiments, the protein kinase inhibitor is a tyrosine kinase inhibitor. In some embodiments, the tyrosine kinase inhibitor is selected from the group consisting of sorafenib, sunitinib, bosutinib, gefitinib, dasatinib, dabrafenib, vemurafenib, imatinib, lapatinib, mesylate, and nilotinib. In a particular example, the tyrosine kinase inhibitor is sorafenib. In another particular example, the tyrosine kinase inhibitor is sunitinib.

In some aspect, the chemotherapy drug is a proteasome inhibitor. In one particular example, the proteasome inhibitor is bortezomib.

In some embodiments, the biologic agent used in the methods described herein can be an antibody. In some embodiments, the antibody is adotrastuzumabemtansine, alemtuzumab, bevacizumab, blinatumomab, brentuximab vedotin, catumaxomab, cetuximab, gemtuzumab ozogamicin, ibritumomab tiuxetan, ipilimumab, necitumumab, nivolumab, obinutuzumab, ofatumumab, panitumumab, pembrolizumab, pertuzumab, ramucirumab, rituximab, tositumomab-I131, or trastuzumab. In one particular example, the antibody is trastuzumab.

In some embodiments, the subject according to the methods described herein has a decreased QTc interval after administering the protective agent. In some cases, the protective agent is selected from the group consisting of such as myricetin, vitexin, robinetin, tricetin, ficetin, 7,3',4',5'-tetrahydroxyflavone, and myricitrin. In one particular example, the protective agent is myricetin.

In some embodiments, the chemotherapy drug and protective agent of Formula 1 or Formula 2 are administered concurrently to the subject. In some embodiments, the chemotherapy drug and protective agent are administered sequentially to the subject. In some embodiments, the protective agent is administered to the subject prior to the administration of the chemotherapy drug. In some embodiments, the protective agent is administered to the subject after the administration of the chemotherapy drug.

In some embodiments, at least two protective agents of Formula 1 or Formula 2 can be administered. For example, the at least two protective agents can be selected from the group consisting of such as myricetin, vitexin, robinetin, tricetin, ficetin, 7,3',4',5'-tetrahydroxyflavone, dihydrorobinetin, and myricitrin.

In some embodiments, one or more protective agent(s) can further comprise dexrazoxane.

This disclosure provides a method for treating or preventing organ damage in a subject comprising: administering one or more protective agents selected from the group consisting of such as myricetin, vitexin, robinetin, tricetin, ficetin, 7,3',4',5'-tetrahydroxyflavone, and myricitrin to a subject with organ damage, thereby treating or preventing organ damage in the subject.

This disclosure also provides kits. In some aspects, this disclosure provides a kit comprising: (a) a protective agent selected from the group consisting of myricetin, vitexin, robinetin, tricetin, ficetin, 7,3',4',5'-tetrahydroxyflavone, and myricitrin; and (b) a chemotherapy drug or a biologic agent.

In some aspects, this disclosure provides a kit comprising: (a) a protective agent selected from, the group consisting of myricetin, vitexin, robinetin, tricetin, ficetin, 7,3',4',5'-tetrahydroxyflavone, and myricitrin; (b) a chemotherapy drag or a biologic agent; and (c) dexrazoxane. In some embodiment, the protective agent is myricetin.

DETAILED DESCRIPTION

Certain cancer drugs (e.g., anthracycline drags, protein kinase inhibitors) and other therapies can cause cardiotoxicity in patients. For example, anthracycline-induced cardiotoxicity occurs when the drug such as doxorubicin intercalates the DNA upon a cleavage of DNA by topoisomerase II enzymes thereby effectively preventing TOPOIIα or β from ligating the cleaved strands back together.

This disclosure provides pharmaceutical compositions and methods that may prevent, reduce or eliminate such cardiotoxicity and that may also prevent, reduce or eliminate organ damage caused by cardiac tissue damage, electrophysiological dysfunction, mitochondrial toxicity, apoptosis, or oxidative stress. Many of the compositions and methods provided herein relate to the administration of a specific protective agent in conjunction with one or more cancer treatments, thereby reducing the risk that the cancer treatment will cause or aggravate cardiotoxic events in a patient. The protective agents described herein include such as myricetin, vitexin, robinetin, tricetin, ficetin, 7,3',4',5'-tetrahydroxyflavone, dihydrorobinetin, myricitrin and/or derivatives or salts thereof. In some cases, the protective agents may be flavonoids. In some cases, the protective agent may be administered in combination with a different protective agent. In some cases, the protective agent may be administered in combinations such as combinations including dexrazoxane and another protective agent.

The present disclosure may enable cancer patients— including heart healthy patients and patients with pre-existing cardiac conditions—to receive a desired dosage of a therapy (e.g., an anthracycline or salt thereof) without having the dosage regimen significantly altered by the risk of cardiotoxicity. Another advantage of the present disclosure is that it may enable a larger patient population to receive a given therapy, such as certain patients with pre-existing cardiac conditions or with age limits. In addition, the reduction or prevention of cardiotoxicity may enable a cancer patient to avoid having to take a medication to treat a heart condition. Overall, the advantages presented herein may help to facilitate a better therapeutic outcome for patients.

Figure 2:
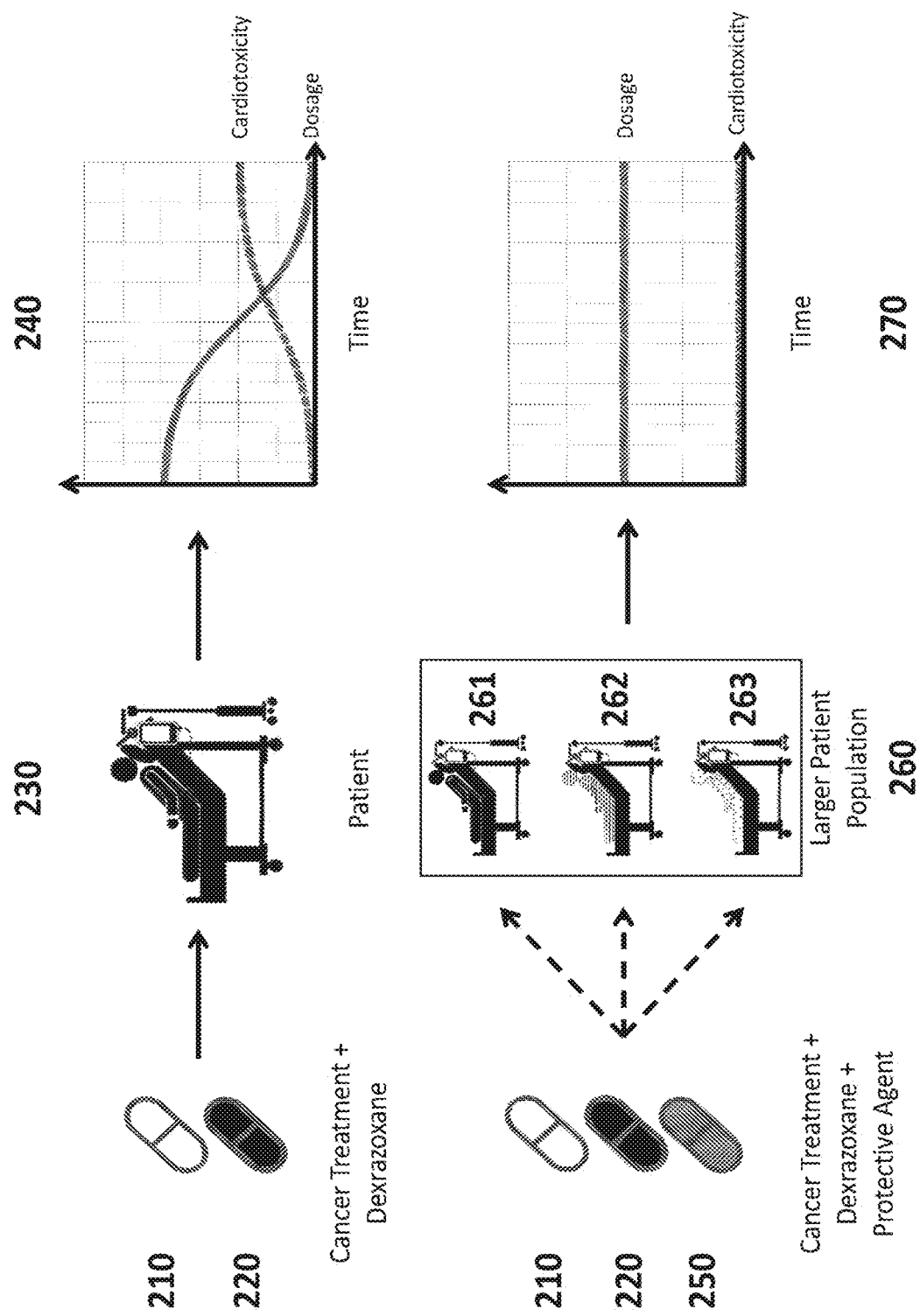
FIG. 2 generally depicts co-administration of a cancer treatment, dexrazoxane (DEX), and a protective agent.

The pharmaceutical compositions and methods (including methods of use) provided herein generally relate to reducing, eliminating or preventing cardiotoxicity caused by chemotherapeutic drugs, biologic agents, or radiation therapy; they can also be used to reduce or eliminate organ damage caused by electrophysiological dysfunction, mitochondrial toxicity, apoptosis, or oxidative stress. FIG. 1 depicts a general schematic of some embodiments of the methods provided herein. The top panel shores a cancer treatment [110], such as a chemotherapeutic drug, biologic agent, or radiation therapy, being administered to a patient [120], who develops cardiotoxicity and is then gradually given reduced doses of the cancer treatment over time [130], Therefore, the cardiotoxicity associated with administration of the cancer treatment [110] in the absence of a protective agent [140] may limit the patient population that is eligible to receive treatment. In the bottom panel, the cancer treatment [110] is co-administered with a protective agent [140], such as myricetin, vitexin, robinetin, tricetin, ficetin, 7,3',4',5'-tetrahydroxyflavone, dihydrorobinetin and myricitrin to a patient, e.g., [151] who experiences reduced cardiotoxicity, or no cardiotoxicity at all [160], thereby enabling the patient to tolerate the dosage regimen. Although separate vehicles for the cancer treatment and protective agent are depicted, in some cases the cancer treatment and protective agent are co-formulated together. The co-administration of the cancer treatment [110] with the protective agent [140] may enable a larger patient population [150] to receive the cancer treatment, including healthy patients and patients with pre-existing cardiac conditions [152, 153], FIG. 2 also depicts a general schematic of embodiments provided herein. The top panel shows a cancer treatment [210] (e.g., a chemotherapeutic drug, a biologic agent, or radiation therapy), and dexrazoxane [220] being co-administered to a patient [230] who then experiences some cardiotoxicity over time [240], The co-administration of the cancer treatment [210] and dexrazoxane [220] in the absence of the protective agent [250] may limit the patient population that is eligible to receive treatment. In the bottom, panel, the cancer treatment [210], the dexrazoxane [220], and a protective agent [250] (such as myricetin, vitexin, robinetin, tricetin, ficetin, 7,3',4', 5'-tetrahydroxyflavone, dihydrorobinetin, and myricitrin) are administered to a patient [261] who experiences reduced cardiotoxicity, or no cardiotoxicity at all [270], In this embodiment, the co-administration of the protective agent [250] with the cancer treatment [210] and dexrazoxane [220] may enhance the activity of dexrazoxane to prevent, alleviate, or eliminate cardiotoxicity in a patient [261], thereby enabling a larger patient population [260] to receive treatment, including patients without and those with pre-existing cardiac conditions [262, 263], In some cases, the protective agent, the dexrazoxane and/or the cancer treatment are administered separately, in some cases, they are administered concurrently or as co-formulations. Generally, the co-formulations and methods provided herein may reduce the cardiotoxicity induced in patients by chemotherapeutic drugs, biologic agents, or radiation therapy.

The compositions provided herein may include a co-formulation of two or more protective agents. For example, the co-formulation may comprise such as myricetin, vitexin, robinetin, tricetin, ficetin, 7,3',4',5'-tetrahydroxyflavone, dihydrorobinetin, myricitrin, and dexrazoxane. In some cases, the compositions may include a co-formulation of a protective agent (e.g., such as myricetin, vitexin, robinetin, tricetin, ficetin, 7,3',4',5'-tetrahydroxyflavone, dihydrorobinetin, and myricitrin) with a certain cancer treatment (e.g., chemotherapeutic drug or biologic agent). In some cases, provided herein are kits that contain at least two protective agents (or a protective agent and a cancer treatment) as separate components, often along with instructions for use.

Methods

Provided herein are methods for administering to a patient, particularly a cancer patient, a pharmaceutical composition that can reduce, eliminate or prevent cardiotoxicity caused by a cancer treatment (e.g., chemotherapeutic drags, biologic agents or radiation therapy). The methods provided herein also comprise treating cancer in a patient using at least one of the compositions provided herein. In some cases, the patient may be heart-healthy; in some cases, the patient is at-risk for a cardiac condition.

The methods provided herein generally comprise administering to a patient a pharmaceutical composition comprising at least one protective agent described herein, or at least one protective agent and a cancer treatment (e.g., anthracycline drug, protein kinase inhibitor, biologic agent, or radiation therapy). The protective agent and cancer treatment may also be combined with a different cardioprotective agent (e.g., dexrazoxane). In some cases, the protective agent and cancer treatment may be co-formulated, in that they are mixed within the same pharmaceutical composition (e.g., tablet, capsule, liposome, liquid, or vapor); in some cases, they exist as distinct entities.

Subjects

The methods and compositions disclosed herein are generally used to prevent, reduce, treat, or eliminate cancer treatment-induced cardiotoxicity in a subject. The subject may be any human patient, particularly a cancer patient, a patient at risk for cancer, or a patient with a family or personal history of cancer. In some cases, the patient is in a particular stage of cancer treatment. For example, a pharmaceutical composition described herein can be administered to a human patient with early or late stage cancer in order to reduce cardiotoxicity caused by a cancer treatment.

The cancer patients may have any type of cancer. Examples of cancer can include, but are not limited to, adrenal cancer, anal cancer, basal cell carcinoma, bile duct cancer, bladder cancer, cancer of the blood, bone cancer, a brain tumor, breast cancer, bronchus cancer, cancer of the cardiovascular system, cervical cancer, colon cancer, colorectal cancer, cancer of the digestive system, cancer of the endocrine system, endometrial cancer, esophageal cancer, eye cancer, gallbladder cancer, a gastrointestinal tumor, kidney cancer, hematopoietic malignancy, laryngeal cancer, leukemia, liver cancer, lung cancer, lymphoma, melanoma, mesothelioma, cancer of the muscular system, Myelodysplastic Syndrome (MDS), myeloma, nasal cavity cancer, nasopharyngeal cancer, cancer of the nervous system, cancer of the lymphatic system, oral cancer, oropharyngeal cancer, osteosarcoma, Kaposi sarcoma, ovarian cancer, pancreatic cancer, penile cancer, pituitary tumors, prostate cancer, rectal cancer, renal pelvis cancer, cancer of the reproductive system, cancer of the respiratory system, sarcoma, salivary gland cancer, skeletal system cancer, skin cancer, small intestine cancer, stomach cancer, testicular cancer, throat cancer, thymus cancer, thyroid cancer, a tumor, cancer of the urinary system, uterine cancer, vaginal cancer, or vulvar cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term 'leukemia' may refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia. In some cases, the cancer patient does not have a particular type of cancer. For example, in some instances, the patient may have a cancer that is not breast cancer.

Examples of cancer include cancers that cause solid tumors as well as cancers that do not cause solid tumors. Furthermore, any of the cancers mentioned herein may be a primary cancer (e.g., a cancer that is named after the part of the body where it first started to grow) or a secondary or metastatic cancer (e.g., a cancer that has originated from another part of the body).

A patient at risk of cancer may be at risk because of a particular condition such as a pre-cancerous condition. Pre-cancerous conditions include but are not limited to actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia). In some cases, a patient may be at risk of cancer because of cell or tissue dysplasia (e.g., an abnormal change in cell number, abnormal change in cell shape, abnormal change in cell size, or abnormal change in cell pigmentation).

A patient at risk of cancer may be a patient that was exposed to a carcinogenic agent. Such patients may include patients with exposure to known or probable carcinogens (e.g., acetyl aldehyde, asbestos, or tobacco products), or patients exposed to ionizing radiation (e.g., gamma radiation, beta-radiation, X-radiation, or ultraviolet radiation). In some cases, a patient at risk of cancer is at risk because of a family history of cancer.

The methods and compositions disclosed herein may also be used to prevent, reduce, or eliminate cardiotoxicity in patients with a history of cancer, particularly patients who have been administered cancer treatments (e.g., anthracycline drugs, protein kinase inhibitors, proteasome inhibitors, or biological agents) with cardiotoxic effects. Examples of a patient with a history of cancer include, but are not limited to, a patient in remission, a patient in complete remission, a patient with relapsed cancer or a patient with recurring cancer.

The methods and compositions disclosed herein are generally used in a patient that has been administered, or is currently being administered, a cardiotoxicity-inducing agent (e.g., a cancer treatment). Non-limiting examples of cardiotoxicity-inducing agents are described elsewhere herein and may include cancer treatments, chemotherapeutic drugs, anthracyclines (e.g., doxorubicin, epirubicin, and idarubicin), protein kinase inhibitors (e.g., tyrosine kinase inhibitor), biologic agents (e.g., trastuzumab), or radiation therapy, as well as any cancer treatment otherwise known to cause cardiotoxicity. In some examples, a pharmaceutical composition disclosed herein is administered to a cancer patient with previous exposure to a cancer treatment known to have cardiotoxic effects, in order to reduce the risk of cardiotoxicity associated with the patient's current cancer treatment regimen. In some cases, the pharmaceutical composition is administered to a cancer patient in order to reduce or off-set cumulative effects of prior exposures to cancer treatment or drugs, or to other agents that cause cardiotoxicity. In some examples, a pharmaceutical co-formulation comprising myricetin and anthracycline may be administered to a prostate cancer patient who also has dilated cardiomyopathy caused by a previous cancer treatment. In another example, a pharmaceutical co-formulation comprising vitexin may be administered to a lung cancer patient who is being concurrently treated with an anthracycline. In yet another example, a pharmaceutical co-formulation comprising robinetin may be administered to a breast cancer patient. In yet another example, a pharmaceutical co-formulation comprising tricetin may be administered to a Kaposi sarcoma cancer patient. In yet another example, a pharmaceutical co-formulation comprising ficetin may be administered to a breast cancer patient. In yet another example, a pharmaceutical co-formulation comprising 7,3',4',5'-tetrahydroxyflavone may be administered to a breast cancer patient. In yet another example, a pharmaceutical co-formulation comprising myricitrin may be administered to a breast cancer patient. In yet another example, a pharmaceutical co-formulation comprising myricetin and anthracycline may be administered to a liver cancer patient who also has dilated cardiomyopathy caused by a previous cancer treatment. In yet another example, a pharmaceutical co-formulation comprising myricetin and doxorubicin may be administered to a sarcoma, cancer patient.

In some cases, the methods and compositions herein may be used to alleviate cardiotoxicity that is not caused by a cancer treatment. As such, the patient may have or be at risk of having, cardiotoxicity induced by a drag that Is not specifically for cancer, such as a protein kinase inhibitor. Such patients may have a condition such as a neurological or cardiac disorder. In some cases, the condition may be a condition treatable by a protein kinase inhibitor.

In some cases, the patient may have organ damage or be at risk of having organ damage. For example, the patient may have organ damage (or be at risk of organ damage) as a result of cardiac tissue damage, electrophysiological dysfunction, mitochondrial toxicity, apoptosis, or oxidative stress. For such patients, the methods and compositions provided herein may reduce or eliminate the organ damage caused by cardiac tissue damage, electrophysiological dysfunction, mitochondrial toxicity, apoptosis, or oxidative stress.

In some cases, patients treated by any of the methods or compositions described herein may have heart disease, or have a family history of heart disease. Examples of heart disease include, but are not limited to, arrhythmogenic cardiomyopathy, arterial disease, Brugada Syndrome, congenital heart disease, dilated cardiomyopathy, heart palpitations, heart valve disease, hypertensive heart disease, hypertrophic cardiomyopathy, long QT syndrome, rheumatic heart disease, or vascular disease. In some cases, the heart disease is caused by a cardiotoxic agent (e.g., anthracycline). For example, the heart disease may be caused by any of the cardiotoxic agents mentioned herein. In one particular example, a pharmaceutical co-formulation comprising myricetin and doxorubicin may be administered to a breast cancer patient who also has hypertrophic cardiomyopathy. In another example, a co-formulation of one or more compound selected from the group consisting of myricetin, vitexin, robinetin, tricetin, ficetin, 7,3',4',5'-tetrahydroxyflavone, dihydrorobinetin, and myricitrin may be administered to a cancer patient experiencing cardiotoxicity from a previously administered chemotherapy drug.

A patient treated by any of the methods or compositions described herein may be of any age and may be an adult, infant or child. In some cases, the patient is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 years old, or within a range therein (e.g., between 2 and 20 years old, between 20 and 40 years old, or between 40 and 90 years old). A particular class of patients that may benefit is patients over the age of 40. Another particular class of patients that may benefit is pediatric patients, who may be at life risk of chronic heart symptoms. Furthermore, a patient treated by any of the methods or compositions described herein may be male or female.

Any of the compositions disclosed herein may also be administered to a non-human subject, such as a laboratory or farm animal. Non-limiting examples of a non-human subject include a dog, a goat, a guinea pig, a hamster, a mouse, a pig, a non-human primate (e.g., a gorilla, an ape, an orangutan, a lemur, or a baboon), a rat, a sheep, a cow, or a zebrafish.

Drug Administration

The disclosure provided herein describes methods to prevent, reduce, or eliminate cancer treatment-induced cardiotoxicity in patients by administering to a patient one or more protective agents of Formula 1, Formula 2 or derivative or salt thereof. The disclosure herein also describes methods to prevent, reduce, or eliminate cancer treatment-induced cardiotoxicity in patients by administering to a patient one or more protective agent selected from the group consisting of myricetin, vitexin, robinetin, tricetin, tricetin, 7,3',4',5'-tetrahydroxyflavone, dihydrorobinetin, and myricitrin (or derivative or salt thereof). The disclosure provided herein also describes methods of administering to a subject, wherein the subject has cancer and the cancer treatment is capable of causing cardiotoxicity and organ damage in the subject, and administering one or more protective agents (or derivative or salt thereof) selected from the group consisting of myricetin, vitexin, robinetin, tricetin, ficetin, 7,3',4',5'-tetrahydroxyflavone, dihydrorobinetin, and myricitrin, wherein the protective agent prevents, reduces, or eliminates the cardiotoxicity in the subject.

Methods disclosed herein can further comprise administering to the patient a combination of dexrazoxane (or derivative or salt thereof) and a protective agent according to Formula 1, Formula 2, or derivative or salt thereof; the combined agents may be administered as a co-formulation or separately. In some aspects, the methods comprise administering to the patient a combination of dexrazoxane (or derivative or salt thereof) and myricetrin (or derivative or salt thereof); the combined agents may be administered as a co-formulation or separately.

Methods disclosed herein can further comprise administering to the patient combined agents comprising a combination of dexrazoxane (or derivative or salt thereof) and a protective agent selected from the group consisting of myricetin, vitexin, robinetin, tricetin, ficetin, 7,3',4',5'-tetrahydroxyflavone, dihydrorobinetin, and myricitrin. (or derivative or salt thereof), the combined agents may be administered as a co-formulation or separately.

The protective agents may be administered to the subject or patient in any combination of a compound of Formula 1 or Formula 2. In some cases, only one protective agent (e.g., myricetin or a derivative or salt thereof) is administered to a subject or patient. In some cases, only one protective agent (e.g., myricitrin or a derivative or salt thereof) is administered to a subject or patient. In some cases, only one protective agent (e.g., vitexin or a derivative or salt thereof) is administered to a subject or patient. In some cases, only one protective agent (e.g., robinetin or a derivative or salt thereof) is administered to a subject or patient. In some cases, only one protective agent (e.g., tricetin or a derivative or salt thereof) is administered to a subject or patient. In some cases, only one protective agent (e.g., 7,3',4',5'-tetrahydroxyflavone or a derivative or salt thereof) is administered to a subject or patient. In a particular example, a subject or patient described herein may be administered a therapeutically effective dose of myricetin (or derivative or salt thereof). In another example, a subject or patient described herein may be administered a therapeutically effective dose of robinetin (or derivative or salt thereof). In yet another example, a subject or patient described herein may be administered a therapeutically effective dose of vitexin (or derivative or salt thereof).

In some cases, two protective agents (or derivative or salt thereof) selected from the group consisting of myricetin, vitexin, robinetin, tricetin, ficetin, 7,3',4',5'-tetrahydroxyflavone, dihydrorobinetin, myricitrin, and dexrazoxane are administered to a subject. In cases where two or more protective agents are administered to a patient, the protective agents may be administered as distinct entities or in a co-formulation. For example, a patient experiencing cardiotoxicity may be administered a therapeutically effective co-formulation of myricetin and robinetin; myricetin and dexrazoxan; or other co-formulation described herein. The two or more protective agents may be administered simultaneously or sequentially. In some cases, the two or more protective agents may be administered sequentially in a particular order. For example, a patient may first be administered myricetin and subsequently administered dexrazoxane, or may first be given dexraxozane and then given myricetin.

In some cases, an anticancer agent (e.g., chemotherapeutic drag, biologic agent, protein kinase inhibitor, radiation therapy) (or other treatment) and one or more protective agents of Formula 1 or Formula 2 (e.g., myricetin, vitexin, robinetin, tricetin, ficetin, 7,3',4',5'-tetrahydroxyflavone, dihydrorobinetin, and myricitrin) may be administered to a patient. In cases where a cancer treatment (or other treatment) and at least two protective agents are administered to a patient, the cancer treatment (or other treatment) and the at least two protective agents (or derivative or salt thereof) may be administered as co-formulations in any combination. For example, a patient may be administered a co-formulation of a protective agent and a chemotherapeutic drug or a co-formulation containing one or more chemotherapeutic drugs and at least two protective agents.

In some cases, a patient or subject may be administered one or more protective agents (or derivative or salt thereof) and one or more cancer treatments (or other treatment) simultaneously. For example, the method may comprise administering to a patient a protective agent and a chemotherapy as separate entities, but simultaneously.

In some cases, a patient or subject may be administered one or more protective agents of Formula 1 or Formula 2 (or derivative or salt thereof) and one or more cancer treatments (or other treatment) sequentially. For example, the protective agent may be administered prior to administration of the cancer treatment (or other treatment). For example, a cancer patient may be administered a therapeutically effective dose of myricetin to prevent cardiotoxicity, and subsequently administered a chemotherapeutic drug (e.g., doxorubicin). In another example, a cancer patient may be administered a therapeutically effective dose of myricitrin to prevent cardiotoxicity, and subsequently administered a chemotherapeutic drug (e.g., doxorubicin). In yet another example, a cancer patient may be administered a therapeutically effective dose of vitexin to prevent cardiotoxicity, and subsequently administered a chemotherapeutic drug (e.g., doxorubicin). In another example, a cancer patient may be administered a therapeutically effective dose of robinetin to prevent cardiotoxicity, and subsequently administered a chemotherapeutic drug (e.g., doxorubicin). In another example, a cancer patient may be administered a therapeutically effective dose of tricetin to prevent cardiotoxicity, and subsequently administered a chemotherapeutic drug (e.g., doxorubicin). In other examples, the cancer treatment (or other treatment) is administered to the patient or subject prior to administration of the protective agent(s) of Formula 1 or Formula 2. In some cases, the patient is administered the one or more protective agents prior to receiving cancer treatment (or other treatment) and then is administered one or more protective agents following the cancer treatment.

In cases of sequential administration, there may be a delay period between administration of the one or more protective agents and the one or more cancer treatments (or other treatments). For example, the protective agent may be administered minutes, hours, days, or weeks prior to administration of a cancer treatment or other treatment (e.g., at least 5 minutes, at least 10 minutes, at least 30 minutes, at least 1 hour, at least 2 hours, at least 3 hours, at least 4 hours, at least 5 hours, at least 6 hours, at least 7 hours, at least 8 hours, at least 9 hours, at least 10 hours, at least 1 day, at least 2 days, at least 3 days, at least 5 days, at least 1 week, at least 2 weeks, at least 3 weeks, at least 4 weeks, at least 2 months, at most 2 months, at most 1 month, at most 3 weeks, at most 2 weeks, at most 1 week, at most 6 days, at most 5 days, at most 4 days, at most 3 days, at most 2 days, at most 1 day, at most 12 hours, at most 6 hours, at most 4 hours, at most 3 hours, at most 2 hours or at most 1 hours prior to administration of the cancer treatment). In some cases, the protective agent has been administered to the patient at least 1 day prior to the cancer treatment. In some cases, the protective agent has been administered at most 1 day prior to the cancer treatment. In some cases, the protective agent is administered at most within 2 hours after the cancer treatment. In some cases, the protective agent is administered at most within 4 hours after the cancer treatment. In some cases, the protective agent is administered at most within 6 hours after the cancer treatment. In some cases, the protective agent is administered at most within 12 hours after the cancer treatment. In some cases, the protective agent is administered at most within 1 day after the cancer treatment. In some cases, the protective agent is administered at most within 2 days after the cancer treatment. In some cases, the protective agent is administered at most within 3 days after the cancer treatment. In some cases, the protective agent is administered at most within 4 days after the cancer treatment. In some cases, the protective agent is administered at most within 5 days after the cancer treatment.

The compounds of the current disclosure (e.g., the protective agents of Formula 1) can be administered to a patient every time the patient is dosed with an anti cancer agent with a dosage regimen described herein. For example, the protective agent may be administered to a patient within 24 hours every time before the patient is scheduled to be dosed with an anticancer agent. In some cases, the protective agent can be administered to a patient within 48 hours every time before the patient is scheduled to dosed with an anticancer agent. In some cases, the protective agent can be administered concurrently to a patient every time the patient is dosed with an anticancer agent. In some cases, the protective agent can be administered to a patient every time the patient has been dosed with an anticancer agent within at least 24 hours following the cancer treatment.

The compounds of the current disclosure may be administered by any of the accepted modes of administration of agents having similar utilities, for example, by cutaneous, oral, topical, intradermal, intrathecal, intravenous, subcutaneous, intramuscular, intra-articular, intraspinal or spinal, nasal, epidural, rectal, vaginal, or transdermal/transmucosal routes. The most suitable route will depend on the nature and severity of the condition being treated. Subcutaneous, intradermal and percutaneous injections can be routes for the compounds of this disclosure. Sublingual administration may be a route of administration for compounds of this disclosure. Intravenous administration may be a route of administration for compounds of this disclosure. In a particular example, the pharmaceutical composition provided herein may be administered to a patient orally. In another particular example, the pharmaceutical composition comprising a protective agent provided herein may be administered to a patient intravenously (via, e.g., injection or infusion). In another particular example, the pharmaceutical composition comprising a protective agent provided herein may be administered to a patient intramuscularly. In a particular example, the pharmaceutical composition comprising a protective agent provided herein may be administered to a patient nasally.

A pharmaceutical composition (e.g., for oral administration or for injection, infusion, subcutaneous delivery, intramuscular delivery, intraperitoneal delivery, sublingual delivery, or other method) may be in the form of a liquid. A liquid pharmaceutical composition may include, for example, one or more of the following: a sterile diluent such as water, saline solution, preferably physiological saline. Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. In another embodiment, for treatment of an ophthalmological condition or disease, a liquid pharmaceutical composition may be applied to the eye in the form of eye drops. A liquid pharmaceutical composition may be delivered orally.

For oral formulations, at least one of the compounds or agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in a pharmaceutical composition may be formulated for oral delivery with a flavoring agent, e.g., in a liquid, solid or semi-solid formulation and/or with an enteric coating. In some cases, the compounds of this disclosure may be solubilized and encapsulated (e.g., in a liposome or a biodegradable polymer), or used in the form of microcrystals coated with an appropriate nontoxic lipid. In some cases, the compounds of this disclosure may be solubilized and encapsulated in a liposome, micelle or the both.

A pharmaceutical composition comprising any one of the compounds or agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

The disclosure provided herein also describes methods for preventing, reducing, or eliminating organ damage in a subject by administering to a patient one or more protective agents of Formula 1 or Formula 2. The protective agent of Formula 1 or Formula 2 for preventing, reducing, or eliminating organ damage in a subject can include without limitation myricetin, vitexin, robinetin, tricetin, ficetin, 7,3', 4',5'-tetrahydroxyflavone, dihydrorobinetin, or myricitrin (or derivative or salt thereof). In particular, the organ damage may be caused by cardiac tissue damage, electrophysiological dysfunction, mitochondrial toxicity, apoptosis, or oxidative stress, leading to heart failure. For example, a pharmaceutical composition comprising a compound of Formula 1 (i.e., protective agent) may be administered to a patient that is experiencing cancer treatment-induced heart failure, wherein further hear failure is prevented by the administration of the pharmaceutical composition.

The pharmaceutical methods and compositions described herein prevent, reduce, or eliminate cancer treatment-induced cardiotoxicity in a patient. Accordingly, the methods and compositions provided herein enable a patient (e.g., a heart-healthy patient, a patient with cardiac disease) to receive a higher dosage of a therapy without having the dosage regimen significantly altered by the risk of cardiotoxicity. In some cases, administering a pharmaceutical composition herein to a patient can comprise administering a daily dose of greater than 0.1 mg/m$^2$, 1 mg/m$^2$, 2 mg/m$^2$, 3 mg/m$^2$, 4 mg/m$^2$, 5 mg/m$^2$, 6 mg/m$^2$, 7 mg/m$^2$, 8 mg/m$^2$, 9 mg/m$^2$, 10 mg/m$^2$, 11 mg/m$^2$, 12 mg/m$^2$, 13 mg/m$^2$, 14 mg/m$^2$, 15 mg/m$^2$, 16 mg/m$^2$, 17 mg/m$^2$, 18 mg/m$^2$, 19 mg/m$^2$, 20 mg/m$^2$, 21 mg/m$^2$, 22 mg/m$^2$, 23 mg/m$^2$, 24 mg/m$^2$, 25 mg/m$^2$, 26 mg/m$^2$, 27 mg/m$^2$, 28 mg/m$^2$, 29 mg/m$^2$, 30 mg/m$^2$, 31 mg/m$^2$, 32 mg/m$^2$, 33 mg/m$^2$, 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 100 mg/m², 150 mg/m², 200 mg/m², 300 mg/m², 350 mg/m², 400 mg/m², 450 mg/m², 500 mg/m², 750 mg/m², 1000 mg/m², 1250 mg/m², 1500 mg/m², 1750 mg/m², or 2000 mg/m² of chemotherapeutic drug; (e.g., anthracycline, doxorubicin or derivative or salt thereof) to a patient.

In some cases, administering a pharmaceutical composition herein to a patient can comprise administering a daily dose of about 0.1 mg/m², 0.2 mg/m², 0.3 mg/m², 0.4 mg/m², 0.5 mg/m², 0.6 mg/m², 0.7 mg/m², 0.8 mg/m², 0.9 mg/m², 1 mg/m², 1.1 mg/m², 1.2 mg/m², 1.3 mg/m², 1.4 mg/m², 1.5 mg/m², 1.6 mg/m², 1.7 mg/m², 1.8 mg/m², 1.9 mg/m², 2 mg/m², 2.1 mg/m², 2.2 mg/m², 2.3 mg/m², 2.4 mg/m², 2.5 mg/m², 2.6 mg/m², 2.7 mg/m², 2.8 mg/m², 2.9 mg/m², 3 mg/m², 3.1 mg/m². 3.2 mg/m², 3.3 mg/m². 3.4 mg/m², 3.5 mg/m², 3.6 mg/m², 3.7 mg/m², 3.8 mg/m², 3.9 mg/m², 4 mg/m², 4.1 mg/m², 4.2 mg/m², 4.3 mg/m², 4.4 mg/m²¹, 4.5 mg/m², 4.6 mg/m², 4.7 mg/m², 4.8 mg/m², 4.9 mg/m², 5 mg/m², 5.1 mg/m², 5.2 mg/m², 5.3 mg/m², 5.4 mg/m², 5.5 mg/m², 5.6 mg/m², 5.7 mg/m², 5.8 mg/m², 5.9 mg/m², 6 mg/m², 6.1 mg/m², 6.2 mg/m², 6.3 mg/m², 6.4 mg/m², 6.5 mg/m², 6.6 mg/m², 6.7 mg/m², 6.8 mg/m², 6.9 mg/m², 7 mg/m², 7.1 mg/m², 7.2 mg/m², 7.3 mg/m², 7.4 mg/m², 7.5 mg/m², 7.6 mg/m², 7.7 mg/m², 7.8 mg/m², 7.9 mg/m², 8 mg/m², 8.1 mg/m², 8.2 mg/m², 8.3 mg/m², 8.4 mg/m², 8.5 mg/m², 8.6 mg/m², 8.7 mg/m², 8.8 mg/m², 8.9 mg/m², 9 mg/m², 9.1 mg/m², 9.2 mg/m², 9.3 mg/m², 9.4 mg/m², 9.5 mg/m², 9.6 mg/m², 9.7 mg/m², 9.8 mg/m², 9.9 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/m², 54 mg/m², 55 mg/m², 56 mg/m², 57 mg/m², 58 mg/m², 59 mg/m², 60 mg/m², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 91 mg/m², 92 mg/m², 93 mg/m², 94 mg/m², 95 mg/m², 96 mg/m², 97 mg/m², 98 mg/m², 99 mg/m², or 100 mg/m² of a biologic agent to a patient.

In some cases, administering a pharmaceutical composition herein to a patient can comprise administering a daily dose of about 0.1 mg/m², 1 mg/m², 2 mg/m², 3 mg/m², 4 mg/m², 5 mg/m², 6 mg/m², 7 mg/m², 8 mg/m², 9 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/rn², 54 mg/m², 55 mg/m², 56 mg/m², 57 mg/m², 58 mg/m², 59 mg/m², 60 mg/rn², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 90 mg/m², 95 mg/m², 100 mg/m², 110 mg/m², 120 mg/m², 130 mg/m², 140 mg/m², 150 mg/m², 160 mg/m², 170 mg/m², 180 mg/m², 190 mg/m², 200 mg/m², 300 mg/m², 400 mg/m², 500 mg/m² of the protective agent drug; of Formula 1 or Formula 2 (e.g., myricetin, vitexin, robinetin, tricetin, ficetin, 7,3',4',5'-tetrahydroxyflavone, dihydrorobinetin, myricitrin and/or a derivative or salt thereof).

The daily fixed dose of protective agent described herein, or collective dose of a combination of protective agents can be greater than 0.1 mg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 150 mg, 200 mg, 300 mg, 350 mg, 400 mg, 450 mg, 500 mg, 750 mg or higher of the protective agent (or any derivative or salt thereof). In some cases, the protective agent or agents is selected from the group consisting of myricetin, vitexin, robinetin, tricetin, ficetin, 7,3',4',5'-tetrahydroxyflavone, dihydrorobinetin, myricitrin and/or a derivative or salt thereof. In a particular example, administering a pharmaceutical composition to a patient can comprise administering a co-formulation of a chemotherapy drug (e.g., doxorubicin) with at least 10 mg of myricetin. In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 2.1 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of myricetin (or any derivative or salt thereof) to a patient.

In another example, administering a pharmaceutical composition to a patient can comprise administering a co-formulation of a chemotherapy drug (e.g., doxorubicin) with at least 10 mg of myricetrin. In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of myricetrin (or any derivative or salt thereof) to a patient.

In yet another example, administering a pharmaceutical composition to a patient can comprise administering a co-formulation of a chemotherapy drug (e.g., doxorubicin) with at least 10 mg of vitexin. In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of vitexin (or any derivative or salt thereof) to a patient.

In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of robinetin (or any derivative or salt thereof).

In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of tricetin (or any derivative or salt thereof).

In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or 1 g of 7,3',4',5'-tetrahydroxyflavone (or any derivative or salt thereof).

In some cases, administering a pharmaceutical composition herein to a patient can comprise administering a daily dose of 0.1 mg, 0.2 mg, 0.3 mg, 0.4 mg, 0.5 mg, 0.6 mg, 0.7 mg, 0.8 mg, 0.9 mg, 1 mg, 1.1 mg, 1.2 mg, 1.3 mg, 1.4 mg, 1.5 mg, 1.6 mg, 1.7 mg, 1.8 mg, 1.9 mg, 2 mg, 2.1 mg, 2.2 mg, 2.3 mg, 2.4 mg, 2.5 mg, 2.6 mg, 2.7 mg, 2.8 mg, 2.9 mg, 3 mg, 3.1 mg, 3.2 mg, 3.3 mg, 3.4 mg, 3.5 mg, 3.6 mg, 3.7 mg, 3.8 mg, 3.9 mg, 4 mg, 4.1 mg, 4.2 mg, 4.3 mg, 4.4 mg, 4.5 mg, 4.6 mg, 4.7 mg, 4.8 mg, 4.9 mg, 5 mg, 5.1 mg, 5.2 mg, 5.3 mg, 5.4 mg, 5.5 mg, 5.6 mg, 5.7 mg, 5.8 mg, 5.9 mg, 6 mg, 6.1 mg, 6.2 mg, 6.3 mg, 6.4 mg, 6.5 mg, 6.6 mg, 6.7 mg, 6.8 mg, 6.9 mg, 7 mg, 7.1 mg, 7.2 mg, 7.3 mg, 7.4 mg, 7.5 mg, 7.6 mg, 7.7 mg, 7.8 mg, 7.9 mg, 8 mg, 8.1 mg, 8.2 mg, 8.3 mg, 8.4 mg, 8.5 mg, 8.6 mg, 8.7 mg, 8.8 mg, 8.9 mg, 9 mg, 9.1 mg, 9.2 mg, 9.3 mg, 9.4 mg, 9.5 mg, 9.6 mg, 9.7 mg, 9.8 mg, 9.9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 100 mg, 500 mg, 750 mg, or Ig of ficetin (or any derivative or salt thereof).

The pharmaceutical methods and compositions described herein prevent, reduce, or eliminate cancer treatment-induced cardiotoxicity in a patient. Accordingly, the methods and compositions provided herein enable a patient to receive a therapy more frequently without having the dosage regimen significantly altered by the risk of cardiotoxicity. The daily dose of a chemotherapeutic drug, biologic agent or protective agent within the pharmaceutical composition provided herein may be administered to a patient in one or more doses pier day. In some cases, the daily dose of the chemotherapeutic drug may be administered in a single dose. In some cases, the daily dose of the chemotherapeutic drug may be divided into 1, 2, 3, 4, 5, 6, 7, 8, 9, or 10 doses per day. For example, the daily dose of chemotherapeutic drug (e.g., doxorubicin) can be divided into 3 doses per day. In some cases, the daily dose of the chemotherapeutic drug may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a chemotherapeutic drug may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours. In some cases, the daily dose of the biologic agent may be administered in a single dose. In some cases, the daily dose of the biologic agent may be divided into 1, 2, 3, 4, 5, 6, 7, 8, 9, 10, 11, 12, 13, 14, 15, 16, 17, 18, 19, 20, 21, 22, 23, or 24 doses per day. For example, the daily dose of biologic agent (e.g., bevacizumab) can be divided into 3 doses per day. In some cases, the daily dose of the biologic agent may be divided into at least 1, 2, 3, 4, 5, 6, 7, 8, 9, 10, 15, 20, 25, 30, 35, 40, 45, 50, 55, or 60 infusions per hour. In some cases, each infusion of a composition comprising a biologic agent may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours. In some cases, the daily dose of the protective agent may be administered in a single dose. In some cases, the daily dose of the protective agent may be divided into 1, 2, 3, 4, 5, 6, 7, 8, 9, 10, 11, 12, 13, 14, 15, 16, 17, 18, 19, 20, 21, 22, 23, or 24 doses per day. For example, the daily dose of protective agent (e.g., myricetin) can be divided into 3 doses per day. In some cases, the daily dose of the protective agent may be divided into at least 1, 2, 3, 4, 5, or 6 infusions per hour. In some cases, each infusion of a composition comprising one or more protective agent(s) may last for at least 5 minutes, 10 minutes, 15 minutes, 20 minutes, 25 minutes, 30 minutes, 35 minutes, 40 minutes, 45 minutes, 50 minutes, 55 minutes, 1 hour, 1.5 hours, 2 hours, 2.5 hours, 3 hours, 3.5 hours, 4 hours, 4.5 hours, 5 hours, 5.5 hours, or 6 hours.

The pharmaceutical compositions described herein may be administered to a patient one or more times per day. In some cases, the pharmaceutical composition may be administered to a patient one time per day. In some cases, the pharmaceutical composition may be administered to a patient at least 2 times, 3 times, 4 times 5 times, 6 times, 7 times, 8 times, 9 times, 10 times, 11 times, 12 times, 13 times, 14 times, 15 times, 16 times, 17 times, 18 times, 19 times, 20 times, 21 times, 22 times, 23 times, or 24 times per day. For example, a pharmaceutical composition may be administered to a patient 3 times per day.

The pharmaceutical compositions described herein may be administered to a patient for one or more days. In some cases, the pharmaceutical composition may be administered to a patient for one day. In some cases, the pharmaceutical composition may be administered to the patient for at least 2 days, 3 days, 4 days, 5 days, 6 days, 1 week, 2 weeks, 3 weeks, 1 month, 2 months, 3 months, 4 months, 5 months, 6 months, 7 months, 8 months, 9 months, 10 months, 11 months, 1 year, 2 years, 3 years, 4 years, 5 years, 6 years, 7 years, 8 years, 9 years, 10 years, 20 years, 30 years, 40 years, or 50 years. For example, a cancer patient may be administered a pharmaceutical co-formulation of doxorubicin and myricetin for a period of at least 1 year. In some cases, the pharmaceutical composition may be administered to a patient for two or more consecutive days. In some cases, the pharmaceutical composition may be administered to a patient for two or more non-consecutive days. For example, a patient may be administered a pharmaceutical composition every day, consecutively, for 4 days. In another example, a patient may be administered a pharmaceutical composition on day 1, day 3, day 7, and day 15. In some cases, when a patient is administered a pharmaceutical composition over a period of time, the dosage amount administered to the patient on one day can be different from the dosage amount administered to the patient on a subsequent day. For example, a patient may be administered 5 mg of a pharmaceutical composition on the first day, and administered 10 mg of a pharmaceutical composition on a subsequent day.

The pharmaceutical compositions described herein may be effective over time. In some cases, the pharmaceutical composition may be effective for one or more days. In some cases, the duration of efficacy of the pharmaceutical composition is over a long period of time. In some cases, the efficacy of the pharmaceutical composition may be greater than 2 days, 3 days, 4 days, 5 days, 6 days. 1 week, 2 weeks, 3 weeks, or 1 month.

Methods provided herein can further comprise administering to the patient dexrazoxane (or any derivative or salt thereof) as part of any of the pharmaceutical compositions described herein. Such methods allow for the administration to a patient a pharmaceutical composition containing at least one protective agent and dexrazoxane, wherein the co-formulation of at least one protective agent and dexrazoxane can provide a greater protective effect as compared to the administration of dexrazoxane alone. In some cases, the administration of any of the pharmaceutical compositions described herein can reduce the likelihood of cardiotoxicity across a patient pool by as much as 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83% o, 84%, 85%, 86%, 87%, 88%, 89%, 90%, 91%, 92%, 93%, 94%, 95%, 96%, 97%, 98%, 99% or 100%. For example, if there is an 80% likelihood that patients in a patient pool that are administered dexrazoxane will experience cardiotoxicity, administering to the patients a co-formulation of myricetin and dexrazoxane can reduce the likelihood of experiencing cardiotoxicity by 75%, resulting in a 20% likelihood that the patients will experience cardiotoxicity. This greater protective effect may also enable a larger population of patients, including those with pre-existing cardiac conditions, to receive a cancer treatment (e.g., doxorubicin) to which they would otherwise be precluded. In some cases, the dexrazoxane may be co-formulated within the pharmaceutical composition, in that it is mixed within the pharmaceutical composition, or exist as a distinct entity. In some cases, the cancer treatment, protective agent, and dexrazoxane may be administered concurrently. In some cases, the cancer treatment, protective agent, and dexrazoxane may be administered sequentially. In one example, a cancer patient may be administered a co-formulation of chemotherapeutic drug, dexrazoxane, and myricetin in a single dose at least one time per day. In another example, a cancer patient may be administered dexrazoxane, and subsequently administered myricetin.

The dose of dexrazoxane (or any derivative or salt thereof) administered within the pharmaceutical composition can be greater than 0.1 mg/m², 1 mg/m², 2 mg/m², 3 mg/m², 4 mg/m², 5 mg/m², 6 mg/m², 7 mg/m², 8 mg/m², 9 mg/m², 10 mg/m², 11 mg/m², 12 mg/m², 13 mg/m², 14 mg/m², 15 mg/m², 16 mg/m², 17 mg/m², 18 mg/m², 19 mg/m², 20 mg/m², 21 mg/m², 22 mg/m², 23 mg/m², 24 mg/m², 25 mg/m², 26 mg/m², 27 mg/m², 28 mg/m², 29 mg/m², 30 mg/m², 31 mg/m², 32 mg/m², 33 mg/m², 34 mg/m², 35 mg/m², 36 mg/m², 37 mg/m², 38 mg/m², 39 mg/m², 40 mg/m², 41 mg/m², 42 mg/m², 43 mg/m², 44 mg/m², 45 mg/m², 46 mg/m², 47 mg/m², 48 mg/m², 49 mg/m², 50 mg/m², 51 mg/m², 52 mg/m², 53 mg/m², 54 mg/m², 55 mg/m², 56 mg/m², 57 mg/m², 58 mg/m², 59 mg/m², 60 mg/m², 61 mg/m², 62 mg/m², 63 mg/m², 64 mg/m², 65 mg/m², 66 mg/m², 67 mg/m², 68 mg/m², 69 mg/m², 70 mg/m², 71 mg/m², 72 mg/m², 73 mg/m², 74 mg/m², 75 mg/m², 76 mg/m², 77 mg/m², 78 mg/m², 79 mg/m², 80 mg/m², 81 mg/m², 82 mg/m², 83 mg/m², 84 mg/m², 85 mg/m², 86 mg/m², 87 mg/m², 88 mg/m², 89 mg/m², 90 mg/m², 91 mg/m², 92 mg/m², 93 mg/m², 94 mg/m², 95 mg/m², 96 mg/m², 97 mg/m², 98 mg/m², 99 mg/m², 100 mg/m², 150 mg/m², 200 mg/m², 300 mg/m², 350 mg/m², 400 mg/m², 450 mg/m², 500 mg/m², 750 mg/m², 1 g/m², 5 g/m², 10 g/m², or higher. In a particular example, administering a pharmaceutical composition to a patient can comprise administering a co-formulation of a protective agent of Formula 1 or Formula 2 (e.g., myricetin) with 50 mg/m² of dexrazoxane.

In some cases, administering a pharmaceutical composition described herein to a patient can comprise administering a dose of about 0.1 mg/kg, 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 51 mg/kg, 52 mg/kg, 53 mg/kg, 54 mg/kg, 55 mg/kg, 56 mg/kg, 57 mg/kg, 58 mg/kg, 59 mg/kg, 60 mg/kg, 61 mg/kg, 62 mg/kg, 63 mg/kg, 64 mg/kg, 65 mg/kg, 66 mg/kg, 67 mg/kg, 68 mg/kg, 69 mg/kg, 70 mg/kg, 71 mg/kg, 72 mg/kg, 73 mg/kg, 74 mg/kg, 75 mg/kg, 76 mg/kg, 77 mg/kg, 78 mg/kg, 79 mg/kg, 80 mg/kg, 81 mg/kg, 82 mg/kg, 83 mg/kg, 84 mg/kg, 85 mg/kg, 86 mg/kg, 87 mg/kg, 88 mg/kg, 89 mg/kg, 90 mg/kg, 90 mg/kg, 95 mg/kg, 100 mg/kg, 110 mg/kg, 120 mg/kg, 130 mg/kg, 140 mg/kg, 150 mg/kg, 160 mg/kg, 170 mg/kg, 180 mg/kg, 190 mg/kg, 200 mg/kg, 300 mg/kg, 400 mg/kg, 500 mg/kg of a protective agent of Formula 1 or Formula 2. In some aspects, the protective agent can be selected from the group consisting of myricetin, vitexin, robinetin, tricetin, ficetin, 7,3',4',5'-tetrahydroxyflavone, dihydrorobinetin, myricitrin and a derivative or salt thereof. In one embodiment, the patient is administered intravenously with a protective agent at 0.5 mg/kg, 1 mg/kg, 1.5 mg/kg, 2 mg/kg, 2.5 mg/kg, 3 mg/kg, 3.5 mg/kg, 4 mg/kg, 4.5 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, 50 mg/kg, 60 mg/kg, 70 mg/kg, 80 mg/kg, 90 mg/kg, or 100 mg/kg, 150 mg/kg, or 200 mg/kg. In one embodiment, the patient is administered with myricetin at a dose between about 0.5 mg/kg and about 50 mg/kg at least 10 minutes before administering an anthracycline (e.g., doxorubicin, epirubicin, or idarubicin). In one embodiment, the patient is administered with myricetin at a dose between about 0.5 mg/k and about 100 mg/kg at least 10 minutes before administering an anthracycline (e.g., doxorubicin, epirubicin, or idarubicin). In one embodiment, the patient is administered intravenously with myricetin at a dose between about 0.5 mg/kg and about 200 mg/kg at least 30 minutes prior to the administration of an anthracycline (e.g., doxorubicin, epirubicin, or idarubicin). In one embodiment, the patient is administered intravenously with myricetin at a dose between about 0.5 mg/kg and about 200 mg/kg at least 1 hour prior to the administration of an anthracycline (e.g., doxorubicin, epirubicin, or idarubicin). In one embodiment, the patient is administered intravenously with myricetin at a dose between about 0.5 mg/kg and about 200 mg/kg of myricetin at least 2 hours before the administration of an anthracycline (e.g., doxorubicin, epirubicin, or idarubicin). In one embodiment, the patient is administered intravenously with a dose between about 0.5 mg/kg and about 200 mg/kg of myricetin at least 4 hours prior to the administration of an anthracycline (e.g., doxorubicin, epirubicin, or idarubicin). In one embodiment, the patient is administered intravenously with myricetin at a dose between about 0.5 mg/kg and about 200 mg/kg of myricetin at least 6 hours before the administration of an anthracycline (e.g., doxorubicin, epirubicin, or idarubicin). In one embodiment, the patient is administered intravenously with myricetin at a dose between about 0.5 mg/kg and about 200 mg/kg of myricetin within 6 hours after the administration of an anthracycline (e.g., doxorubicin, epirubicin, or idarubicin). In one embodiment, myricetin is administered orally at a dose between 0.5 mg/kg and 200 mg/kg at least 0.5, 1, 2, 3, 4, 5, or 6 hour(s) prior to the administration of an anthracycline (e.g., doxorubicin, epirubicin, or idarubicin).

In some aspects, the patient is administered, for example, intravenously or orally with a protective agent (e.g., myricetin, vitexin, robinetin, tricetin, ficetin, 7,3',4',5'-tetrahydroxyflavone, dihydrorobinetin, or myricitrin) at a dose between about 0.5 mg/kg and about 200 mg/kg at least 4 hours prior to the first administration of an anthracycline (e.g., doxorubicin, epirubicin, or idarubicin) after the patient has been diagnosed with cancer.

Patient Response

The methods and compositions provided herein prevent, reduce, or eliminate cardiotoxicity in a patient caused by chemotherapeutic drugs, biologic agents, or radiation therapy. Furthermore, administering to a patient a pharmaceutical composition disclosed herein may also prevent, reduce or eliminate cancer treatment-induced organ damage (e.g., organ damage caused by cardiac tissue damage, electrophysiological dysfunction, mitochondrial toxicity, apoptosis, or oxidative stress).

The methods and compositions disclosed herein may generally reduce cardiotoxicity in a patient. Examples of cardiotoxicity can include, but are not limited to, mitochondrial toxicity, apoptosis, electrophysiological dysfunction (e.g., QT prolongation), mechanical dysfunction (e.g., reduced cardiac ejection fraction), oxidative stress, cardiac tissue damage (e.g., damage caused by oxidative stress, mitochondrial damage, or damage caused by an increase in the flux of reactive oxygen species), and cytotoxic injury to any organ (e.g., liver, kidney, or pancreas) that is not the heart.

Mitochondrial toxicity can refer to any damage that decreases the number of the active mitochondria within a given cell, tissue, organ, or organism. In some cases, mitochondrial toxicity can be measured using an in vitro assay. One such method that can be used for measuring mitochondrial toxicity is by co-exposing cells to (1) a cell-permeable fluorescent dye that indicates cellular nuclei, and (2) tetramethylrhodamine methyl ester (TMRM), a cell-permeable fluorescent dye that is sequestered by active mitochondria.

Mitochondrial toxicity can be calculated as the fraction of TMRM-positive cells to the total number of cell nuclei. As measured by the in vitro assay, cancer treatment-induced mitochondrial toxicity may be greater than 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% in cardiomyocytes, as compared to untreated controls. For example, exposing cardiomyocytes to 1 micromolar of doxorubicin for at least 48 hours can cause 100% mitochondrial toxicity, as compared to untreated control. The pharmaceutical methods and compositions described herein generally reduce cancer treatment-induced mitochondrial toxicity. As measured by the in vitro assay, exposing cardiomyocytes to any of the pharmaceutical compositions described herein can reduce mitochondrial toxicity as much as 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% as compared to cardiomyocytes exposed to a cancer treatment in the absence of a protective agent. For example, exposing cardiomyocytes to a co-formulation of 1 micromolar doxorubicin and 115 micromolar of myricetin for at least 48 hours can reduce mitochondrial toxicity by 30%, as compared to cardiomyocytes exposed to 1 micromolar of doxorubicin.

Apoptosis can refer to a process by which a cell undergoes programmed cell death. Detectable changes within a cell undergoing apoptosis include, but are not limited to, the translocation of cytochrome C from the mitochondria, diminished mitochondrial function, changes in membrane structure, increased proteolytic activity, and DNA fragmentation. In some cases, apoptosis can be measured using an in vitro assay. One such method that can be used for measuring apoptosis is by co-exposing cells to (1) a cell-permeable fluorescent dye that indicates cellular nuclei, and (2) CellEvent Caspase 3/7 Detection Reagent, a fluorogenic substrate for the activated caspase 3 that is uniquely present in apoptotic cells. Percentage apoptosis can be calculated as the fraction of CellEvent-positive cells to the total number of cell nuclei. As measured by the in vitro assay, cancer treatment-induced apoptosis may be greater than 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% in cardiomyocytes, as compared to untreated controls. For example, exposing cardiomyocytes to 1 micromolar of doxorubicin for at least 48 hours can cause 100% apoptosis, as compared to untreated control.

The pharmaceutical methods and compositions described herein may generally reduce cancer treatment-induced apoptosis. As measured by the in vitro assay, exposing cardiomyocytes to any of the pharmaceutical compositions described herein can reduce apoptosis as much as 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% as compared to cardiomyocytes exposed to a cancer treatment in the absence of a protective agent. For example, exposing cardiomyocytes to a co-formulation of 1 micromolar doxorubicin and 115 micromolar of myricetin for at least 48 hours can reduce mitochondrial toxicity by 30%, as compared to cardiomyocytes exposed to 1 micromolar doxorubicin.

Electrophysiological dysfunction can refer to any damage wherein the flow of ions through a biological tissue is disrupted. For example, administering to a cancer patient a chemotherapeutic drug (e.g., doxorubicin) may cause an acute myocardial infarction, wherein ions can no longer flow through the damaged cardiac tissue resulting in a conduction block. In some cases, electrophysiological dysfunction can comprise prolongation of the QT interval, and can be measured using an in vivo assay. The QT interval can be used to describe the time between the start, of the Q wave and the end of the T wave in an electrocardiogram. QT prolongation may Indicate delayed ventricular repolarization, and can predispose the heart to early after-depolarizations (EADs) leading to re-entrant arrhythmia (e.g., Torsades de Pointes). A QT interval may also depend on the length of the cardiac cycle (RR), the amount of time between the onset of one QRS complex and the onset of the next QRS complex. A corrected QT (QTc) interval may be used to represent a QT interval that has been corrected to account for the cycle length. Bazett's formula ($QTc=QT/\sqrt{RR}$), Fridericia's formula ($QTc=QT/\sqrt[3]{RR}$), or a regression analysis method ($QTc=QT+0.154(1-RR)$) may all be used to calculate the QTc interval from the QT interval.

Administration of a chemotherapeutic drug, biologic agent, or radiation therapy to a patient may cause QTc prolongation, above the baseline QTc interval of the patient, in the absence of a protective agent. The baseline QTc interval for a patient is the QTc interval measured in the patient prior to the administration of any drag. For example, administering to a patient a chemotherapeutic drug (e.g., doxorubicin) in the absence of a protective agent can cause a QTc prolongation of 40 milliseconds (ms) above the baseline QTc interval for the patient. In some cases, administration of a chemotherapeutic drug, biologic agent, or radiation therapy to a patient, particularly in the absence of a protective agent, may cause a QTc prolongation of at least 1 ms, 2 ms, 3 ms, 4 ms, 5 ms, 6 ms, 7 ms, 8 ms, 9 ms, 10 ms, 15 ms, 20 ms, 25 ms, 30 ms, 35 ms, 40 ms, 45 ms, 50 ms, 55 ms, 60 ms, 65 ms, 70 ms, 75 ms, 80 ms, 85 ms, 90 ms, 95 ms, or 100 ms above the baseline QTc interval of the patient.

Administration of any of the pharmaceutical compositions described herein can limit the cancer treatment-induced QTc prolongation experienced by the patient, above the baseline QTc interval of the patient. For example, administering to a patient a co-formulation of a chemotherapeutic drug (e.g., doxorubicin) and a protective agent (e.g., myricetin) can cause a QTC prolongation of less than 5 ms. In some cases, the pharmaceutical compositions described herein can cause less than a 100 ms, 95 ms, 90 ms, 85 ms, 80 ms, 75 ms, 70 ms, 65 ms, 60 ms, 55 ms, 50 ms, 45 ms, 40 ms, 35 ms, 30 ms, 25 ms, 20 ms, 15 ms, 10 ms, 9 ms, 8 ms, 7 ms, 6 ms, 5 ms, 4 ms, 3 ms, 2 ms, or 1 ms increase in QTc prolongation above the baseline QTc interval of the patient.

In some cases, electrophysiological dysfunction can also comprise diminished electrical activity, and can be measured using an in vitro assay. Multi electrode arrays (MEAs) are devices that contain multiple planar conductive electrodes on which cells (e.g., cardiomyocytes) may be contacted. Although the size and shape of the electrical recording measured from an MEA can depend on several factors (e.g., cell homogeneity, contact between the cell and an electrode, geometry of an MEA), temporal changes can be measured by the electrode to provide information on the electrical activity of the contacting cells (e.g., percentage of active electrodes, field potential duration, and beat rate).

Exposing cardiomyocytes to a chemotherapeutic drug, biologic agent, or radiation therapy, in the absence of a protective agent, may cause a temporal decrease in the percentage of active electrodes (e.g., an electrode that is able to measure some electrical activity from the contacting cell), as measured by the in vitro assay. For example, exposing cardiomyocytes to 1 micromolar of doxorubicin for at least 24 hours can cause a 50% decrease in the number of active electrodes, as compared to time zero. In some cases, exposing cardiomyocytes to a cancer treatment (e.g., doxorubicin) in the absence of a protective agent (e.g., myricetin) can cause as much as a 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 16%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1% reduction in the number of active electrodes, as measured by the in vitro assay. In a particular example, exposing cardiomyocytes to 1 µM doxorubicin for at least 24 hours can cause as much as a 50% reduction in the number of active electrodes.

The pharmaceutical methods and compositions described herein generally reduce cancer treatment-induced electrophysiological dysfunction (e.g., decrease in the number of active electrodes). As measured by the in vitro assay, exposing cardiomyocytes to any of the pharmaceutical compositions described herein may induce less than a 1%, 2%, 3%, 4%, 5%, 6%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% decrease in the number of active electrodes, as compared to cardiomyocytes exposed to a cancer treatment in the absence of a protective agent. For example, exposing cardiomyocytes to a co-formulation of 1 µM doxorubicin and 100 µM myricetin for at least 24 hours can induce less than a 5% decrease in the number of active electrodes.

The pharmaceutical methods and compositions described herein generally reduce the risk that the patient will experience cardiotoxicity with the administration of a cancer treatment. In some cases, the pharmaceutical methods and compositions described herein can reduce the risk of cardiotoxicity in the patient by 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 9%, 8%, 7%, 6%, 5%, 4%, 3%, 2%, or 1%. In some cases, the pharmaceutical methods and compositions disclosed herein may reduce the risk of cardiotoxicity in the patient by greater than 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. For example, if a patient has a 90% risk for experiencing QT prolongation when administered a chemotherapeutic drug (e.g., doxorubicin, epirubicin, or idarubicin) in the absence of a protective agent (e.g., myricetin, vitexin, robinetin, tricetin, ficetin, 7,3',4',5'-tetrahydroxyflavone, myricitrin and/or a derivative or salt thereof), the patient may experience a 50% reduction of risk for QT prolongation when the protective agent is administered separately or as a co-formulation with a chemotherapeutic drug, resulting in a 45% risk for QT prolongation in the patient. For example, in one particularly embodiment, the patient is administered intravenously with a protective agent (e.g., myricetin, vitexin, robinetin, tricetin, ficetin, 7,3',4',5'-tetrahydroxyflavone, myricitrin and/or a derivative or salt thereof) at a dose between about 0.5 mg/kg and about 100 mg/kg at least 30 minute, 1 hour, 2 hours, 3 hours, 4 hours, 5 hours, or 6 hours prior to the administration of chemotherapeutic drug (e.g., doxorubicin, epirubicin, or idarubicin), wherein the risk for QT prolongation is reduced by at least 30%, 40%, 50%, 60%, 70%, 80%, or 90% as compared to that of control that did not receive the protective agent.

The effect of anthracycline-induced cardiotoxicity on contractility can be also assessed by measuring fractional shortening (FS) and ejection fraction (EF) which are indices of systolic function. An anthracycline such as doxorubicin can have a profound impact on contractile properties. However, a patient administered with a protective agent of Formula 1 or Formula 2 (e.g., myricetin, vitexin, robinetin, tricetin, ficetin, 7,3',4',5'-tetrahydroxyflavone, dihydrorobinetin, myricitrin and/or a derivative or salt thereof) can experience significantly reduced, e.g., doxorubicin-induced cardiotoxicity as observed by marked improvements in FS and EF. For example, myricetin can rescue anthracycline-induced FS and EF dysfunction by at least 30%, 40%, 50%, 60%, 70%, 80%, 90% in the patient as compared to a control group that has been treated with anthracycline, but not dosed with the protective agent.

The term "about" when referring to a number or a numerical range means that the number or numerical range referred to is an approximation within experimental variability (or within statistical experimental error), and thus the number or numerical range may vary from, for example, between 1% and 10% of the stated number or numerical range.

The term "therapeutically effective amount" may generally refer to the amount (or dose) of a compound or other therapy that is minimally sufficient to prevent, reduce, treat or eliminate a condition, or risk thereof, when administered to a subject in need of such compound or other therapy. In some instances, the term "therapeutically effective amount" may refer to that amount of compound or other therapy that is sufficient to have a prophylactic effect when administered to a subject. The therapeutically effective amount may vary; for example, it may vary depending upon the subject's condition, the weight and age of the subject, the severity of the disease condition, the manner of administration and the like, all of which may be determined by one of ordinary skill in the art.

Compositions

The pharmaceutical compositions disclosed herein may comprise a protective agent disclosed in Formula 1 or Formula 2 (e.g., myricetin, vitexin, robinetin, tricetin, ficetin, 7,3',4',5'-tetrahydroxyflavone, dihydrorobinetin, myricitrin and/or a derivative or salt thereof). The pharmaceutical composition may comprise one or more protective agents in any combination, two or more agents in any combination, three or more protective agents in any combination, or four or more protective agents in any combination. In some cases, the pharmaceutical composition can be a co-formulation of at least two protective agents (e.g., myricetin, vitexin, robinetin, tricetin, ficetin, 7,3',4',5'-tetrahydroxyflavone, myricetin (myricitrin), dexrazoxane, and/or a derivative or salt thereof), or a co-formulation of at least one protective agent and a cancer treatment (e.g., chemotherapeutic drug, biologic agent, protein kinase inhibitor or radiation therapy). The protective agents within the pharmaceutical composition may reduce, eliminate or prevent cardiotoxicity induced by the cancer treatment. Additionally, the protective agents within the pharmaceutical composition may also reduce, eliminate or prevent organ damage induced by the cancer treatment. In one example, this disclosure provides a co-formulation comprising myricetin and dexrazoxane. In another example, this disclosure provides a co-formulation comprising the chemotherapeutic drug doxorubicin and myricetin.

In some cases, at least one of the protective agents in the composition may be a flavonoid, or a derivative thereof. Generally, a flavonoid may be any compound with a 15-carbon skeleton backbone consisting of two phenyl and one heterocyclic ring. Flavonoids may belong to any of the following classes of compounds including, but not limited to, anthroxanthins, flavanones, flavonols, flavanonols, flavans, anthocyanadins, bioflavonoids, isoflavonoids, isoflavones, isoflavanes, isoflavandiols, isoflavenes, or neoflavonoids. Non-limiting examples of flavonoids include ayanin, carlinoside, dihydrodaidzein, dihydroobavatin, irigenin, isoanhydroicaritin, isokurarinone, isoxanthohumol, gardenin, lupiwighteone, methoxypuerarin, mirificin, myricetin, myricetrin (myricitrin), dihydromyricetin, pyrroside, kaempferol, quercetin, swertisin, syzalterin, tricetin, ficetin, robinetin, dihydrorobinetin, 7,3',4',5'-tetrahydoxylflavone, 5,7,3',4',5'-pentahydoxyflavone or thevetiaflavone. In one example, a pharmaceutical composition disclosed herein may comprise the flavone such as 7,3',4',5'-tetrahyodxyflavone and tricetin. In another example, a pharmaceutical composition disclosed herein may comprise the flavonol such as myricetin, ficetin, robinetin, quercetin and kaempferol. In another example, a pharmaceutical composition disclosed herein may comprise myricetrin. In an additional example, a pharmaceutical composition disclosed herein may comprise the flavanolol such as dihydromyricetin and dihydrorobinetin. In yet another example, a pharmaceutical composition disclosed herein may comprise a co-formulation of dexrazoxane and the flavonoid myricetin. In particular, the flavonoid myricetin may regulate mitochondrial toxicity in the heart by altering the activity of pyruvate dehydrogenase kinase (PDK4), a protein that may regulate enzymatic activity in cardiac tissue In some cases, the pharmaceutical compositions described herein may comprise a compound according to Formula 1,

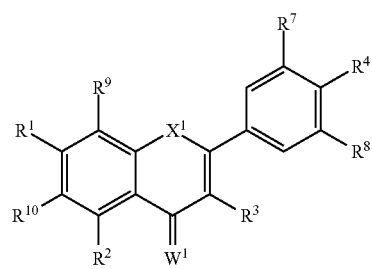

Formula 1 wherein:

$X^1$ is $CR^5R^6$, $NR^5$, O, S, C=O, or C=S;

each of $R^1$, $R^2$, $R^3$, $R^5$, $R^6$, $R^9$, and $R^{10}$ is independently alkyl, alkenyl, alkynyl, alkoxy, acyl, acyloxy, carboxylic acid, ester, amine, amide, carbonate, carbamate, nitro, thioether, thioester, cycloalkyl, heteroalkyl, heterocyclyl, monosaccharide, aryl, or heteroaryl, any of which is substituted or unsubstituted, halogen, hydroxyl, sulfhydryl, nitro, nitroso, cyano, azido, or H;

$R^4$, $R^7$ and $R^8$ are alkoxy, hydroxyl or H;

$W^1$ is O or S; or a salt thereof.

In some aspects, $X^1$ can be O or S, each of $R^1$, $R^2$, $R^3$, $R^9$, and $R^{10}$ can be independently alkoxy, cycloalkyl, halogen, hydroxyl, sulfhydryl, nitro, nitroso, cyano, azido, or H; and each of $R^4$, $R^7$ and $R^8$ can be alkoxy, hydroxyl or H.

In some aspects, $X^1$ can be O; each of $R^1$, $R^2$, $R^3$, $R^9$, and $R^{10}$ can be independently alkoxy, cycloalkyl, halogen, hydroxyl, sulfhydryl, nitro, nitroso, cyano, azido, or H; and each of $R^4$, $R^7$ and $R^8$ can be alkoxy, hydroxyl or H.

In yet other aspects, $X^1$ can be O; each of $R^1$ and $R^2$ can be independently hydroxyl or H; each of $R^3$, $R^9$ and $R^{10}$ can be cycloalkyl, heterocyclyl, hydroxyl, or H; $R^4$ can be hydroxyl; and $R^7$ and $R^8$ can be hydroxyl or H.

In yet other aspects, $X^1$ can be O; $R^1$ can be hydroxyl; each of $R^2$ and $R^3$ can be independently hydroxyl or H; $R^9$ and $R^{10}$ can be H; $R^4$ can be hydroxyl; and $R^7$ and $R^8$ can be hydroxyl or H.

In yet other aspects, $X^1$ is O; $R^1$ is hydroxyl; each of $R^2$ and $R^3$ can be independently hydroxyl or H; $R^9$ can be heterocyclyl or H; of $R^{10}$ is H; $R^4$ can be independently hydroxyl or H; and each of $R^7$ and $R^8$ can be independently hydroxyl or H.

In yet other aspects, $X^1$ is O; $R^1$ is hydroxyl; each of $R^2$ and $R^9$ can be independently hydroxyl or H; $R^3$ can be cycloalkyl, hydroxyl or H; $R^{10}$ is H; R4 is hydroxyl; and each of $R^7$ and $R^8$ can be independently hydroxyl or H. In one embodiment, cycloalkyl of $R^3$ can be a monosaccharide.

In a particular example, the compound can be of the following formula:

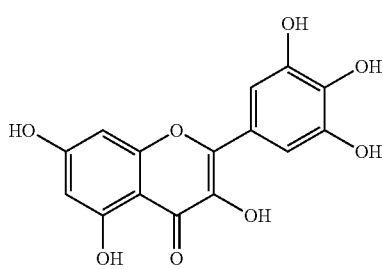 [SMILES: O=c1c(O)c(-c2cc(O)c(O)c(O)c2)oc2cc(O)cc(O)c12]

In a particular example, the compound can be myricetin. In one particular example, the compound can be robinetin. In one particular example, the compound can be tricetin. In one particular example, the compound can be 7,3',4',5'-tetrahydroxyflavone. In one particular example, the compound can be ficetin. In one particular example, the compound can be kaempferol. In one particular example, the compound can be quercetin.

In a particular example, a protective agent within the pharmaceutical composition can be a compound with the following structure:

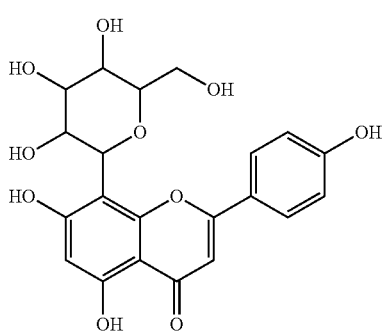 [SMILES: O=c1cc(-c2ccc(O)cc2)oc2c(C3OC(CO)C(O)C(O)C3O)c(O)cc(O)c12]

In a particular example, a protective agent within the pharmaceutical composition can be vitexin, wherein vitexin has the following structure:

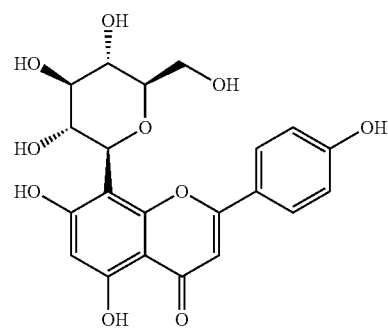 [SMILES: O=c1cc(-c2ccc(O)cc2)oc2c([C@@H]3O[C@H](CO)[C@@H](O)[C@H](O)[C@H]3O)c(O)cc(O)c12]

In a particular example, the compound may be a compound according to Formula 1, wherein $R^1$ is hydroxyl, $R^2$ is hydroxyl, $R^3$ is monosaccharide, $R^4$ is hydroxyl, $R^7$ is hydroxyl, $R^8$ is hydroxyl, $R^9$ is H, $R^{10}$ is H, $X^1$ is O, and $W^1$ is O, or a salt thereof. In a particular example, the compound can be of the following formula:

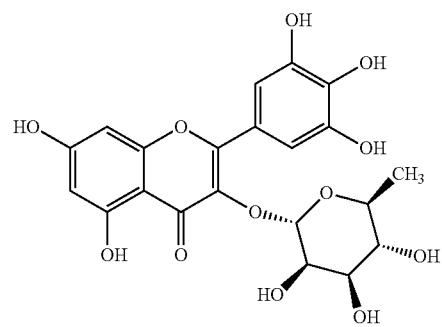 [SMILES: C[C@@H]1O[C@@H](Oc2c(-c3cc(O)c(O)c(O)c3)oc3cc(O)cc(O)c3c2=O)[C@H](O)[C@H](O)[C@H]1O]

In a particular example, the compound can be myricetrin/myricitrin.

In some cases, the monosaccharide can be a natural or unnatural sugar molecule. Non-limiting examples of a monosaccharide include glucose, dextrose, fructose, galactose mannose, ribose, deoxyribose, D-allose, L-allose, D-altrose, L-altrose, D-fucose, L-fucose, D-gulose, L-gulose, D-sorbose, D-tagatose, D-arabinose, L-arabinose, D-lyxose, L-lyxose, rhamnose, D-ribose, ribulose, sucroribulose, D-xylose, D-erythrose, L-erythrose, erythrulose, D-threose, and L-threose.

In some cases, the pharmaceutical compositions described herein may comprise a compound according to Formula 2, Formula 2

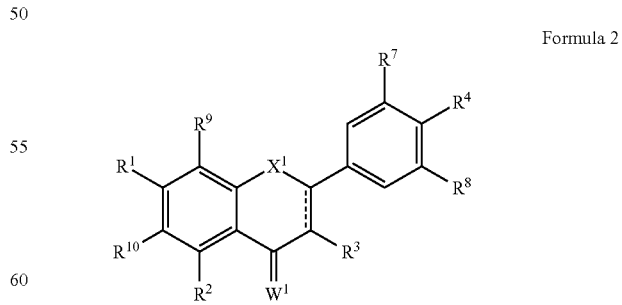

wherein:
$X^1$ is $CR^5R^6$, $NR^5$, O, S, C=O, or C=S;
═══ represents a single or double bond;
each of $R^1$, $R^2$, $R^3$, $R^5$, $R^6$, $R^9$, and $R^{10}$ is independently alkyl, alkenyl, alkynyl, alkoxy, acyl, acyloxy, carboxylic acid, ester, amine, amide, carbonate, carbamate, nitro, thioether, thioester, cycloalkyl, heteroalkyl, heterocyclyl, monosaccharide, aryl, or heteroaryl, any of which is substituted or unsubstituted, halogen, hydroxyl, sulfhydryl, nitro, nitroso, cyano, azido, or H;

$R^4$, $R^7$ and $R^8$ are hydroxyl;

$W^1$ is O or S;

or a salt thereof.

In one particular example, the pharmaceutical compositions Formula 2 may comprise a dihydrorobinetin.

In some cases, the cancer treatment within the pharmaceutical composition described herein may be a chemotherapeutic drug (e.g., anthracyclines, protein kinase inhibitors, and proteasome inhibitors). Generally, the chemotherapeutic drug may be a drag that can induce cardiotoxicity in a patient or subject. Non-limiting examples of an anthracycline may include daunorubicin, doxorubicin, epirubicin, idarubicin, mitoxantrone, or valrubicin. Non-limiting examples of a protein kinase inhibitor may include a tyrosine kinase inhibitor, afatinib, axitinib, bosutinib, cabozantinib, carfilzomib, ceritinib, cobimetanib, crizotinib, dabrafenib, dasatinib, erlotinib, everolimus, gefitinib, ibrutinib, imatinib, lapatinib, lenvatinib, nilotinib, nintedanib, osimertinib, palbociclib, pazopanib, pegaptanib, ponatinib, regorafenib, ruxolitinib, sirolimus, sorafenib, sunitinib, tofacitinib, tofacitinib, temsirolimus, trametinib, vandetanib, vemurafenib, or vismodegib. Non-limiting examples of tyrosine kinase inhibitors that cause cardiotoxicity include dasatinib, imatinib, lapatinib, mesylate, nilotinib, sorafenib and sunitinib. Non-limiting example of proteasome inhibitors include bortezomib.

In some cases, a pharmaceutical composition disclosed herein may comprise a co-formulation of an anthracycline (e.g., doxorubicin) and a compound of Formula 1 or Formula 2 (e.g., myricetin, vitexin, robinetin, tricetin, ficetin, 7,3',4',5'-tetrahydroxyflavone, dihydrorobinetin, myricitrin, and/or a derivative or salt thereof). For example, the pharmaceutical composition comprises a co-formulation of doxorubicin and myricetin. In another example, the pharmaceutical composition disclosed herein may comprise a co-formulation of a protein kinase inhibitor or proteasome inhibitor (e.g., afatinib or bortezomib) and myricetin. In another example, the pharmaceutical composition disclosed herein may comprise a co-formulation of tyrosine kinase inhibitor and a protective agent. In one embodiment, the pharmaceutical composition disclosed herein may comprise a co-formulation of sunitinib and myricetin. In another example, the pharmaceutical composition disclosed herein may comprise a co-formulation of sorafenib and myricetin.

In some cases, the cancer treatment within the pharmaceutical composition described herein may be a biologic agent (e.g., an antibody). Non-limiting examples of a biologic agent include adotrastuzumabemtansine, alemtuzumab, bevacizumab, blinatumomab, brentuximab vedotin, catumaxomab, cetuximab, gemtuzumab ozogamicin, ibritumomab tiuxetan, ipilimumab, necitumumab, nivolumab, obinutuzumab, ofatumumab, panitumumab, pembrolizumab, pertuzumab, ramucirumab, rituximab, tositumomab-I131, or trastuzumab. For example, a pharmaceutical composition disclosed herein may comprise a co-formulation of bevacizumab and myricetin. For example, a pharmaceutical composition disclosed herein may comprise a co-formulation of trastuzumab and myricetin.

The compounds of the current disclosure, or their pharmaceutically acceptable salts may contain one or more asymmetric centers and may thus give rise to enantiomers, diastereomers, and other stereoisomeric forms that are defined, in terms of absolute stereochemistry, as (R)- or (S)- or, as (D)- or (L)- for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Compounds may be dosed in their enantiomerically pure form. In some examples, the compound has an enantiomeric excess greater than about 50%, 60%, 70%, 80%, 90%, 95%, 96%, 97%, 98%, or 99%. Compounds may be dosed in their diasteriomerically pure form. In some examples, the compound has a diasteriomeric excess greater than about 50%, 60%, 70%, 80%, 90%, 95%, 96%, 97%, 98%, or 99%.

Stereocenters may be defined using the Cahn-Ingold-Prelog priority rules. Compounds may have stereocenters in the R-configuration. Compounds may have stereocenters in the S-configuration.

Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

In certain particular embodiments, more than one compound of the current, disclosure may be administered at a time to a subject. In some embodiments, two compounds of the current disclosure in combination may act synergistically or additively, and either compound may be used in a lesser amount than if administered alone.

In certain embodiments, compounds disclosed herein and/or pharmaceutical compositions thereof can be used in combination therapy with other therapeutic agents. The compounds disclosed herein and/or pharmaceutical compositions thereof and the therapeutic agent can act additively or, more preferably, synergistically. In some embodiments, compounds disclosed herein and/or pharmaceutical, compositions thereof are administered concurrently with the administration of another therapeutic agent. For example, compounds disclosed herein and/or pharmaceutical compositions thereof may be administered together with another therapeutic agent. In other embodiments, compounds disclosed herein and/or pharmaceutical compositions thereof are administered prior or subsequent to administration of other therapeutic agents.

The compounds of the present disclosure, or their pharmaceutically acceptable salts, are generally administered in a therapeutically effective amount. The amount of the compound actually administered may be determined by a physician or caregiver, in the light of the relevant circumstances, including the condition to be treated, the chosen route of administration, the compound administered and its relative activity, the age, weight, the response of the individual patient, the severity of the patient's symptoms, and the like.

The present disclosure further provides salts of any compound described herein. The term, "salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like.

Acid addition salts can arise from the addition of an acid to a compound described herein. In some cases, the acid can be organic. In some cases, the acid can be inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid. Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenyl acetate salt, an N-cyclohexylsulfamate salt, a methanesulfonate salt, an ethanesulfonate salt, a benzenesulfonate salt, a p-toluenesulfonate salt, a 2-hydroxy ethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, caesium, cerium, magnesium, manganese, iron, calcium, strontium, cobalt, titanium, aluminium, copper, cadmium, and zinc. Non-limiting examples of suitable metal salts include a lithium salt, a sodium salt, a potassium salt, a caesium salt, a cerium salt, a magnesium salt, a manganese salt, an iron salt, a calcium, salt, a strontium salt, a cobalt salt, a titanium salt, an aluminium salt, a copper salt, a cadmium salt, and a zinc salt. Ammonium salts can arise from the addition of ammonia or an organic amine to a compound described herein. Non-limiting examples of suitable organic amines include tri ethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine. Non-limiting examples of suitable ammonium salts can be a tri ethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a di cyclohexyl amine salt, and a N-methylglucamine salt.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions of the disclosure is contemplated. Supplementary active ingredients can also be incorporated into the compositions.

The term "pharmaceutically acceptable excipient" is intended to include vehicles and carriers capable of being co-administered with a compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multi-binding compounds also falls within the scope of the present disclosure.

In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, PEG, polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propyl hydroxy-benzoates; sweetening agents; and flavoring agents. The compositions of the disclosure can be formulated so as to provide quick, sustained or delayed release of the active ingredient after administration to the patient by employing procedures known in the art.

In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or polyethylene glycol), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

Formulations

The pharmaceutical compositions disclosed herein may be any type of formulation including solid formulations comprising a compound of Formula 1 or Formula 2.

In some cases, the solid formulation comprises at least 0.01 mg, 0.1 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of one or more protective agent of Formula 1 or Formula 2 formulated singly or in combination with a chemotherapeutic drug or biologic.

In some cases, the solid formulation may comprise at least 0.1 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1 g, 5 g, 10 g, 25 g, 50 g or 100 g of one or more protective agents (e.g., myricetin, and/or a derivative or salt thereof). For example, a pharmaceutical composition described herein may be a 100 mg solid co-formulation of myricetin (75 g of the 100 mg dose) and doxorubicin (25 mg of the 100 mg dose).

In some cases, the solid formulation (or other type of formulation) can comprise at least 0.1 mg, 1 mg, 2 mg, 3 mg, 4 mg, 5 mg, 6 mg, 7 mg, 8 mg, 9 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, or 1000 mg of dexrazoxane. For example, a pharmaceutical composition described herein may comprise a 100 mg solid co-formulation of myricetin (75 mg of the 100 mg dose) and dexrazoxane (25 mg of the 100 mg dose).

The pharmaceutical compositions disclosed herein may be a liquid formulation. In some cases, the liquid formulation can comprise at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml concentration of one or more protective agent(s) of Formula 1 or Formula 2 formulated singly or in combination with either a chemotherapeutic drug or biologic agent. For example, a pharmaceutical composition described herein may comprise a 100 mg/mL concentration of the protective agent myricetin and a 50 mg/mL concentration of doxorubicin.

In some cases, the liquid formulation may comprise at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml concentration of myricetin, or derivative or salt thereof. For example, a pharmaceutical composition described herein may comprise 100 mg/mL concentration of myricetin.

In some cases, the liquid formulation can comprise at least 0.1 mg/ml, 1 mg/ml, 2 mg/ml, 3 mg/ml, 4 mg/ml, 5 mg/ml, 6 mg/ml, 7 mg/ml, 8 mg/ml, 9 mg/ml, 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 150 mg/ml, 200 mg/ml, 250 mg/ml, 300 mg/ml, 350 mg/ml, 400 mg/ml, 450 mg/ml, 500 mg/ml, 550 mg/ml, 600 mg/ml, 650 mg/ml, 700 mg/ml, 750 mg/ml, 800 mg/ml, 850 mg/ml, 900 mg/ml, 950 mg/ml, or 1000 mg/ml concentration of dexrazoxane co-formulated with one or more protective agent.

In some cases, a pharmaceutical composition described herein may comprise at least 2 protective agents. The molar ratio of one protective agent to at least one other protective agent can be about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:1,000, about 1:10,000, or about 1:10,000.

In some cases, a pharmaceutical composition described herein may comprise a cancer treatment (e.g., chemotherapeutic drug or biologic agent) and at least one protective agent. The molar ratio of the cancer treatment to at least one other protective agent can be about >10,000:1, about 10,000:

1, about 1,000:1, about 100:1, about 90:1, about 80:1, about 70:1, about 60:1, about 50:1, about 40:1, about 30:1, about 20:1, about 10:1, about 9:1, about 8:1, about 7:1, about 6:1, about 5:1, about 4:1, about 3:1, about 2:1, about 1:1, about 1:2, about 1:3, about 1:4, about 1:5, about 1:6, about 1:7, about 1:8, about 1:9, about 1:10, about 1:20, about 1:30, about 1:40, about 1:50, about 1:60, about 1:70, about 1:80, about 1:90, about 1:100, about 1:1,000, about 1:10,000, or about 1:>10,000

Kits

In some cases, the pharmaceutical compositions disclosed herein may be assembled into kits. In some cases, the kit can comprise a protective agent, wherein the protective agent may exist as distinct entities within the kit or as a co-formulation. For example, the kit may comprise one or more protective agents selected from the group consisting of myricetin, tricetin, robinetin, ficetin, vitexin, dihydrorobinetin, 7,3',4',5'-tetrahydroxyflavone, myricitrin, and dexrozoxane. In some cases, the kit can comprise at least two protective agents, wherein the two protective agents may exist as distinct entities within the kit or as a co-formulation. For example, the kit may comprise at least two protective agents selected from the group consisting of myricetin, tricetin, robinetin, ficetin, vitexin, dihydrorobinetin, 7,3',4', 5'-tetrahydroxyflavone, myricitrin, and dexrozoxane. In a particular example, the kit may comprise a co-formulation of myricetin and dexrazoxane. In some cases, the kit can comprise a cancer treatment and at least one protective agent, wherein the cancer treatment and at least one protective agent may exist as distinct entities within the kit or as a co-formulation. For example, the kit may comprise a cancer treatment and myricetin and/or a derivative thereof. For example, the kit may comprise a cancer treatment and robinetin and/or a derivative thereof. For example, the kit may comprise a cancer treatment and dihydrorobinetin and/or a derivative thereof. For example, the kit may comprise a cancer treatment and tricetin and/or a derivative thereof. For example, the kit may comprise a cancer treatment and ficetin and/or a derivative thereof. For example, the kit may comprise a cancer treatment and 7,3',4',5'-tetrahydroxyflavone and/or a derivative thereof.

In one embodiment, the kit may comprise a co-formulation of doxorubicin and myricetin.

In some cases, the kit may also comprise instructions for use. The kit may also comprise vials, tubes, needles, packaging, or other materials.

Kits with unit doses of one or more of the compounds described herein, usually in oral or injectable doses, are provided. Such kits may include a container containing the unit dose, an informational package insert describing the use and attendant benefits of the drugs in treating the disease, and optionally an appliance or device for delivery of the composition.

The kit may further comprise any device suitable for administration of the composition. For example, a kit comprising an injectable formulation of pharmaceutical compositions may comprise a needle suitable for subcutaneous administration and an alcohol wipe for sterilization of the injection site.

In some cases, kits may be provided with instructions. The instructions may be provided in the kit or they may be accessed electronically. The instructions may provide information on how to use the compositions of the present disclosure. The instructions may further provide information on how to use the devices of the present disclosure. The instructions may provide information on how to perform the methods of the disclosure. In some cases, the instructions may provide dosing information. The instructions may provide drug information such as the mechanism of action, the formulation of the drug, adverse risks, contraindications, and the like. In some cases, the kit is purchased by a physician or health care provider for administration at a clinic or hospital. In some cases, the kit is purchased by a laboratory and used for screening candidate compounds.

EXAMPLES

Example 1. Myricetin Provides Long-Term Cardioprotection (Cell Viability)

Cell samples were prepared by differentiating induced pluripotent stem cells into cardiomyocytes. Cells were cultured for 4 days post-differentiation, changing media at day 3, before performing experiments. Samples were either mock-treated, treated with 1.25 µM doxorubicin, treated with myricetin, or co-treated with 1.25 µM of doxorubicin and myricetin for 72 hours. Following treatment, the samples were incubated Hoesehst 33342 to indicate cell nuclei. Cells were imaged using the EMC ell Analyzer2200, and images were analyzed to quantify the total number of cells and plotted as a percentage of total cells normalized to control (left), where each data point was obtained from three biological replicates. Representative images (FIG. 3, right) are presented for each sample, where an increase in Hoechst 33342 signal represents an increase ion cell viability.

Figure 3:
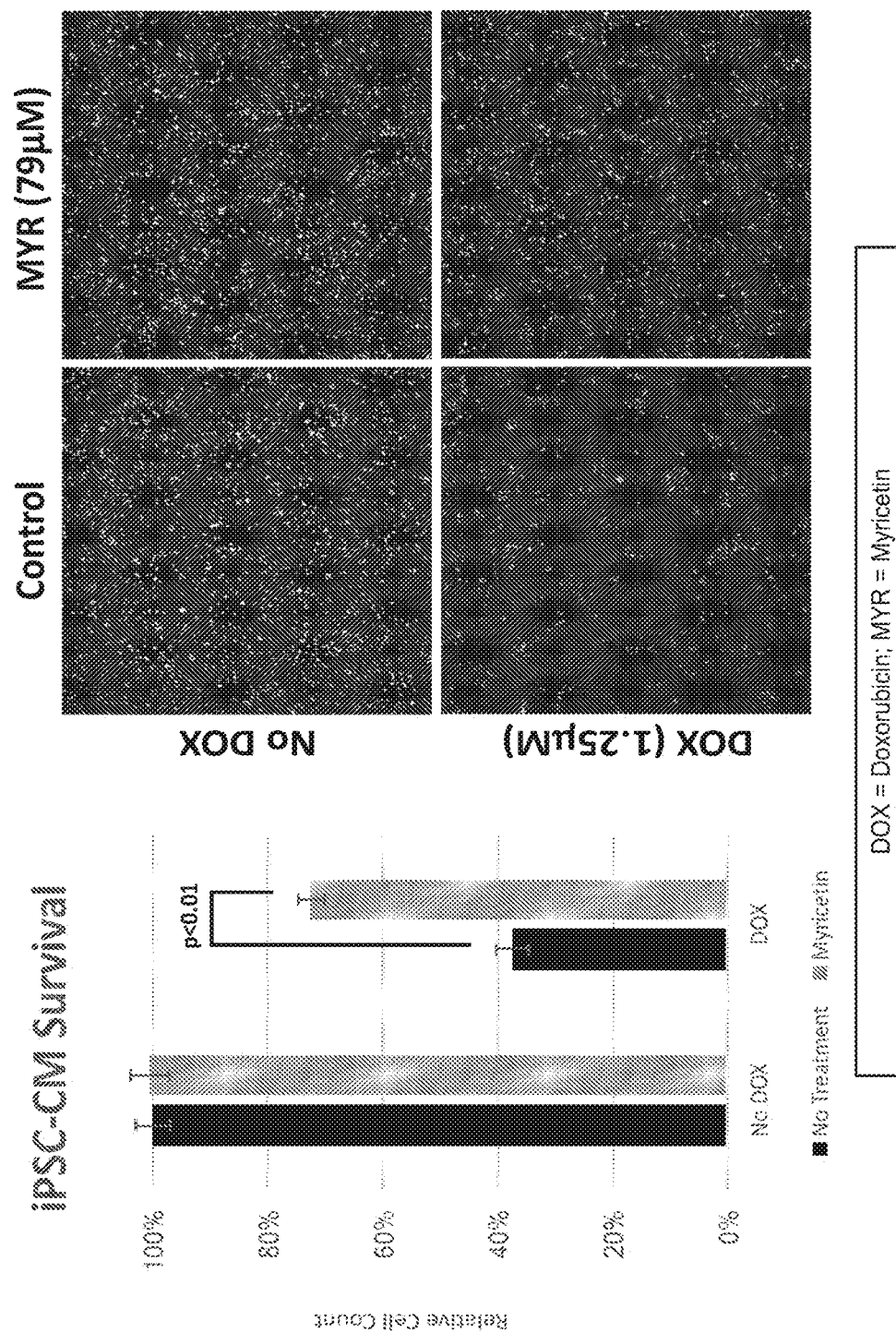
FIG. 3 depicts the effects of mock treatment, doxorubicin (DOX), myricetin, or a co-administration of doxorubicin and myricetin on cell survival in human induced pluripotent stem cell-derived cardiomyocytes (iPSC-CM) 3 days following treatment.

Cardiomyocytes were either mock-treated, treated with 1.25 µM doxorubicin, treated with myricetin, or co-treated with 1.25 µM of doxorubicin and myricetin for 72 hours, and subsequently stained to detect total number of cells (FIG. 3). Myricetin was a potent protector of cell viability. Cardiomyocytes treated with 1.25 µM doxorubicin, in the absence of myricetin, exhibited a 62.6% reduction in the number of total cells, whereas cardiomyocytes co-treated with myricetin and 1.25 µM doxorubicin exhibited a 27.57% reduction the number of total cells, as compared to mock-treated control. Cardiomyocytes treated with myricetin, in the absence of doxorubicin, exhibited no significant difference in the number of total cells, as compared to mock-treated control. Error bars represent, standard deviation. Representative images are presented for each sample, where an increase in Hoechst 33342 signal represents an increase in cell viability. Cardiomyocytes treated with 1.25 µM doxorubicin (FIG. 3, right: bottom left panel), in the absence of myricetin, exhibited a reduction in Hoechst 33342 signal, whereas cardiomyocytes co-treated with 79 µM myricetin and 1.25 µM doxorubicin (FIG. 3, right: bottom right panel) exhibited less reduction in Hoechst 33342 signal, as compared to mock-treated control (FIG. 3, right: top left panel). Cardiomyocytes treated with myricetin (FIG. 3, right: top right panel), in the absence of doxorubicin, exhibited no significant difference in Hoechst 33342 signal, as compared to mock-treated control.

Example 2. Effects of Myricetin on Doxorubicin-Induced Cardiotoxicity 2 Days Following Treatment (Mitochondrial Toxicity)

Human iPSC-derived cardiomyocytes were prepared by differentiating induced pluripotent stem cells into cardiomyocytes. Cells were cultured for 4 days post-differentiation, changing media at day 3, before performing experiments. Cardiomyocytes were treated with 1.25 µM doxorubicin (FIG. 4A), or co-treated with 1.25 µM of doxorubicin and 79 µM myricetin (FIG. 4B) for 2 days.

Figure 4:
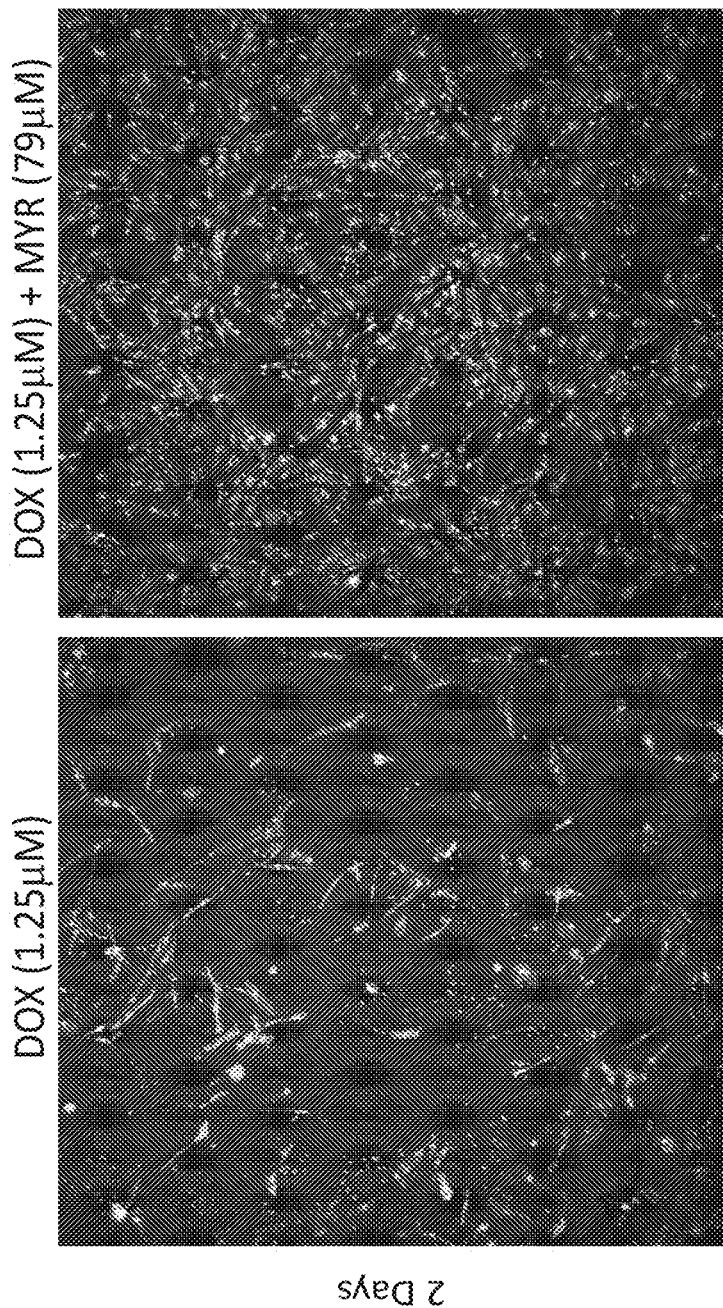
FIG. 4A-B depicts the effects of doxorubicin (DOX) (4A), or a co-administration of doxorubicin and myricetin (4B) on mitochondrial health in human induced pluripotent stem cell-derived cardiomyocytes (iPSC-CM) 2 days following treatment.

Following treatment, the samples were incubated with a tetramethylrhodamine methyl ester (TMRM) dye to indicate mitochondrial health, and Hoechst 33342 to identify cell nuclei. Cells were imaged using the INCell Analyzer2200. Representative images are presented for each sample, wherein a decrease in TMRM signal indicates an increase in mitochondrial toxicity. Myricetin was a potent protector against doxorubicin-induced mitochondrial toxicity, as indicated by a greater TMRM signal in cells co-treated with 1.25 µM doxorubicin and 79 µM myricetin (FIG. 4B) as compared to cells treated with 1.25 µM doxorubicin in the absence of myricetin (FIG. 4A).

Example 3. Effects of Myricetin on Doxorubicin-Induced Cardiotoxicity 3 Days Following Treatment (Contractility)

Figure 5:
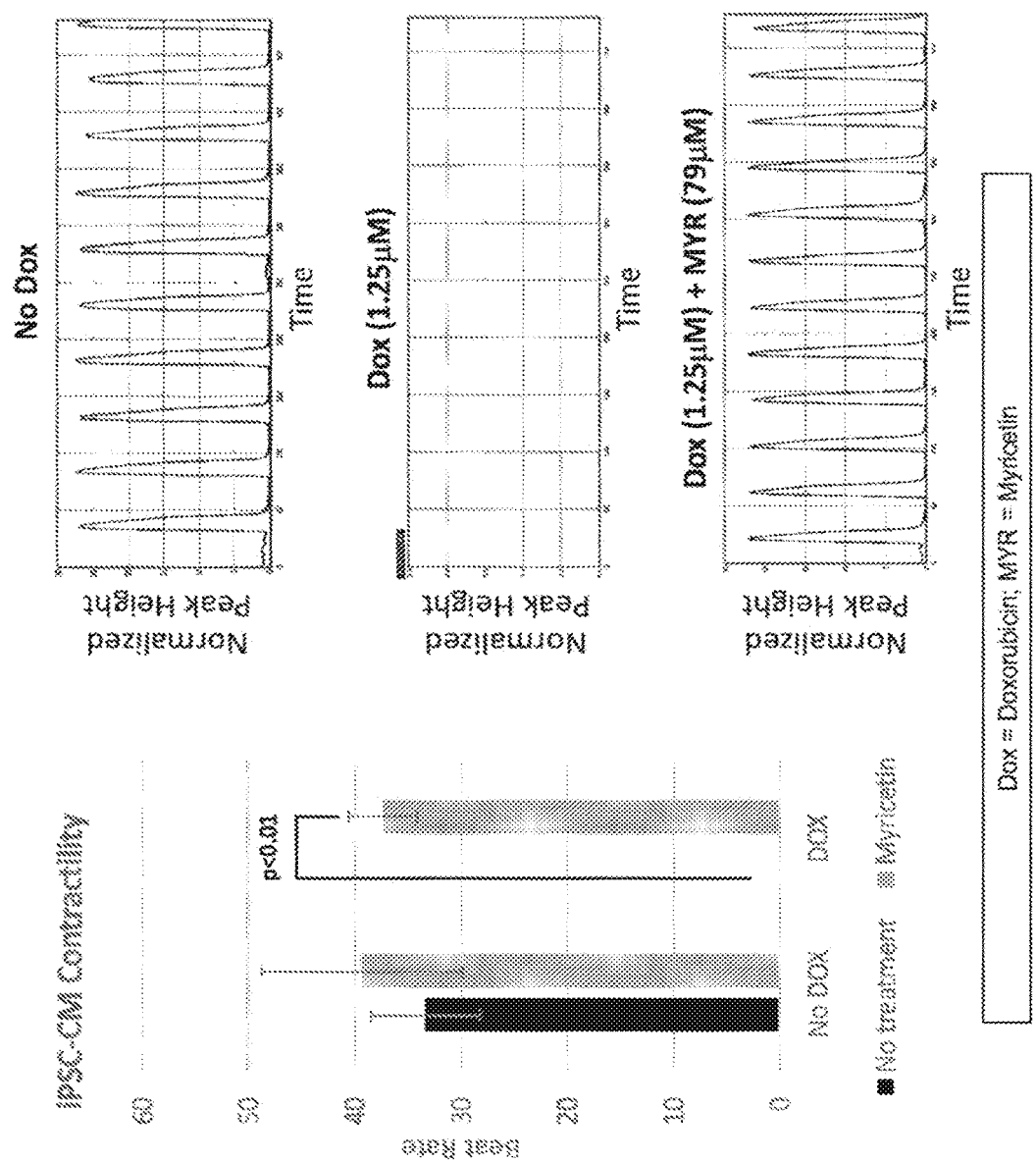
FIG. 5 depicts the effects of mock treatment, doxorubicin, or a co-administration of doxorubicin and myricetin on contractility in human induced pluripotent stem cell-derived cardiomyocytes (iPSC-CM) 3 days following treatment.

Human iPSC-derived cardiomyocytes were prepared as described above. Samples were either mock-treated, treated with 1.25 µM doxorubicin, treated with 79 µM myricetin, or co-treated with 1.25 µM of doxorubicin and 79 µM myricetin for 72 hours. Following treatment, videos of beating cardiomyocytes were captured using Pulse, and analyzed to quantify beat rate (FIG. 5; left) from plots of cell contraction, where each data point was obtained from three biological replicates. Representative plots of cell contraction (FIG. 5; right) are presented for each sample. Myricetin was a potent protector of cell contractility. Mock-treated cardiomyocytes contracted at 33.33 beats per minute, whereas treatment with 1.25 µM doxorubicin, in the absence of myricetin, completely inhibited contraction. Cardiomyocytes treated with myricetin, or co-treated with myricetin and 1.25 µM doxorubicin, contracted at 39.33 or 37.33 beats per minute, respectively. FIG. 6A-C depicts a chart providing the raw data (6A) or normalized data (6B) for the experiments depicted in FIG. 3, or the raw data for the experiments depicted in FIG. 5 (6C).

Example 4. Effects of Various Flavonols and Flavones on Doxorubicin-Induced Cardiotoxicity 3 Days Following Treatment (Apoptosis)

Cardiomyocytes were prepared as described above. Cells were co-treated with 1 µM of doxorubicin and either myricetin (FIG. 7A), myricetrin (FIG. 7B), or dihydromyricetin (FIG. 7C) for 3 days. Following treatment, the samples were incubated with a CellEvent dye to indicate apoptosis-positive cells, and a second dye to identify cell nuclei. Cells were imaged using the INCell Analyzer2200, and images were analyzed to quantify the percentage of apoptotic cells. Data are presented from two independent sets of screening where each data point was obtained from triplicate.

Cardiomyocytes co-treated with doxorubicin and either myricetin (FIG. 7A), myricitrin (FIG. 7B), or dihydromyricetin (FIG. 7C) exhibited protective effects against apoptosis, with half minimal inhibitory concentrations (IC50; e.g., the drug concentration that induces 50 percent apoptosis) of 20.46 µM, 38.48 µM, 40.48 µM, respectively.

Example 5. Myricetin Reduces DOX's Cytotoxicity in Cardiomyocytes

Figure 8:
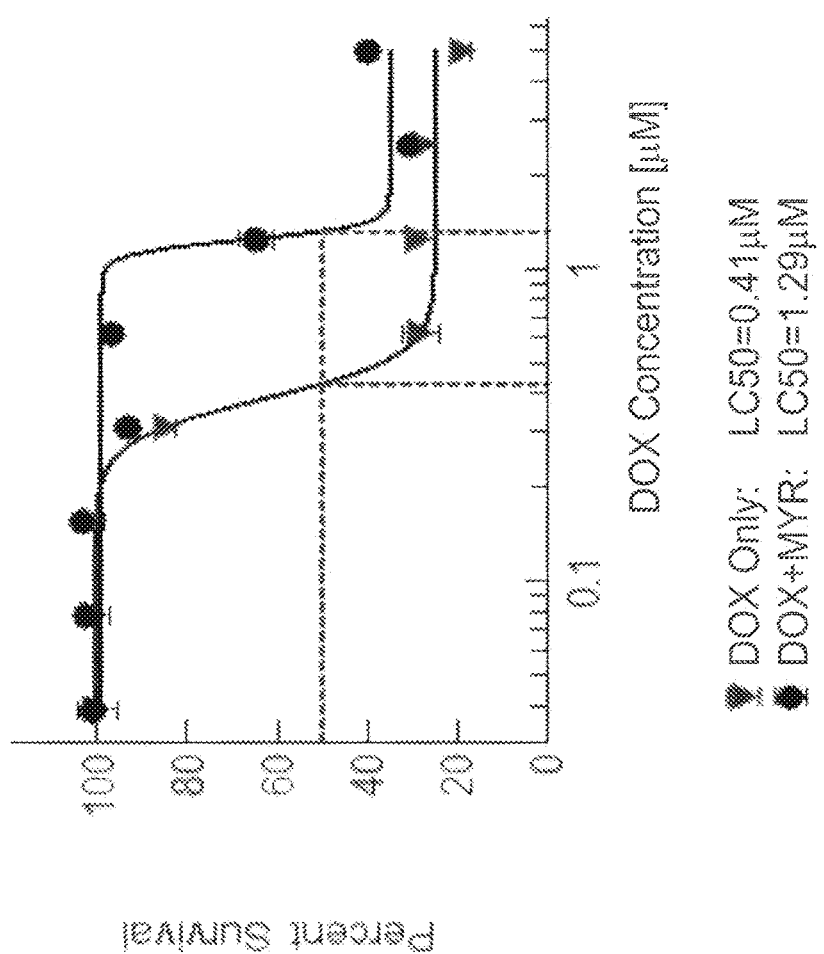
FIG. 8 is a graph illustrating the protective effect of myricetin (MYR; 100 µM) on doxorubicin (DOX)-induced cardiotoxicity at increasing concentrations of doxorubicin for 72 hours. Y-axis, percentage of cell survival; and X-axis, increasing concentrations of DOX.

To assess the effect of MYR against DOX-induced cytotoxicity, human iPSC-derived cardiomyocytes were mock-treated (triangle) or treated with 100 µM of myricetin (MYR; circle) and increasing concentrations of doxorubicin (DOX) for 72 hours, and then incubated with dyes that indicate mitochondrial health (TMRM, Life Technologies) and cellular nuclei (Hoechst33342, Life Technologies). Cells were imaged using INCell Analyzer2200 (GE), Total number of healthy cells were counted and plotted as percentage of mock-treatment control. Lethal concentration at which 50% of cells were killed (LC50) by doxorubicin was shifted from 0.4 µM in mock-treated to 1.29 µM in MYR-treated conditions for iPSC cardiomyocytes (FIG. 8). Data are presented from multiple independent sets of screening where each data point was obtained from triplicate. (n=3). Y-axis; percentage of cell survival; and X-axis: increasing concentrations of DOX (FIG. 8).

Figure 9:
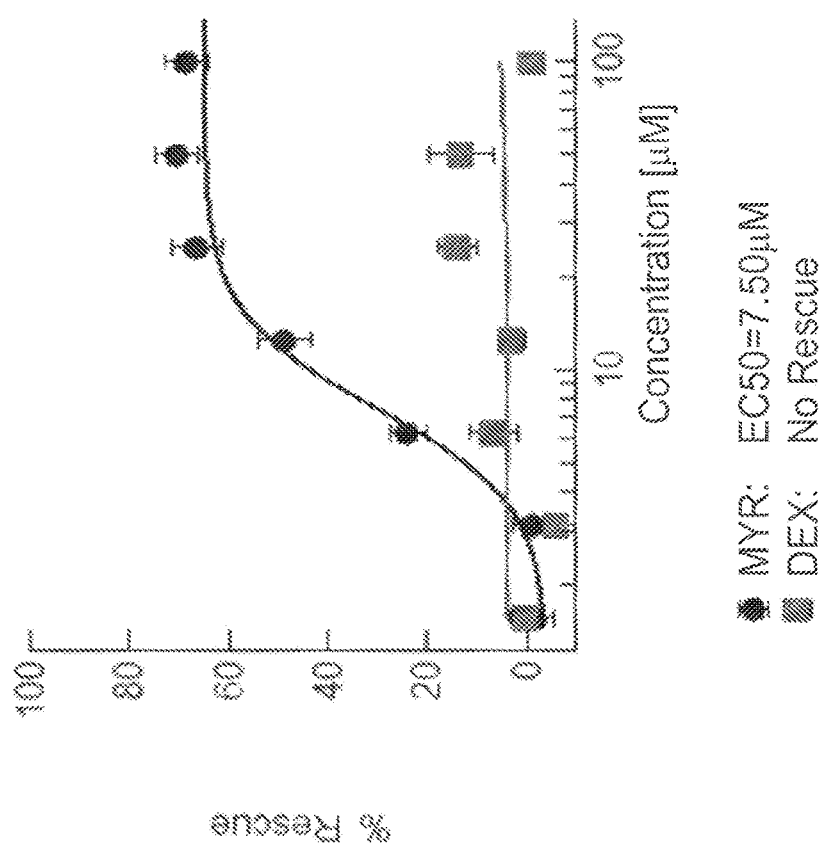
FIG. 9 is a graph illustrating percentage rescue by increasing concentrations (X-axis) of myricetin (MYR; circle) and dexrazoxane (DEX; square) of human induced pluripotent stem cell-derived cardiomyocytes treated with 0.5 µM of doxorubicin (DOX).

Example 6. Myricetin Protects Against DOX-Induced Cell Death in Cardiomyocytes To measure the rescue rates from the DOX-induced cell death in cardiomyocytes, the protective effect of myricetin was directly compared with that of dexraxozane (DEX; standard of care). Human iPSC-derived cardiomyocytes were treated with 0.5 µM of Doxorubicin and increasing concentrations of myricetin (MYR, circle) or dexraxozane (DEX, square). After 72 hours of treatment, cells were incubated with dyes that indicate mitochondrial health (TMRM, Life Technologies) and cellular nuclei (Hoechst33342, Life Technologies). Cells were imaged using INCell Analyzer2200 (GE). Total number of healthy cells were counted and plotted as percentage of doxorubicin-treatment control. Half maximal effective concentration (EC50) for MYR was 7.50 µM (FIG. 9). In contrast, DEX did not exhibit any significant rescues from DOX-induced cytotoxicity. (n=3).

Figure 10:
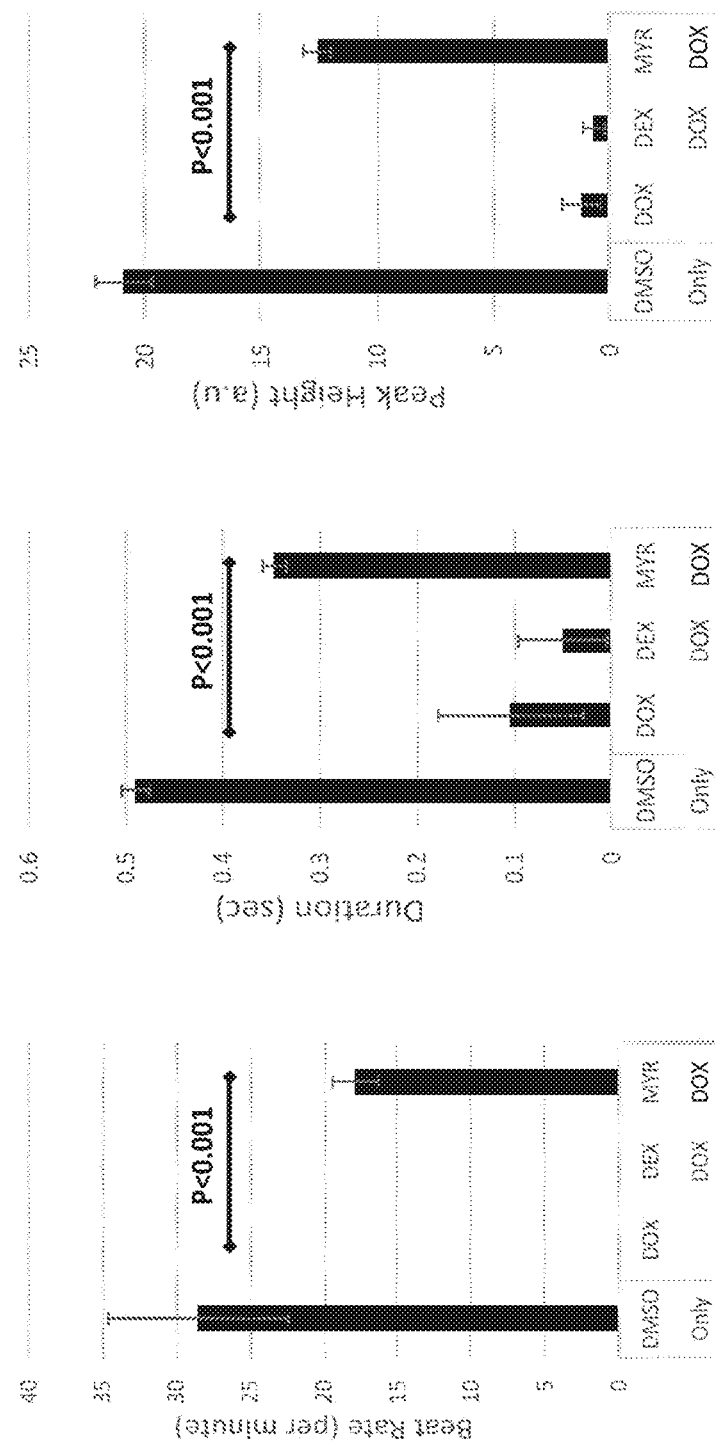
FIG. 10 depicts the protective effects of myricetin against doxorubicin (DOX)-induced contractility dysfunction in cardiomyocytes, represented in a scale of beat rates (per minute; left panel), duration (in second; center panel) and peak height (in arbituary unit; right panel) for mock treated, DOX (0.5 µM), DOX plus DEX (100 µM), or DOX plus MYR (100 µM) after 48 hours of treatment.

Example 7. Myricetin Protects Against DOX-Induced Contractility Dysfunction and DNA Double Strand Break in Cardiomyocytes To assess the protective effect of myricetin on the contractility of heart cells, cell samples were prepared by differentiating induced pluripotent stem cells into cardiomyocytes. Cells were cultured for 4 days post-differentiation, changing media at day 3, before performing experiments. Human iPSC-derived cardiomyocytes were then treated with DMSO, DOX (0.5 µM), DOX plus DEX (100 µM), or DOX plus MYR (100 µM). After 48 hours of treatment, videos of beating cardiomyocytes were captured with Pulse (Cellogy). DOX treatment induced dysfunction in cardiomyocyte contraction as evidenced by reduction in beating, duration, and peak height. This contractile dysfunction was significantly corrected by MYR as compared to DEX (FIG. 10). Bata are presented from multiple independent sets of experiments where each data point was obtained from 6 samples (n=6). Student T-Test (unpaired, two-tailed) was used to determine the significance of the difference.

Figure 11:
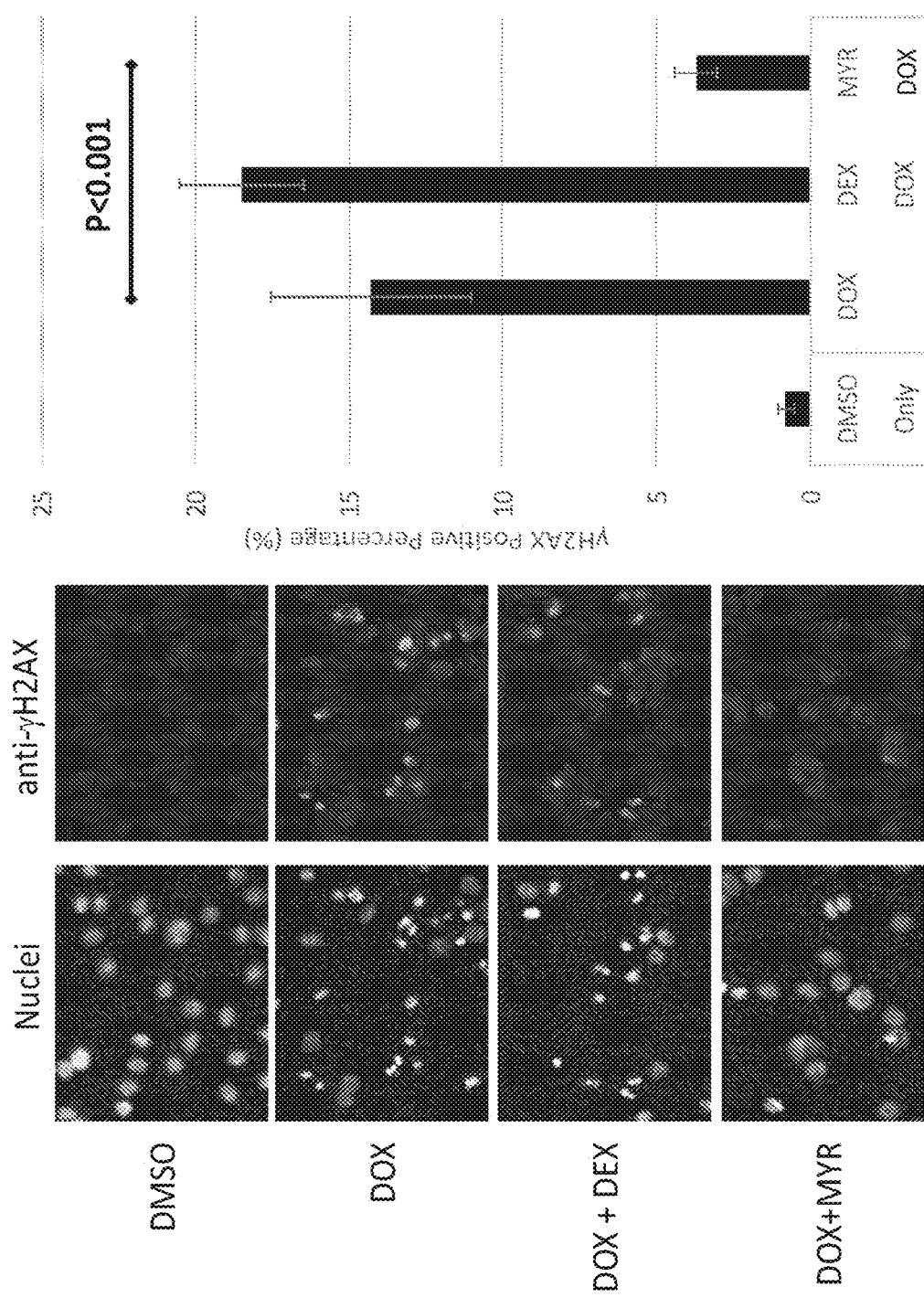
FIG. 11 depicts the effect of myricetin (MYR) on DOX-induced DNA double strand break in human iPSC-derived cardiomyocytes treated with DMSO, DOX alone (0.5 µM), DOX plus DEX (100 µM), or DOX plus MYR (100 µM), measured after 48 hours of the treatment, presented in percentage of γH2AX-positive cells quantified for each condition (right) and representative images of the cells (left).

To determine whether MYR protects against DOX-induced DNA double strand break in cells, human iPSC-derived cardiomyocytes were treated with DMSO, DOX (0.5 µM), DOX plus DEX (100 µM), or DOX plus MYR (100 µM). After 48 hours of treatment, cells were immunostained with antibody against γH2AX (EMI) Millipore) to detect double strand break. Cells were then imaged using INCell Analyzer2200 (GE) and percentages of γH2AX-positive cells were quantified for each condition. While DEX exhibited little or no protection against DOX-induced double strand break in the tested heart cells, MYR conferred significant protection from DOX-related BNA damage (FIG. 11). Student T-Test (unpaired, two-tailed; n=6).

Example 8. MYR Protects Against Sarcomere Disruption by DOX

Figure 12:
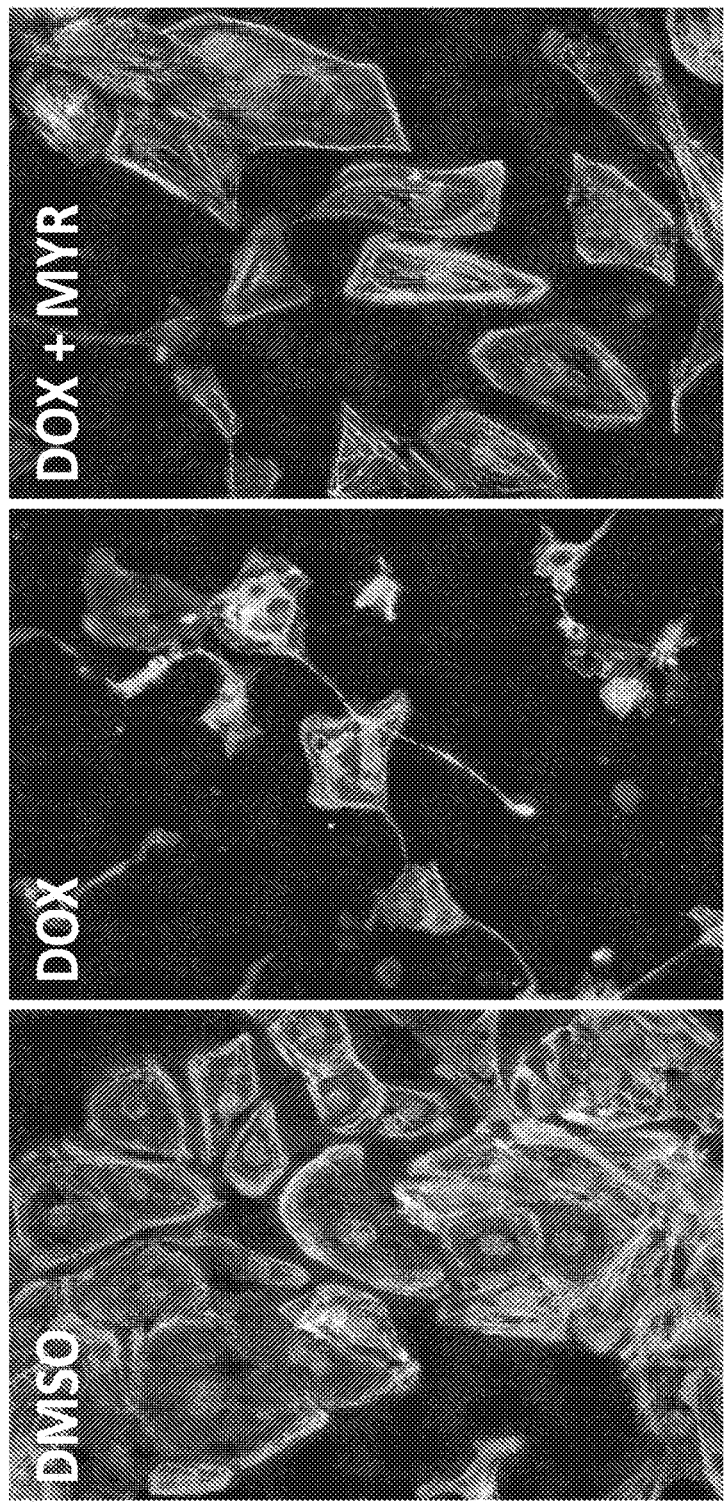
FIG. 12 depicts the effect of myricetin (MYR) on doxorubicin (DOX)-induced sarcomere disruption shown in representative images for mock treated (DMSO; left), DOX alone (0.5 µM; center), or DOX plus MYR (100 µM; right).

DOX-induced cell death is often manifested by severity of structural disruptions of cardiomyocyte organization (e.g., sarcomere). To assess the protective effect of MYR against DOX-induced sarcomere disruption, human iPSC-derived cardiomyocytes were treated with DMSO, DOX (0.5 µM), or DOX plus MYR (100 µM). After 72 hours of treatment, cells were immunostained with antibody against Cardiac Troponin T (Abeam) to show sarcomeric organization in of the heart, cells. As shown in FIG. 12, MYR conferred significant protection against DOX-induced sarcomere disruption in cardiomyocytes, suggesting that the protective effects of MYR against DOX-induced cell death are well manifested by the structural integrity of the cardiomyocytes.

Example 9. Myricetin is a Potent Inhibitor of TOPOIIα and β

To gain insights into a molecular mechanism of myricetin (MYR) and that of dexraxozane (DEX) on cardioprotection, the effect of these two compounds on topoisomerases II (i.e., TOPOIIα and β), an apparent target of DOX, was assessed.

200 ng of kinetoplast DNA (kDNA) was incubated with one enzymatic unit of TOPOIIα or TOPOIIβ enzyme (Inspiralis) and with various concentrations of MYR or DEX at 37° C. for 30 min. The reaction was then separated on 1% agarose gel for visualization of decatenated DNA (bottom band). The efficiency of catalytic inhibition was quantified by measuring the relative intensity of the band.

Figure 13:
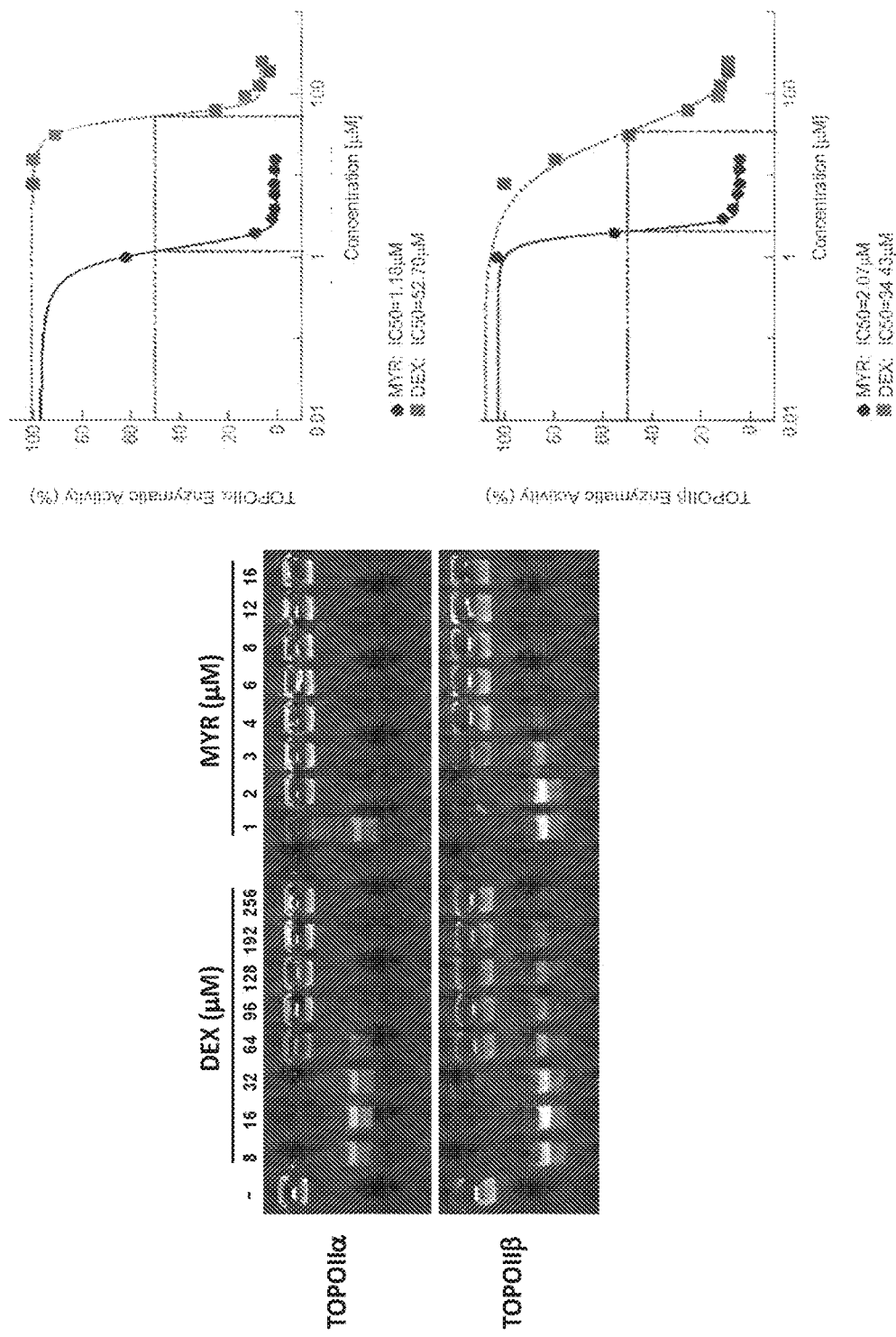
FIG. 13 depicts the effect of myricetin (MYR) on inhibition of topoisomerases IIα and β (TOPOIIα and TOPOIIβ) compared with that of dexrazoxane (DEX).

MYR and DEX exhibited 50% inhibition (IC50) of TOPOIIα enzyme activity at concentrations of 1.18 µM and 52.70 µM, respectively (FIG. 13; n=3). IC50 of TOPOIIβ enzyme activity for MYR and DEX were 2.07 µM and 34.43 µM, respectively (FIG. 13; n=3). The data suggest that MYR is a significantly more potent inhibitor than DEX for both topoisomerases IIα and β.

Example 10. Unlike DEX, MYR does not Induce TOPOII Protein Degradation

To further distinguish molecular mechanisms of MYR from those of DEX and also to determine whether the inhibitory effects of MYR on TOPOII observed in the decatenation assays above is due to degradation of TOPOII proteins, human iPSC-derived cardiomyocytes were treated with DMSO, DEX (100 µM), or MYR (100 µM) for 24 hours, and immunostained with antibody against topoisomerase IIβ (BD Biosciences).

Cells were imaged using INCell Analyzer2200 (GE) and topoisomerase IIβ protein levels were quantified. Student T-Test (unpaired, two-tailed) was used to determine the significance of the difference.

Figure 14:
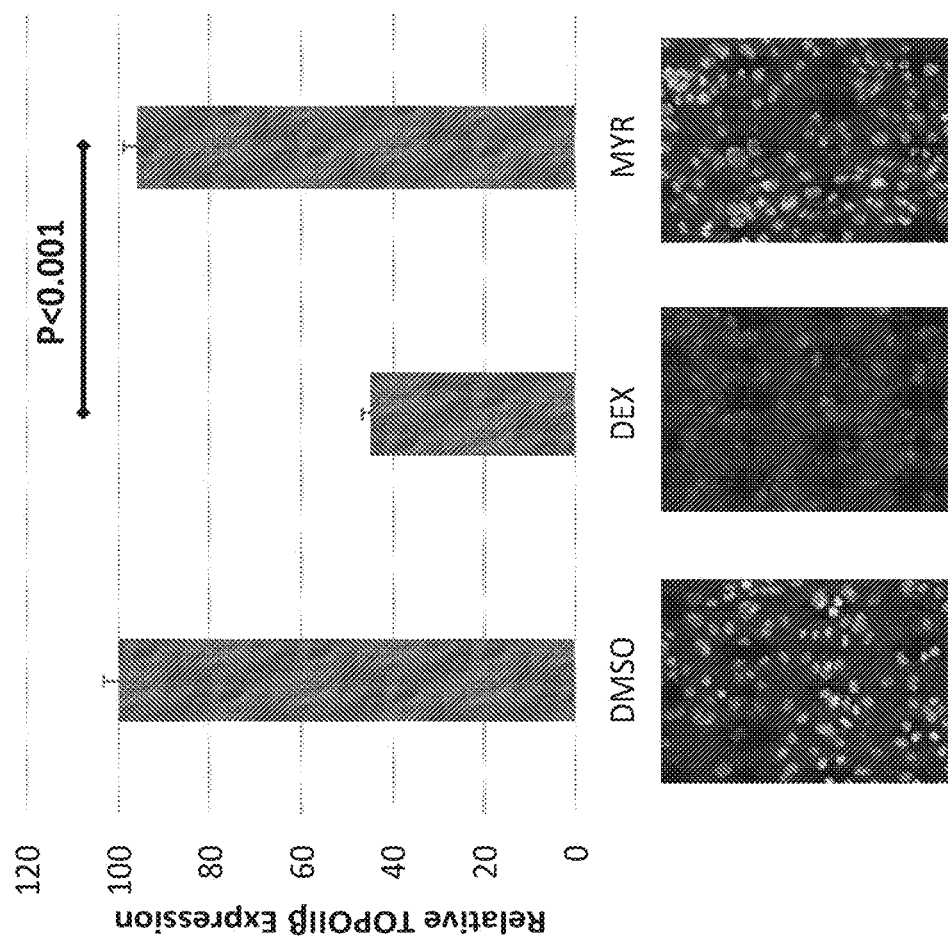
FIG. 14 depicts the effects of myricetin (MYR) and dexrazoxane (DEX) on TOPOIIβ protein degradation illustrated in a graph (top) and representative images (bottom).

As shown in FIG. 14, treatment with DEX resulted in marked disappearance of TOPOIIβ in iPSC-CMs, whereas MYR exerted no effect on topoisomerase IIβ protein levels (FIG. 14) (n=3). The results confirmed the hypothesis that DEX can negatively affect the stability of topoisomerases IIβ (TOPOIIβ), which may lead to the depletion of these enzymes from the heart cells, effectively resulting in prevention of DNA damage generated by poisonous effects on these enzymes by the anthracycline. These results also confirmed that the mechanism by which MYR confer protection from anthracycline-induced toxicity is entirely independent and can be distinguished from that of DEX. Further, the effect of MYR observed in topoisomerase inhibition is not due to TOPOIIβ protein degradation or depletion of the enzyme from DOX's debilitating effects on the heart cells. It can be concluded that inhibition of topoisomerase II activity, particularly without affecting the stability of TOPOII enzymes, is an important factor for MYR's ability to confer cardioprotection.

Example 11. Neither DHM Nor PHR Inhibit TOPOIIα or TOPOIIβ

Since the ability of MYR to confer cardioprotection against DOX-induced toxicity is independent from DEX, it was further investigated to determine whether other flavonoid compounds have a similar effect on topoisomerase II activity like MYR.

First, MYR (flavonol) and dihydromyricetin (flavanonol) were tested for their inhibitory effect on topoisomerase II enzymatic function. Dihydromyricetin (DHM) shares a similar chemical structure except for the presence of a single bond in the major C-ring of the flavonoid scaffold.

Figure 15:
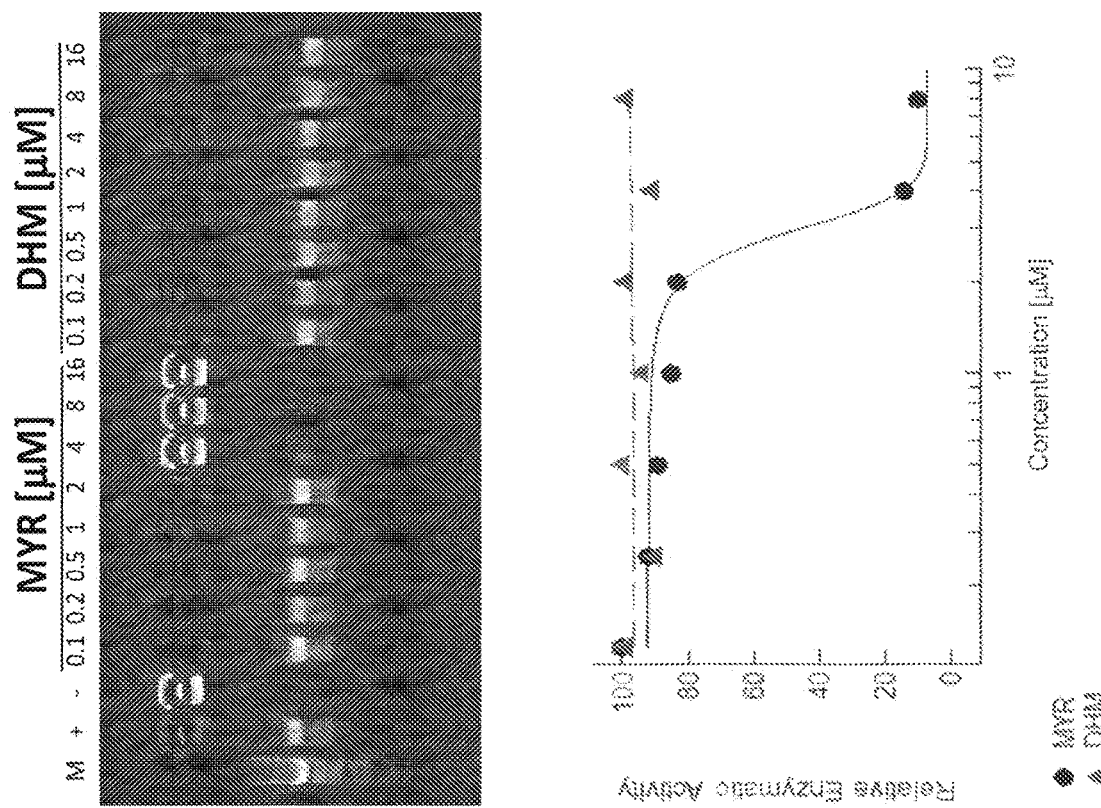
FIG. 15 depicts the effect of myricetin (MYR) and dihydromyricetin (DI-IM) on topoisomerases IIβ (TOPOIIβ) enzymatic inhibition and relative potency thereof as illustrated in a decatenation gel (top) and a graph (bottom).

200 ng of Kinetoplast DNA (kDNA) was incubated with one enzymatic unit of TOPOIIβ and different concentrations of MYR (circle) or DHM (triangle) at 37° C. for 30 min (FIG. 15). The reaction was then separated on 1% agarose gel for visualization of decatenated DNA (bottom band) and the catalytic inhibition efficiency was quantified by measuring the relative intensity of the band. Surprisingly, DHM did not inhibit TOPOIIβ (n=3) (FIG. 15) or TOPOIIα enzymatic activity, even at extreme concentrations (>200 µM).

Further, this result on DHM was confirmed in separate experiments with dihydrorobinetin (DHR) and robinetin (ROB) in which DHR, like DHM, showed no inhibitory activity toward these topoisomerases, while robinetin, like MYR, displayed a high level of inhibition on both TOPOIIβ and TOPOIIα. These data indicate that the structural difference in the C-ring of the flavone/flavonoid scaffold play s an important role in TOPOII inhibition.

Example 12. MYR is 2-Fold More Potent in Protecting DOX-Induced Cell Death than DHM Next, the ability of MYR to confer cardioprotection was directly compared with that of DHM as these two compounds display distinctive property in their structures and TOPOII inhibition activity. Cell samples were prepared by differentiating induced pluripotent stem cells into cardiomyocytes. Cells were cultured for 4 days post-differentiation, changing media at day 3, before performing experiments. Human iPSC-derived cardiomyocytes were treated with 0.5 µM of Doxorubicin and increasing concentrations of myricetin (MYR, circle) or dihydromyricetin (DHM, triangle). After 72 hours of treatment, cells were incubated with dyes that indicate mitochondrial health and cellular nuclei. Cells were then imaged and total number of healthy cells were counted and plotted as percentage of Doxorubicin-treatment control as described above.

Figure 16:
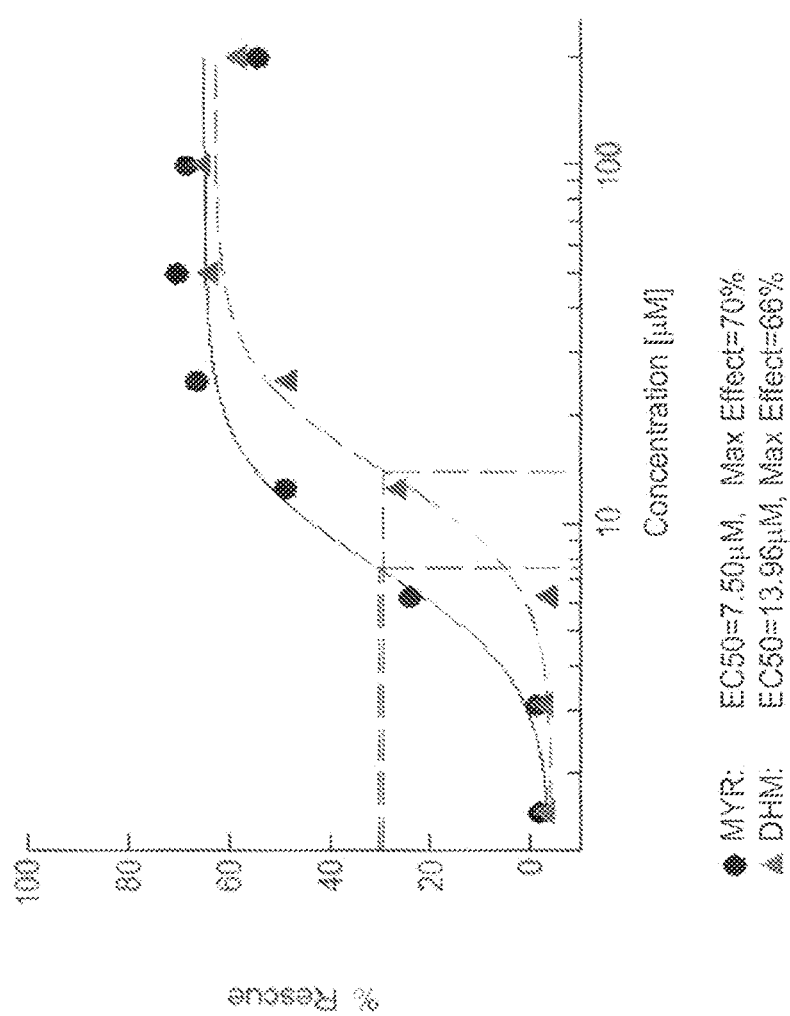
FIG. 16 is a graph illustrating relative potency of MYR and DHM in rescuing cardiomyocytes from DOX-induced cell death.

As illustrated in FIG. 16, MYR exhibited 2-fold greater potency in protecting DOX-induced cell death than DHM as half maximal effective concentrations (EC50) for MYR and DHM were 7.50 µM and 13.96 µM, respectively. (n=3) Based on these results, it was concluded that a double bond in C ring of the flavone/flavonoid scaffold enhances potency for the cardioprotective properties by conferring the inhibitory effects on topoisomerases fl.

Figure 17:
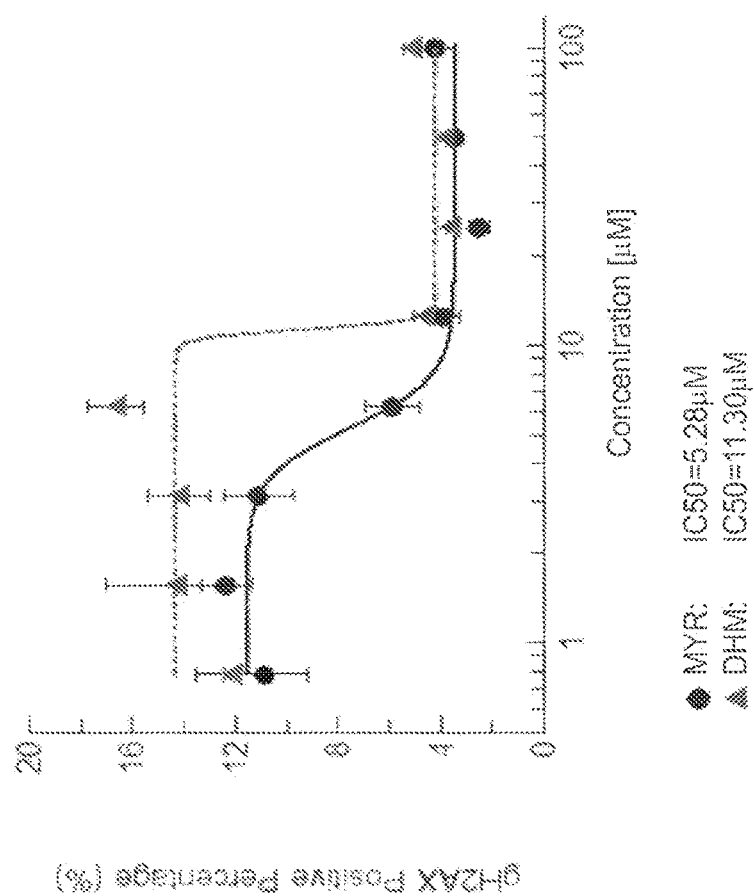
FIG. 17 is a graph illustrating relative potency of MYR and DHM in rescuing cardiomyocytes from DOX-induced double strand break.

These observations were followed up by a DOX-induced DNA double strand break assay. Human cardiomyocytes were treated with 0.5 µM of doxorubicin and with increasing concentrations of MYR (circle) or DHM (triangle). After 48 hours of treatment, cells were immunostained with antibody against γH2AX (EMD Miliipore) to detect DNA double strand break. Cells were imaged using INCell Analyzer2200 (GE) and percentages of γH2AX-positive cells was quantified for each condition. Consistent with its cell death rescue rate, MYR was 2-fold more potent in protecting DOX-induced double strand break than DHM. Concentrations at which DOX-induced double strand break was reduced to 50% (IC50) for MYR and DHM were 5.28 µM and 11.30 µM, respectively (FIG. 17). (n=3)

Figure 18:
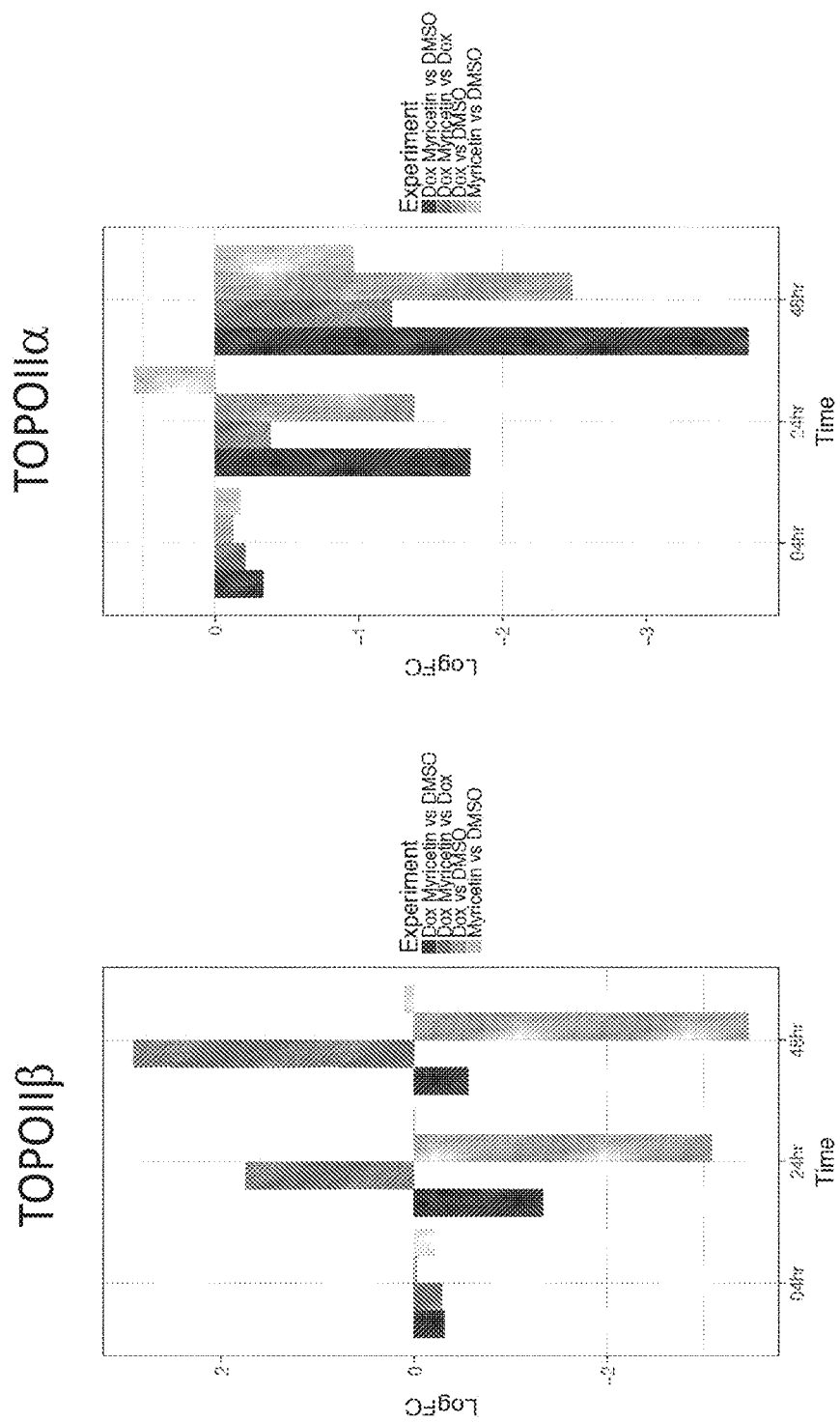
FIG. 18 is a graph illustrating the effect of MYR on RNA expression levels of TOPOIIα (right) and TOPOIIβ (left) as demonstrated in cardiomyocytes treated with DOX alone or DOX plus MYR.

To investigate the effect of myricetin on cardiomyocytes exposed to doxorubicin, mRNA expression levels were determined in the cells treated with DOX alone, myricetin alone, and DOX plus myricetin. Surprisingly while myricetin did not have any effect on TOPOIIβ mRNA expression by itself, DOX significantly repressed TOPOIIβ expression at 24 and 48 hours (FIG. 18). However, in the presence of myricetin, TOPOIIβ expression was restored to a level close to normal by myricetin, effectively preventing any transcription alteration by DOX (FIG. 18). This data suggested that there appeared to be a synergistic effect between DOX and myricetin on TOPOIIβ expression. With respect to expression of TOPOIIα, DOX slowly repressed expression of TOPOIIα over time. In the presence of DOX, however, myricetin further repressed TOPOIIα, suggesting a differential effect of myricetin on these topoisomerases II at molecular and cellular levels. Combined down regulatory effect of myricetin and DOX on TOPOIIα is larger than what was observed with DOX alone.

Example 13. Cardioprotective Properties of MYR Analogs

To further investigate the relationship between the structure (e.g., flavone/flavonol scaffold) and biological activity (e.g., cardioprotection, TOPOII inhibition, etc.), a group of additional flavonoid compounds related to myricetin were identified and tested for their activity.

I. Identification of Flavonoids with Cardio-Protective Properties Mediated Through TOPOII Inhibition Anthracycline-induced cardiotoxicity occurs when the drug such as doxorubicin intercalates the DNA upon a cleavage of DNA by topoisomerase II enzymes, thereby effectively preventing TOPOIIα or β from ligating the cleaved DNA strands back together. Therefore, a working hypothesis was proffered based on cardioprotective properties of flavonoids being mediated through topoisomerases IIα and β (TOPOIIα and TOPOIIβ) inhibition.

A systematic study on the hydroxyl substituents of the MYR scaffold was conducted for biological activity. The objective was to explore chemical space around MYR to identify which substituents (e.g., hydroxyl, alkoxyl, or heterocyclic) are required at various positions and to determine which chemical structure(s) is the essential, component for being a cardioprotectant.

With respect to biological activity, a biochemical decatenation assay was used as described above to assess TOPOIIα and TOPOIIβ inhibition. Doxorubicin treated human iPSC-derived cardiomyocytes were employed to measure the protective effect of these analogs on cardiomyocytes.

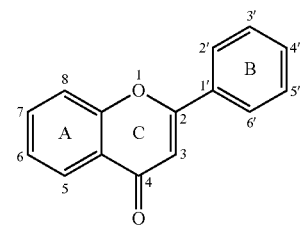

Flavone/Flavonol Scaffold

Starting from the bare flavone, 48 myricetin analog compounds with hydroxyl substituents present or missing at the 3, 5, 7, 3', 4', or 5' positions were identified (myricetin is the compound with all six hydroxyl substituents present). In addition to the 48 myricetin analogs was chromone which is devoid of the B-ring of flavone, and dihydromyricetin and dihydrorobinetin (DHR) which both lack the double bond in the C-ring.

Because substituents can be incorporated into the flavone scaffold at positions 8 and/or 6 on the A-ring similar to vitexin, and also at positions 2' and/or 6' on the C-ring, hydroxyl, alkoxy, alkyl and heterocyclic, halides were contemplated for analysis. The study also included chemical moieties other than hydroxyl substituents present in the MYR scaffold (Formula 1), such as alkoxy (particularly methoxy), alkyl (methyl), heterocyclic, or halides at 3, 5, 7, 3', 4', and/or 5' positions.

This study led to the identification of the minimum structure based on the MYR scaffold required for end point activity. Among the compounds of specific combination of hydroxyl groups in 3, 5, 7, 3', 4', 5' positions selected for biological activity for cardioprotection (e.g., TOPOIIβ inhibition, and DNA double strand break), a certain group of compounds with specific combinations of substituents present or missing at the 3, 5, 7, 3', 4', 5' positions was found to be critical for biological properties as a cardioprotectant with decreased cytotoxicity.

TABLE 1

| ID | Compound Name | iPSC-CM protection Max Effect (%) | EC50 (µM) | Toxicity | Rescue | TOPOIIβ Inhibition | TOPOIIα Inhibition |
|---|---|---|---|---|---|---|---|
| 1 | 3,5,7,3',4',5'-hexahydroxyflavone (myricetin) | 78 | 14.48 | – | ++++ | +++ | +++ |
| 2 | 3,7,3',4',5'-pentahydroxyflavone (robinetin) | 64 | 12.62 | – | ++++ | +++ | +++ |

TABLE 1-continued

| ID | Compound Name | iPSC-CM protection Max Effect (%) | EC50 (µM) | Toxicity | Rescue | TOPOIIβ Inhibition | TOPOIIα Inhibition |
|---|---|---|---|---|---|---|---|
| 3 | 5,7,3',4',5'-pentahydroxyflavone (tricetin) | 56 | 17.19 | * | +++ | +++ | +++ |
| 4 | 3,5,7,3',4'-pentahydroxyflavone (quercetin) | 58 | 20.5 | * | ++ | +++ | +++ |
| 5 | 3,7,3'4'-tetrahydroxyflavone (fisetin) | 36 | 16.32 | * | ++ | +++ | +++ |
| 6 | 7,3',4',5'-tetrahydroxyflavone | 71 | 17.13 | – | +++ | – | – |
| 7 | 3,5,7,4'-tetrahydroxyflavone (kaempferol) | 46 | 26.01 | – | ++ | – | – |
| 8 | 3',4',5'-trihydroxyflavone | 64 | 43.01 | – | + | – | – |
| 9 | 5,7,3',4'-tetrahydroxyflavone (luteolin) | 62 | 9.67 | * | +++ | – | – |
| 10 | 3,7,4'-trihydroxyflavone (resokaempferol) | 27 | 3.26 | * | + | – | – |
| 11 | 7,3',4'-trihydroxyflavone | 24 | 6.25 | * | + | – | – |
| 12 | 3,3',4'-trihydroxyflavone | 16 | 6.43 | * | + | – | – |
| 13 | 5,7,4'-trihydroxyflavone (apigenin) | † | – | – | – | N/A | N/A |
| 14 | 3',4'-dihydroxyflavone | † | – | * | – | N/A | N/A |
| 15 | 7,4'-dihydroxyflavone | † | – | * | – | N/A | N/A |
| 16 | 3,4'-dihydroxyflavone | † | – | * | – | N/A | N/A |
| 17 | 4'-hydroxyflavone | † | – | – | – | N/A | N/A |
| 18 | 3,7,3'-trihydroxyflavone | † | – | * | – | N/A | N/A |
| 19 | 3,5,7-trihydroxyflavone | † | – | * | – | N/A | N/A |
| 20 | 3,7-dihydroxyflavone | † | – | * | – | N/A | N/A |
| 21 | 7,3'-dihydroxyflavone | † | – | * | – | N/A | N/A |
| 22 | 3,3'-dihydroxyflavone | † | – | * | – | N/A | N/A |
| 23 | 5,7-dihydroxyflavone | † | – | * | – | N/A | N/A |
| 24 | 7-hydroxyflavone | † | – | * | – | N/A | N/A |
| 25 | 3-hydroxyflavone | † | – | * | – | N/A | N/A |
| 26 | 3',5'-dihydroxyflavone | † | – | * | – | N/A | N/A |
| 27 | 3'-hydroxyflavone | † | – | * | – | N/A | N/A |
| 28 | flavone | † | – | * | – | N/A | N/A |
| 29 | chromone | † | – | – | – | N/A | N/A |
| 30 | dihydrorobinetin | 53 | 14.02 | – | +++ | – | – |
| 31 | 3'-O-methyl-myricetin | 76 | 58.7 | – | + | – | – |
| 32 | 4'-O-methyl-myricetin | 68 | 48.6 | – | + | – | – |
| 33 | 3',5'-O-dimethyl-myricetin | † | – | * | – | – | – |
| 34 | 3',4',5'-O-tri-methylmyricetin | † | – | * | – | – | – |
| 35 | 3',4',5'-O-tri-methylrobinetin | † | – | * | – | – | – |
| 36 | 7,3',4',5'-O-tetra-methylrobinetin | † | – | * | – | – | – |
| 37 | 3,7,3',4',5'-O-penta-methylrobinetin | † | – | * | – | – | – |

TABLE 1-continued

| ID | Compound Name | iPSC-CM protection Max Effect (%) | EC50 (μM) | Toxicity | Rescue | TOPOIIβ Inhibition | TOPOIIα Inhibition |
|---|---|---|---|---|---|---|---|
| 38 | 7-hydroxy-4-chromone | † | – | * | – | – | – |

+ Compounds exhibited positive effects on respective biological properties
– Compounds exhibited negative effects on respective biological properties
† Compounds failed to exhibit > 30% protection Max Effect at 10 μM or 100 μM on initial screen.
* Compounds exhibited cytotoxicity at 100 μM
N/A, Experiment not performed as compounds exhibited cytotoxicity and no cardioprotection activity Minimum Requirements of Hydroxyl Substituents for TOPOIIβ Inhibition and Cardioprotective Effects As shown in Table 1 above, the common features of the TOPOIIβ inhibitors (1-5) allowed an inference that hydroxyl substituents are required at positions 3, 7, 3', and 4' in order for flavonoid compounds to inhibit TOPOIIβ. The only exception is tricetin (3) which does not have the 3-hydroxyl substituent; all of the other four TOPOIIβ inhibitors have hydroxyl substituents at positions 3, 7, 3', and 4'. Furthermore, the common features of the cardioprotective compounds (1-12) in Table 1 above, allowed an additional inference that the 4' hydroxyl substituent on the B-ring may be an essential feature, along with two of the other three hydroxyl substituents at positions 3, 7, and 3 for cardioprotective activity, with the hydroxyl at position 7 preferred, the only exception being compound 8 which does not have hydroxyls at positions 3 and 7, yet has all three hydroxyl substituents at positions 3', 4', and 5' on the B-ring. Moreover, considering toxicity of the tested compounds (see Table 1), one can deduce a trend that cardioprotective compounds (1-12) which have all three 3', 4', and 5' hydroxyl substituents on the B-ring do not exhibit toxic effects at concentrations less than 100 μM, whereas those cardioprotective compounds which have hydroxyl substituents only at positions 3' and 4' do indeed exhibit toxic effects at concentrations less than 100 μM. Again, the one exception to this trend was tricetin (3), which exhibits some toxic effects at concentrations less than 100 μM despite containing all three hydroxyl substituents on the B-ring. Of the two cardioprotective compounds which only have the 4' hydroxyl substituent on the B-ring (kaempferol 7 and resokaempferol 10), kaempferol did not show toxic effects below 100 μM, whereas resokaempferol exhibited toxic effects at concentrations below 100 μM. Based on this analysis, it was concluded that:

(1) for cardioprotection, 4' hydroxyl substituent on B-ring is required, along with one of the following, (a) two of the three hydroxyl substituents at positions 3, 7, and 3', with position 7 preferred, or (b) all three hydroxyl substituents at positions 3', 4', and 5' on the B-ring;

(2) for cardiotoxicity, 3', 4', and 5' hydroxyl substituents on the B-ring are preferable to 3' and 4' hydroxyl substituents on the B-ring, to alleviate toxic effects at concentrations below 100 LIM, or, 4' hydroxyl only on the B-ring, along with ail three 3, 5, and 7 hydroxyl substituents on the A/C ring system; and (3) for TOPOIIβ inhibition, all four hydroxyl substituents at positions 3, 7, 3', and 4' are required. Tricetin (3) does not follow these requirements and is an outlier.

Analysis on B-Ring

It is readily apparent from the compounds listed in Table 1 that the 4' position on the B-ring requires a hydroxyl substituent for cardioprotection. Of the twelve compounds (1-12) that passed the initial screen, all of them have the 4'-hydroxyl substituent. Moreover, of the sixteen compounds (13-28) that did not pass the initial screen, eleven (18-28) are absent the 4'-hydroxyl substituent. The remaining five 4'-hydroxyl compounds (13-17) that did not pass the initial screen have minimal substitution, e.g. only the 4'-hydroxyl as in compound 17, or only one other hydroxyl substituent along with the 4'-hydroxyl as in compounds 14, 15, and 16. Compound 13 only has one of the required hydroxyl substituents from the set of 3, 7, and 3' described above; therefore, it also does not meet the minimum requirements for cardioprotective activity, in summary, the presence of a hydroxyl substituent at position 4' on the B-ring is a necessary but not sufficient condition for flavonoid compounds to be cardioprotective. This structural requirement strongly hints at the presence of a hydrogen-bond between the 4' hydroxyl on the B-ring of the protective agent in complex with the biological target.

1. Chromone-Related Compounds

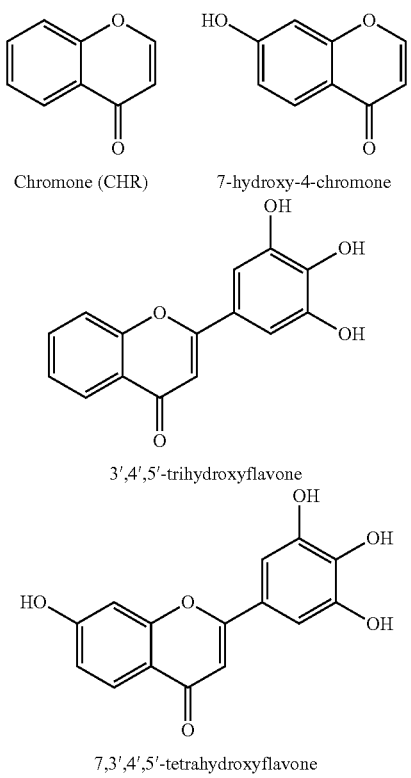

Chromone (CHR)    7-hydroxy-4-chromone

3',4',5'-trihydroxyflavone 7,3',4',5'-tetrahydroxyflavone

Both chromone (29) and 7-hydroxy-4-chromone (38), which each entirely lacks the B-ring of the flavone scaffold, showed no positive effect in cardiac protection. Nor did either compound confer TOPOIIβ or α inhibition (Table 1). Furthermore, 7-hydroxy-4-chromone exhibited a high level of cytotoxicity at 100 μM. Comparing these two B-ring null compounds with the corresponding tri-substituted B-ring flavone compound (8 and 6, respectively), it was concluded that the presence of the B-ring is required for cardiac protection.

Next, the observation obtained from 7-hydroxy-4-chromone was further explored in 3,5,7-trihydroxyflavone having the B-ring, but lacking all B-ring substituents. 3,5,7-tri hydroxy flavone exhibited neither cardioprotection nor TOPOII inhibition and displayed generalized cytotoxicity, indicating that one or more moieties are required in the B-ring for the cardioprotection activity.

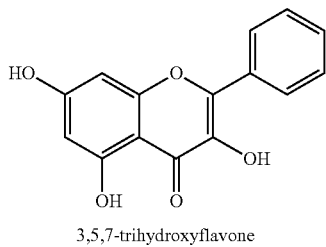 [SMILES: O=c1c(O)c(-c2ccccc2)oc2cc(O)cc(O)c12]

3,5,7-trihydroxyflavone

2. Methoxy Substituents on B-Ring

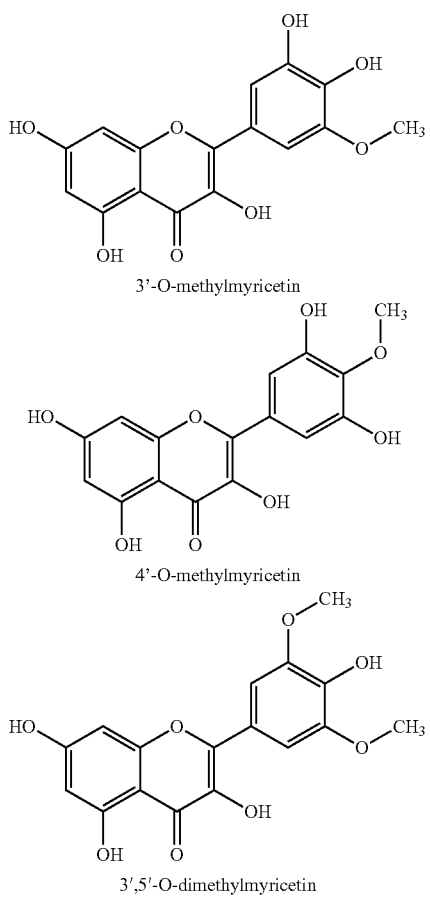

3'-O-methylmyricetin

4'-O-methylmyricetin

3',5'-O-dimethylmyricetin

Since the B-ring appeared to be an essential component for biological activity, compounds having the B-ring with various positional combinations with either hydroxyl and/or methoxy group were tested for their activity.

3'-O-methylmyricetin having methoxy at the 3' position failed to inhibit TOPOII enzymes, but conferred cardioprotection without showing generalized cytotoxicity. However, it exhibited a significant loss of potency for cardioprotection (EC50, 59 μM), Similarly, 4'-O-methylmyricetin having methoxy at 4' position conferred cardioprotection without TOPOII inhibition. This compound displayed a loss of potency for cardioprotection (EC50, ~48.7 μM) as compared to that of MYR. This suggests that the presence of a single methoxy substituent at 3' or 4' of the B-ring, is an important factor for cardioprotection. Confirming this observation, 3',5'-O-dimethylmyricetin, lacking a methoxy substituent at position 4 but having a methoxy at positions 3' and 5' of the B-ring, displayed neither cardioprotection nor TOPOIIα and TOPOIIβ inhibition. This compound also exhibited significant cytotoxicity. Other compounds having multiple methoxy replacements at positions 3', 4', and 5' were also tested for cardioprotection and TOPOII inhibition. For example, all of 3',4',5'-O-trimethylmyricetin, 3',4',5'-O-trimethyirobinetin, 3,7,3',4',5'-O-pentamethylrobinetin, 7,3',4',5'-tetramethylrobinetin entirely failed to display cardioprotection or TOPOII inhibition. All exhibited increased levels of cytotoxicity at 100 μM.

Accordingly, replacing 4' or 3' hydroxyl with methoxy significantly reduces potency and results in complete loss in TOPOII inhibition. Further, because methoxy substitution slightly enlarges and extends the compound from the B-ring, it was postulated that having a larger substituent extending from the B-ring, even at a marginal level, may pose a steric hindrance for the interaction between TOPOII enzyme and the compound. Thus, hydroxyls groups in the B-ring (3',4',5') appears to be critical components that lead to cardioprotection and may play an important role in TOPOII enzyme inhibition.

3. Quercetin and Kaempferol

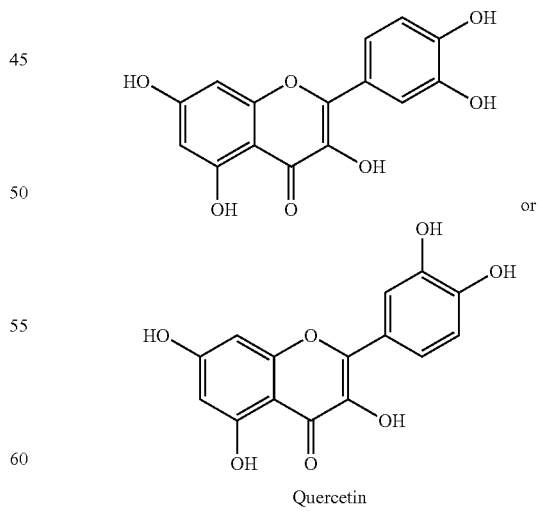

or

Quercetin

Quercetin conferred cardioprotection and exhibited TOPOII inhibition. However, a high level of general cytoxicity to cardiomyocytes was observed at a concentration of 100 μM.

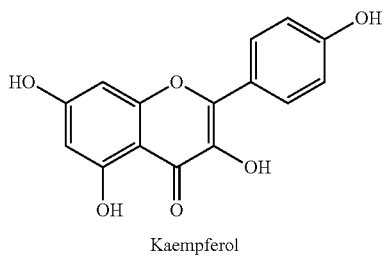 [SMILES: O=c1c(O)c(-c2ccc(O)cc2)oc2cc(O)cc(O)c12]

Kaempferol

Kaempferol displayed a moderate level of cardioprotection without some level of cytotoxicity at 100 µM, but did not exhibit any inhibitory effect on TOPOIIα or TOPOIIβ. Kaempferol, however, displayed decreased potency and failed to achieve the maximum 50% rescue rate.

It was inferred from the data that removing 3' (or 5') hydroxyl may not necessarily result in loss of TOPOII inhibition, but leads to increased cytotoxicity and reduced potency as observed in quercetin. However, these data led to the conclusion that removing 3' 4', or 5' hydroxyl group from the B-ring result in a marked reduction in potency and/or loss of TOPOII inhibition, particularly at position 4'.

In sum, replacing one or two 3', 4', or 5' hydroxyls with an alkoxy (e.g., methoxy) group renders the compound cytotoxic. Removal of 3' and 5' hydroxyl groups from the MYR scaffold, as observed in kaempferol or removal of either 3' or 5' hydroxyl as in quercetin may reduce potency for cardioprotection and render the compound cytotoxic. However, removing all hydroxyls on the B-ring results in complete loss of cardioprotection and TOPOII inhibition, and causes severe cytotoxicity as observed in 3,5,7-trihydroxyflavone. Further, 4' hydroxyl of the B-ring appears to be required for the enhanced physical attributes leading to increased potency for cardioprotection with TOPOII inhibition and minimal cytotoxicity.

Accordingly, the preferred substituents for the B-ring are —OH in all 3', 4' and 5' positions in order to ensure potency and minimal toxicity as demonstrated by myricetin and robinetin.

A and C-Ring Analysis

Substituents on the heterobicyclic A/C ring system of the flavone-flavonol scaffold was assessed for the cardioprotective activity. Based on the observations made on the fi-ring, a subset of compounds having hydroxyls on the B-ring with various combinations with —OH at 3, 5, 7, positions of the A-C ring were tested.

1. Myricetin, Robinetin and Tricetin

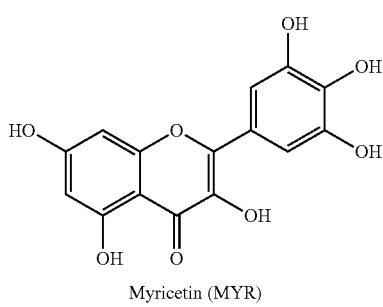

Myricetin (MYR)

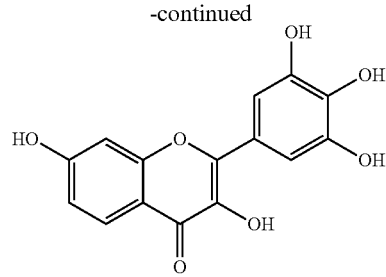

Robinetin (ROB)

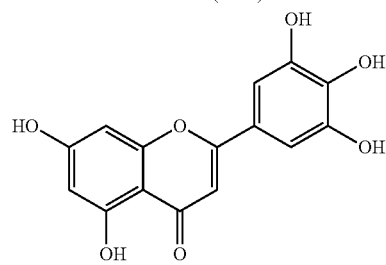

Tricetin (TRI)

MYR (3,5,7,3',4',5'-hexahydroxyflavone) and ROB (3,7,3',4',5'-pentahydroxyflavone) showed equivalent levels of cardioprotection with an EC50 about 10-20 µM and TOPOIIβ and TOPOIIα inhibition at less than 10 µM. Similarly, tricetin (5,7,3',4',5'-pentahydroxyflavone) lacking —OH at position 3 also displayed cardioprotection and TOPOII inhibition with a low level of cytotoxicity at 100 µM. Further, 7,3',4',5'-tetrahydroxyflavone lacking —OH at both positions 3 and 5 of the A/C ring system displayed cardioprotection, but did not inhibit TOPOII enzymes.

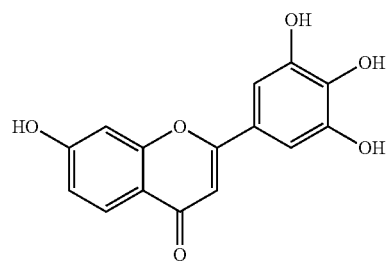

7,3',4',5'-tetrahydroxyflavone

However, 3',4',5'-trihydroxyflavone and other compounds having no —OH at the position 7 failed to display potency less than 30 µM for cardioprotection or TOPOII inhibition. These data suggested that hydroxyl (—OH) at position 7 of the A-ring may be required for cardioprotection, but not sufficient as at least one —OH group at 3 and/or 5 position can greatly enhance activity (e.g., potency and/or TOPOII inhibition) of these compounds for cardioprotection. Thus, hydroxyls in the A/C-ring (3,7) system play an important role for cardioprotection and TOPOII inhibition, provided that 3',4',5' hydroxyls are present on B-ring. Particularly —OH at position 7 in the A-ring appears to be critical for the activity.

Example 14. Protective Effects of MYR on Anticancer Agents

1. Anthracyclines

Figure 19:
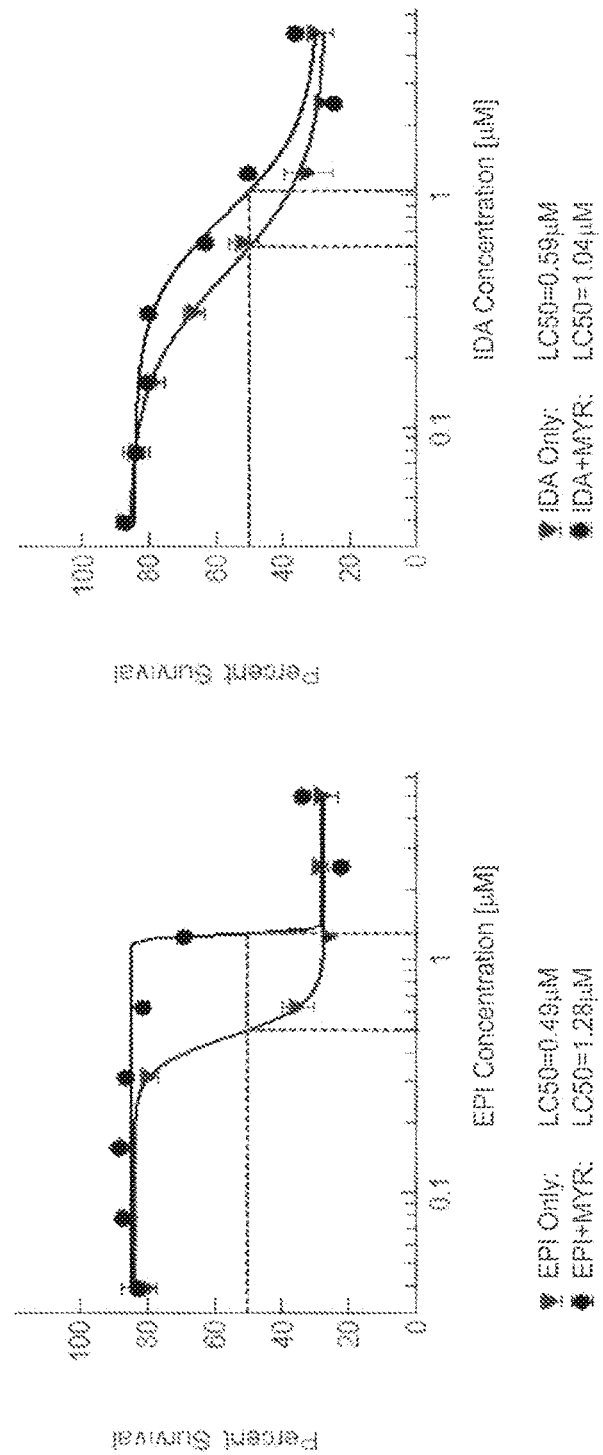
FIG. 19 depicts two graphs illustrating potency of myricetin (MYR) in protecting cardiomyocytes from epirubicin (EPI; left) and idarubicin (IDA; right)-induced cytotoxicity.

MYR Protects Against Epirubicin-Induced Cell Death and Idarubicin-Induced Cell Death Epirubicin and idarubicin are anthracyclines that are associated with heart failure in patients. In addition to doxorubicin described above, the effect of MYR was tested on epirubicin- and idarubicin-induced heart injury. As illustrated in FIG. 19, human iPSC-derived cardiomyocytes were mock-treated (triangle) or treated with 100 µM of MYR (circle) and increasing concentrations of epirubicin or idarubicin for 72 hours, and then incubated with dyes that indicate mitochondrial health and cellular nuclei as describe above. Cells were imaged and total number of healthy cells were counted and plotted as percentage of mock-treatment control.

Lethal concentration at which 50% of cells were killed by epirubicin (LC50) was shifted from 0.49 µM in mock-treated to 1.28 µM in MYR-treated conditions, showing that MYR effectively protected against epirubicin-induced cell death in cardiomyocytes (FIG. 19, left). (n=3)

Similarly, LC50 of Idarubicin was shifted from 0.59 µM in mock-treated to 1.04 µM in MYR-treated conditions, indicating that MYR also protected against idarubicin-induced cell death (FIG. 19, right). (n=3)

2. Protein Kinase and Proteasome Inhibitor

MYR Protects Against Bortezomib-, Sunitinib- and Sorafenib-Induced Cell Death

Cardiotoxicity may result from the formation of toxic reactive oxygen species (ROS) through redox cycling caused by various anticancer agent. The reactive oxygen species (ROS) may activate apoptotic pathways, leading to cell death in both cancer and normal cells. Cardiomyocytes may be particularly sensitive to the oxidative stress and cardiac mitochondria may be easily disrupted by cancer agents like anthracycline, TKI or proteasome inhibitors. According to the data presented above, it was hypothesized that the ability of MYR and its analogs described herein to protect heart, cells can be multifaceted: (1) protection by interacting TOPOII enzymes in the heart cells as in anthracyclines; and (2) the effect exerted independently from the molecular mechanism of TOPOII (e.g., ROS chelation, promoting mitochondrial integrity). To determine whether MYR confers cardioprotection on non-anthracycline drugs, the compound was tested for its ability to protect heart cells against protein kinase inhibitor-induced cytotoxicity.

Sunitinib and sorafenib are tyrosine kinase antagonists used to treat a wide range of cancers including leukemia and sarcoma. However, sunitinib and sorafenib have been reported to cause adverse events like heart failure in patients. Tyrosine kinases are enzymes responsible for the activation of many proteins involved in signal transduction pathways. These proteins are activated via phosphorylation, a step the TKIs are known to target for inhibition.

Bortezomib is a proteasome inhibitor used to treat multiple myeloma and lymphoma. In some cancer, the proteins that normally destroy cancer cells are broken down prematurely. Bortezomib interrupts this process, allowing those proteins to disrupt the dividing cancer cells.

Figure 20:
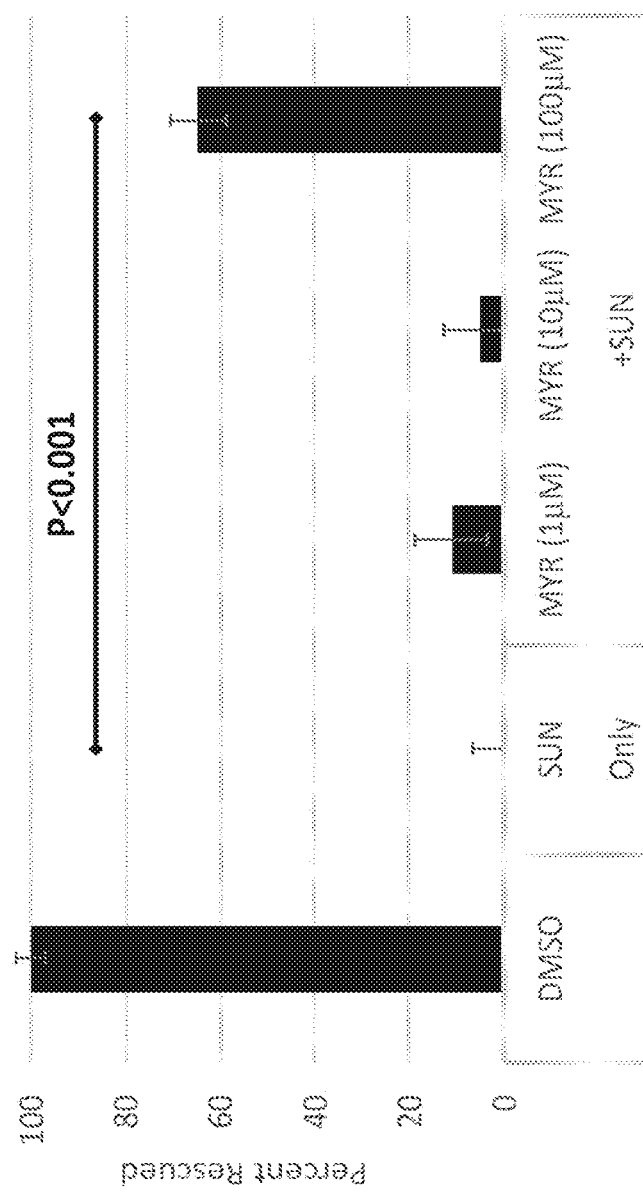
FIG. 20 is a graph illustrating the effect of myricetin (MYR) on sunitinib (SUN)-induced cell death.
Figure 21:
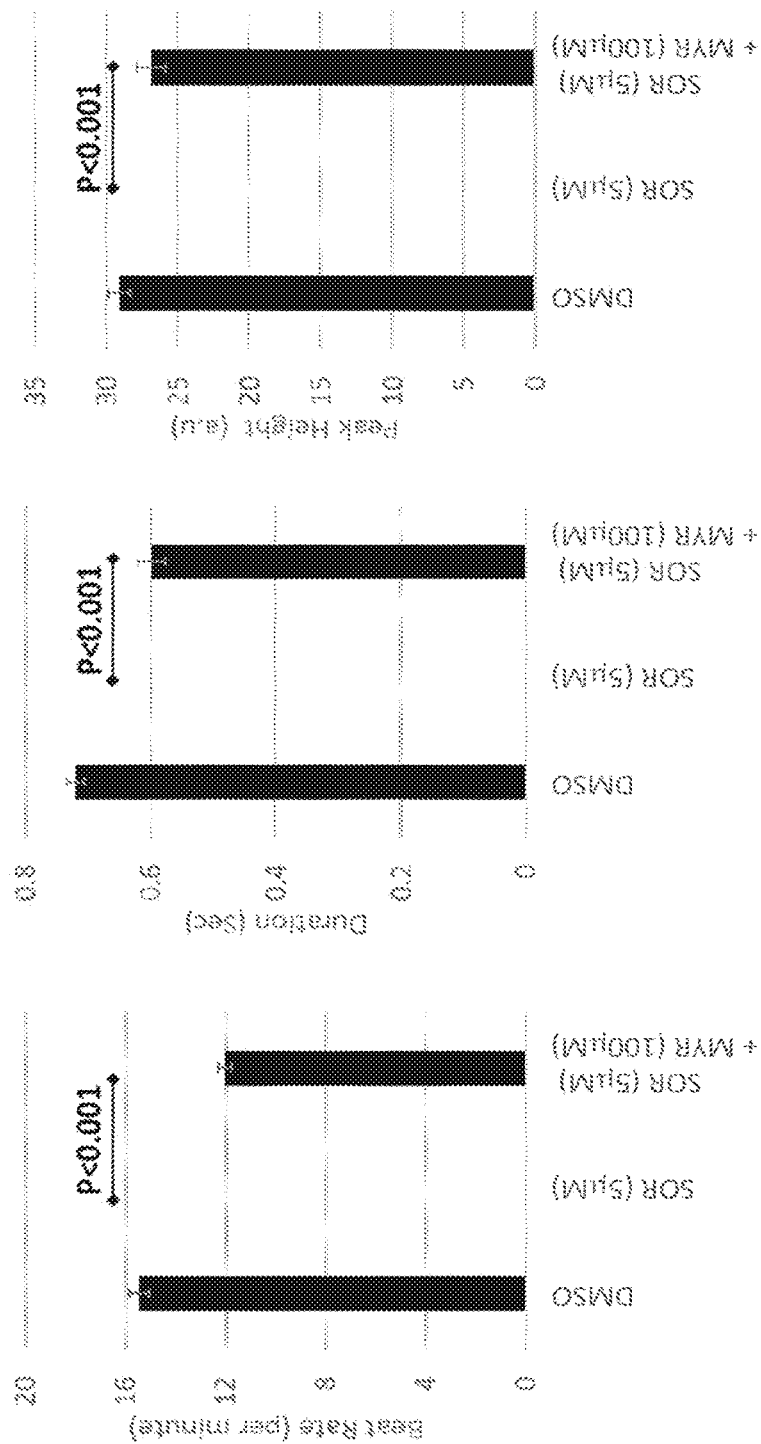
FIG. 21 is a graph illustrating the effect of myricetin (MYR) on sorafenib (SOR)-induced contractile dysfunction.
Figure 22:
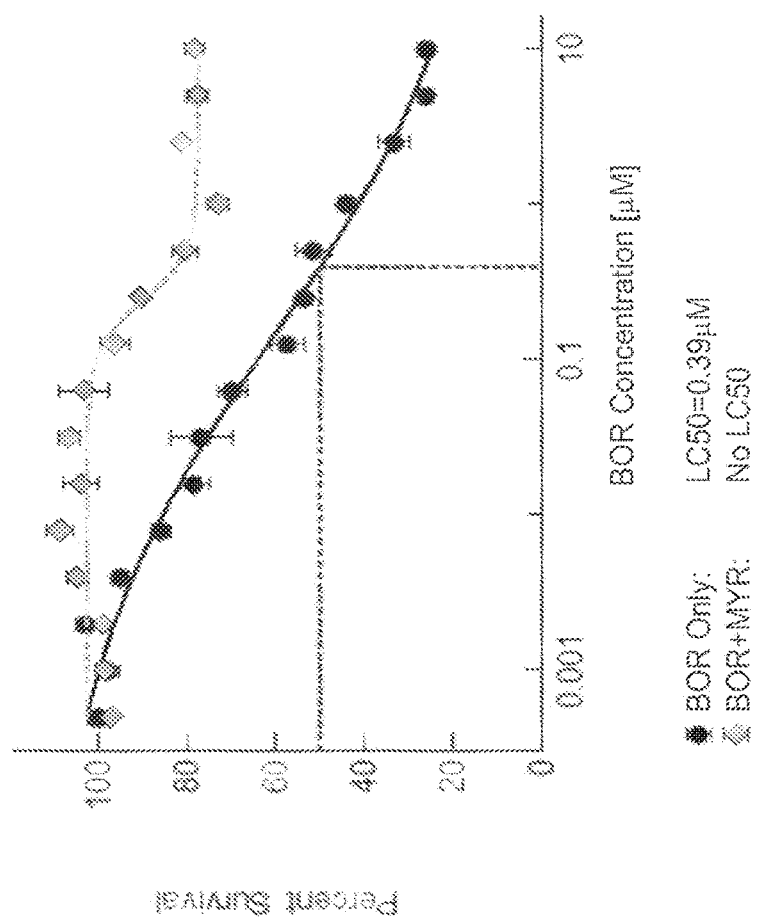
FIG. 22 is a graph illustrating the effect of myricetin (MYR) on bortezomib (BOR)-induced cell death.

Cell samples were prepared by differentiating induced pluripotent stem cells into cardiomyocytes. Cells were cultured for 4 days post-differentiation, changing media day 3, before performing experiments. Human stem cell derived cardiomyocytes were then treated DMSO, sunitinib (10 µM) or sunitinib plus increasing concentrations of MYR (1 to 100 µM) for 72 hours, and then incubated with dyes that indicate mitochondrial health and cellular nuclei. Cells were imaged and total number of healthy cells were counted and plotted as percentage of sunitinib-treatment control. MYR displayed protection against sunitinib-induced cell death in cardiomyocytes (FIG. 20). (n=3). Similarly, MYR successfully corrected more than 80% of cardiac dysfunction in 5 µM sorafenib treated cardiomyocytes (FIG. 21). Treatment with 100 µM myricetin also rescued bortezomib-induced cardiotoxicity (FIG. 22). These data suggest that MYR protects against protein kinase inhibitor-induced cardiomyocyte cell death.

Example 15. No Interference with Doxorubicin's Anti-Cancer Activity

Bisdioxopiperazine dexrazoxane (DEX) is the only drug available for reducing the incidence of heart failure in cancer patients receiving anticancer agents. Despite its clinical effect, DEX is associated with several side effects such as interfering with antitumor efficacy of anthracyclines, inducing secondary malignancies, and causing blood and bone marrow disorders. These limitations severely limit its use for certain cancer patients.

Figure 23:
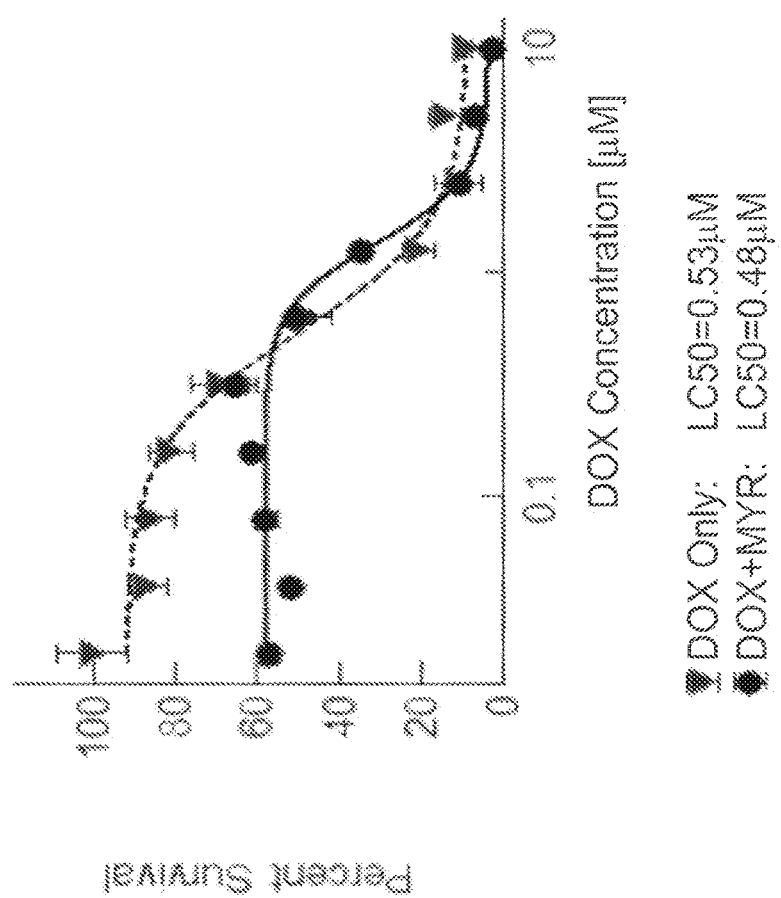
FIG. 23 is a graph illustrating the lack of effect of myricetin (MYR) on DOX's anticancer activity.

The effect, of MYR was investigated to determine whether the compound has the similar shortcomings to those observed in DEX, Breast cancer cells (MDA-MB-231) were mock-treated or treated with 100 µM of MYR and with increasing concentrations of doxorubicin for 72 hours (FIG. 23). Cell viability assay was conducted (CellTiter-Glo, Promega). Luminescence was recorded via Synergy HT (Biotek) microplate reader and plotted as percentage of mock-treated control. Essentially no difference was observed in cell viability (LC50) between mock-treated (0.53 µM) versus MYR-treated (0.48 µM), indicating that MYR does not interfere with doxorubicin's anti-cancer activity (FIG. 23) (n=3).

Example 16. In Vivo Validation of Cardioprotection Against DOX-Induced Toxicity An acute anthracycline-induced cardiotoxicity model was established in 9-10 week old C57BL/6 mice obtained from The Jackson Laboratory. Animals were divided into three groups: saline treated (n=8). Doxorubicin treated (n=16) or Doxorubicin+MYR treated (n=17). Doxorubicin (20 mg/kg), MYR (40 mg/kg) and saline were administered via a single intraperitoneal injection, MYR was administered 30 minutes prior to doxorubicin treatment. General health of the animals was monitored on a daily basis throughout the course of the study. Mice were anesthetized using isoflurane (~1.0%) and transthoracic echocardiography was performed using the VevoLAZR Imaging system (VisualSonics Inc., Toronto, Canada) at day −4 to obtain baseline measurements and then at day 5 following the treatments. Left ventricular (LV) M-mode images were obtained in the two-dimensional short axis view close to the papillary muscles. Tracings of endocardial tissue during systole and diastole were made offline. These data were then used to calculate fractional shortening (FS) and ejection fraction (EF) which are global indices of systolic function.

Figure 24:
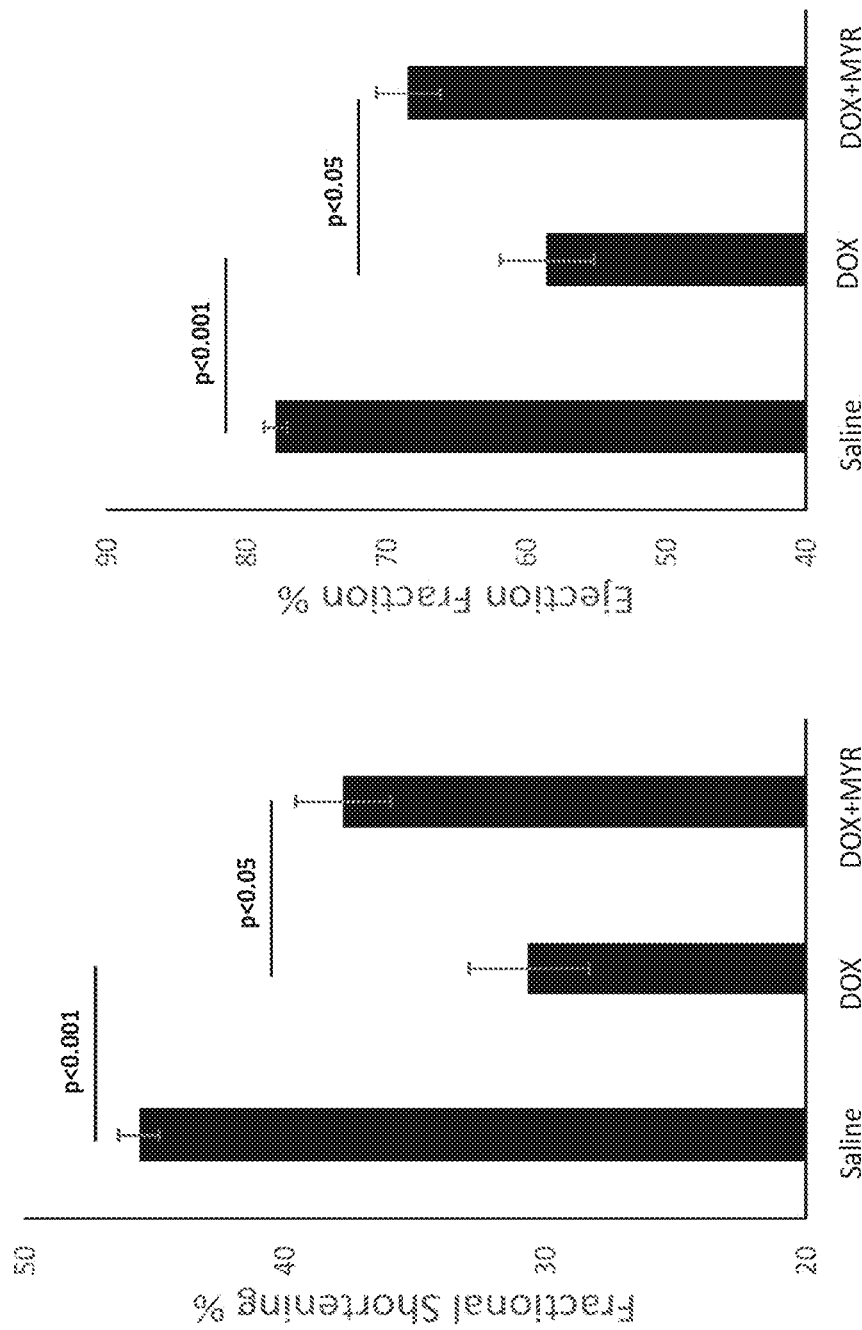
FIG. 24 depicts the effect of MYR on DOX-induced contractile dysfunction in mice measured in percentage of fractional shortening (left) and ejection fraction (right).

Contractile properties were unaltered in the saline group during the course of the study. In contrast, doxorubicin treatment had a profound impact on contractile properties. In this group, FS and EF decreased significantly with time (P<0.001) by 15% and 1.9%, respectively. MYR treatment significantly reduced the doxorubicin-induced cardiotoxicity (P<0.05) as observed by improvement of FS and EF by 7% and 10% respectively (FIG. 24). At 2-fold higher concentration than doxorubicin, MYR elicited 52% rescue of FS and 49% rescue of EF dysfunction caused by doxorubicin (FIG. 24).

Example 17. Effect of Various Protectants (Including Vitexin) on Doxorubicin-Induced Cardiotoxicity Regarding Mitochondrial Toxicity Cell samples were prepared by differentiating induced pluripotent stem cells into cardiomyocytes. Cells were cultured for 4 days post-differentiation, changing media at day 3, before performing experiments. Samples were either mock treated, treated with 1 µM of doxorubicin, or treated with 1 µM of doxorubicin and the indicated drug for 48 hours. Following treatment, the samples were incubated with a tetramethylrhodamine methyl ester (TMRM) dye to indicate mitochondrial health, and a second dye to identify cell nuclei. Cells were imaged using the INCell Analyzer2200, and images were analyzed by CeliProfiler to quantity the percentage of TMRM-negative cells. Representative data are presented for protective agents from two independent sets of screens where each data point was obtained from three biological replicates. Data normalization was performed by re-calibrating data based on the mock-treated sample (0% mitochondrial toxicity) and the 1 µM doxorubicin-treated sample (100% mitochondrial toxicity).

Figure 25:
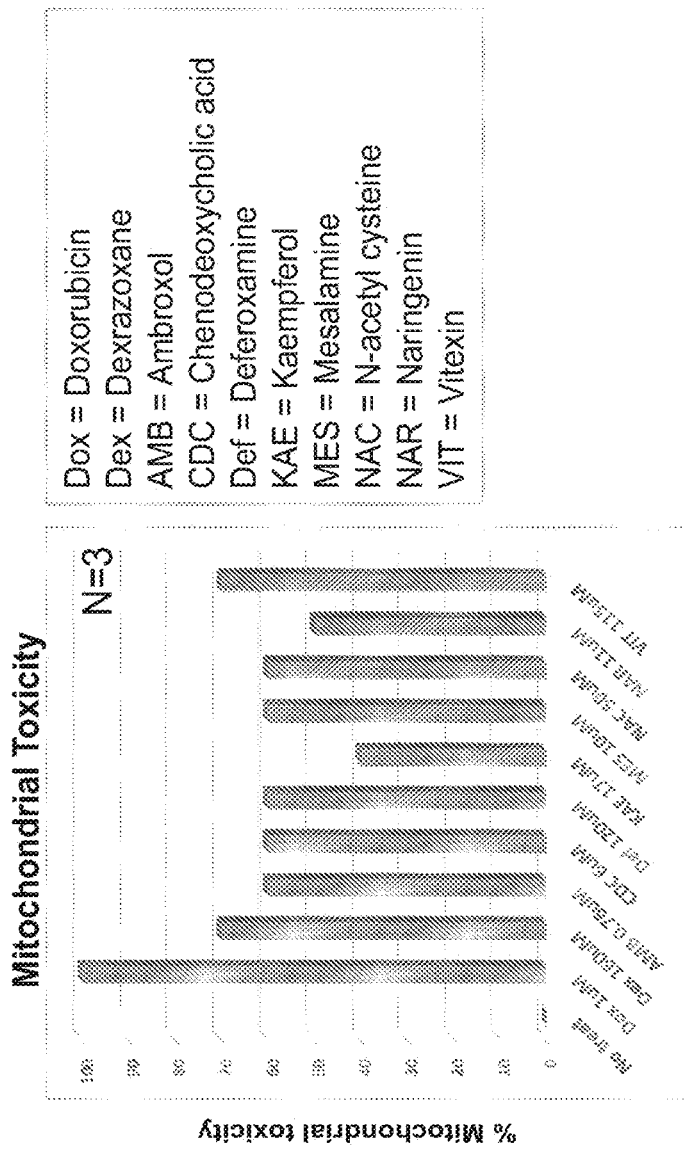
FIG. 25 depicts the effects of DOX DEX, and various protective agents on mitochondrial toxicity in cardiomyocytes derived from human induced pluripotent stem cells.

Cardiomyocytes were either mock-treated ('No treat'), treated with 1 µM doxorubicin ('Dox 1 µM'), or treated with 1 µM doxorubicin and the indicated drug, and subsequently stained to detect mitochondrial health (FIG. 25). Cardiomyocytes exposed to 17 µM kaempferol ('KAE 17 µM') exhibited a decrease in mitochondrial toxicity of at least 60%, as compared to cardiomyocytes treated with doxorubicin in the absence of a protective agent ('Dox 1 µM'). Cardiomyocytes exposed to either 0.76 µM ambroxol ('AMB 0.76 µM'), 10 µM mesalamine ('MES 10 µM'), or 50 µM N-acetyl cysteine ('NAC 50 µM') exhibited a decrease in mitochondrial toxicity of at least 40%, as compared to cardiomyocytes treated with doxorubicin in the absence of a protective agent ('Dox 1 µM'). Cardiomyocytes exposed to either 160 µM dexrazoxane ('Dex 160 µM') or 115 µM vitexin ('VIT 115 µM') exhibited a decrease in mitochondrial toxicity of at least 30%, as compared to cardiomyocytes treated with doxorubicin in the absence of a protective agent ('Dox 1 µM').

Example 18. Effect of Various Protectants (Including Vitexin) on Doxorubicin-Induced Cardiotoxicity (Apoptosis)

Cell samples were prepared by differentiating induced pluripotent stem ceils into cardiomyocytes. Cells were cultured for 4 days post-differentiation, changing media day 3, before performing experiments. Samples were either mock-treated, treated with 1 µM of doxorubicin, or treated with 1 µM of doxorubicin and the indicated drug for 48 hours. Following treatment, the samples were incubated with a TUNEL dye to indicate apoptosis-positive cells, and a second dye to identity cell nuclei. Cells were imaged using the INCell Analyzer2200, and images were analyzed by Cell Profiler to quantify the percentage of apoptosis-positive cells. Representative data are presented for protective agents from two independent sets of screens where each data point was obtained from three biological replicates. Data normalization was performed by re-calibrating data based on the mock-treated sample (0% apoptosis) and the 1 micromolar doxorubicin-treated sample (100% apoptosis).

Figure 26:
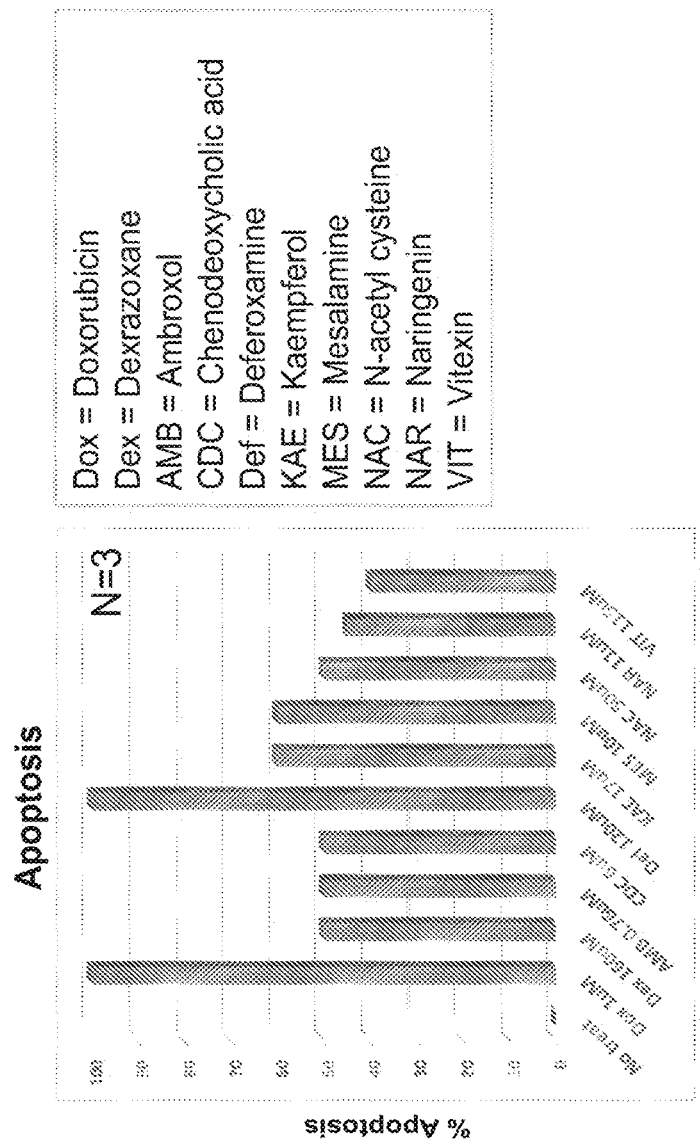
FIG. 26 depicts the effects of DOX, DEX, and various protective agents on apoptosis in cardiomyocytes derived from human induced pluripotent stem cells.

Cardiomyocytes were either mock treated ('No treat'), treated with 1 µM doxorubicin ('Dox 1 µM'), or co-treated with 1 µM doxorubicin and the indicated drug, and subsequently stained to detect apoptosis (FIG. 26). Cardiomyocytes treated with 115 µM vitexin ('VIT 115 µM') exhibited a decrease in apoptosis of at least 60%, as compared to cardiomyocytes treated with doxorubicin in the absence of a protective agent ('Dox 1 µM'). Cardiomyocytes exposed to either 160 µM dexrazoxane ('Dex 160 µM'). 0.76 µM ambroxol ('AMB 0.76 µM'), or 50 µM N-acetyl cysteine ('NAC 50 µM') exhibited a decrease in apoptosis of at least 50%, as compared to cardiomyocytes treated with doxorubicin in the absence of a protective agent ('Dox 1 µM'). Cardiomyocytes exposed to either 17 µM kaempferol ('KAE 17 µM') or 10 µM mesalamine ('MES 10 µM') exhibited a decrease in apoptosis of at least 40%, as compared to cardiomyocytes treated with doxorubicin in the absence of a protective agent (' Dox 1 µM').

Example 19. Vitexin Provides Long-Term Cardioprotection (Mitochondrial Health)

Cell samples were prepared by differentiating induced pluripotent stem cells into cardiomyocytes. Cells were cultured for 4 days post-differentiation, changing media at day 3, before performing experiments. Samples were either mock-treated (FIG. 27A), treated with 1 µM of doxorubicin (FIG. 27B), co-treated with 1 µM of doxorubicin and 16 µM dexrazoxane (FIG. 27C), or co-treated with 1 µM of doxorubicin and 116 µM dexrazoxane (FIG. 27D) for 7 days. Following treatment, the samples were incubated with a tetramethylrhodamine methyl ester (TMRM) dye to indicate mitochondrial health. Cells were imaged using the INCell Analyzer2200, and images were analyzed by CellProfiler to quantify the percentage of TMRM-negative cells. Representative images are presented for each sample, wherein loss of TMRM signal represents mitochondrial toxicity.

Cardiomyocytes exposed to either doxorubicin (FIG. 27B) or co-treated with doxorubicin and dexrazoxane (FIG. 27C) exhibited an increase in mitochondrial toxicity as indicated by a noticeable decrease in TMRM-positive cells as compared to mock-treated cardiomyocytes (FIG. 27A). Treatment of cardiomyocytes with doxorubicin and vitexin (FIG. 27D) demonstrated improved long term mitochondrial protection, as compared to cardiomyocytes exposed to either doxorubicin (FIG. 27B) or doxorubicin and dexrazoxane (FIG. 27C).

Example 20. Vitexin Provides Dose-Dependent Cardioprotection (Electrophysiological Activity)

Figure 28B:
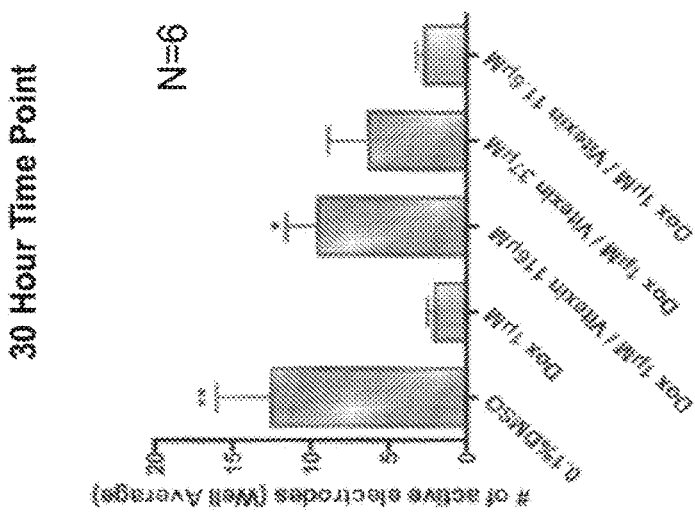
FIG. 28A-B depict the effects of DOX, or co-administration of DOX with various concentrations of vitexin (VIT) on the electrophysiological activity in human induced pluripotent stem cell-derived cardiomyocytes over a three-day time period (left), or at a 30-hour time point (right)
Figure 28A:
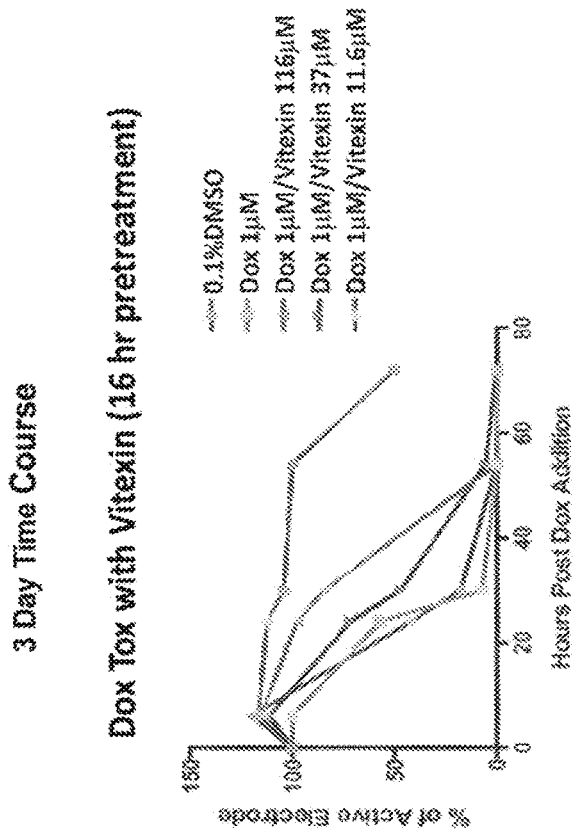

Cell samples were prepared by differentiating induced pluripotent stem cells into cardiomyocytes. Cells were cultured for 4 days post-differentiation, changing media at day 3, before performing experiments. Samples were either mock-treated with 0.1% DMSO, treated with 1 µM doxorubicin, or co-treated with 1 LIM doxorubicin and various concentrations of vitexin (e.g., 11.6 µM, 37 µM, or 116 µM). Following treatment, the percentage of active electrodes in each sample was measured for 72 hours. Percentage of active electrodes was quantified and graphed in a time course (FIG. 28A). The average number of active electrodes per well was quantified and graphed at 30 hours after the treatment (FIG. 28B, n=6, standard deviation is shown as error bars).

Cardiomyocytes exposed to 1 µM doxorubicin, in the absence of vitexin, exhibited about a 50% decrease in the number of active electrodes 24 hours after drug treatment (time zero), and about a 95% decrease, relative to time zero, in the number of active electrodes 30 hours after drug treatment (FIG. 28A). Cardiomyocytes co-exposed to doxorubicin and vitexin exhibited a dose-dependent increase in the percentage of active electrodes (FIG. 28A). At 24 hours following drug treatment, cardiomyocytes co-exposed to 1 µM doxorubicin and either 11.6 µM, 37 µM, or 116 µM vitexin exhibited about a 50%, about a 25%, or about a 0% decrease in the number of active electrodes, respectively. At 30 hours following treatment, samples that were co-exposed to 1 µM doxorubicin and 116 µM vitexin exhibited had a statistically significant higher average number of active electrodes (about 10 active electrodes) as compared to samples that were exposed to 1 µM doxorubicin in the absence of vitexin (about 2 active electrodes) (FIG. 28B).

Example 21. Protectants do not Inhibit Doxorubicin-Mediated Death of Breast Cancer Cells MDA-MB-231 cells (metastatic breast cancer) were cultured for 1 day before performing experiments. Samples treated with either increasing concentrations of Doxorubicin (e.g., 0 µM, 0.016 µM, 0.05 µM, 0.16 µM, 0.5 µM, 1.6 µM, 5 µM, 16 µM, or 50 µM), or co-treated with increasing concentrations of doxorubicin and the indicated protective agent for 72 hours. Cells were subsequently lysed with CellTiter-Glo reagent to identify metabolically active (e.g., viable) cells, wherein the luminescence measured from the lysed cell suspension is directly proportional to the number of viable cells present in the culture. Percentage cell death was quantified by measuring the decrease in luminescence. XLFit was used for curve fitting. Averages from triplicate are graphed and standard deviation is shown as error bars.

Figure 29A:
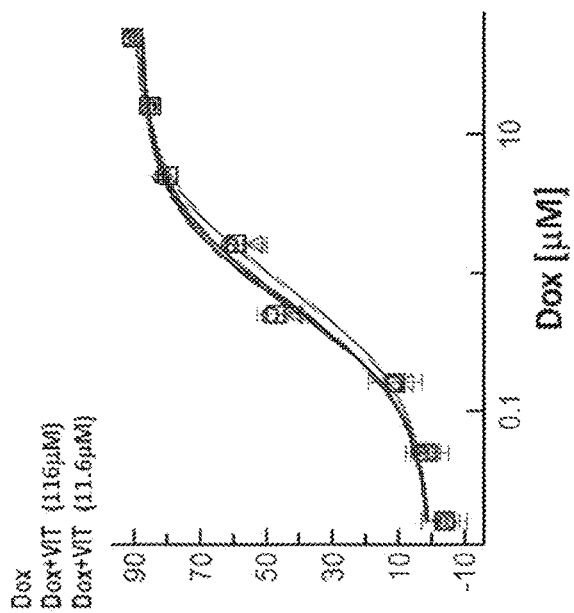
FIG. 29A-B depict the effects of co-administration of doxorubicin with kaempferol (KAE; left) and vitexin (VIT; right) on viability in MDA-MB-231 metastatic breast cancer cells.
Figure 29B:
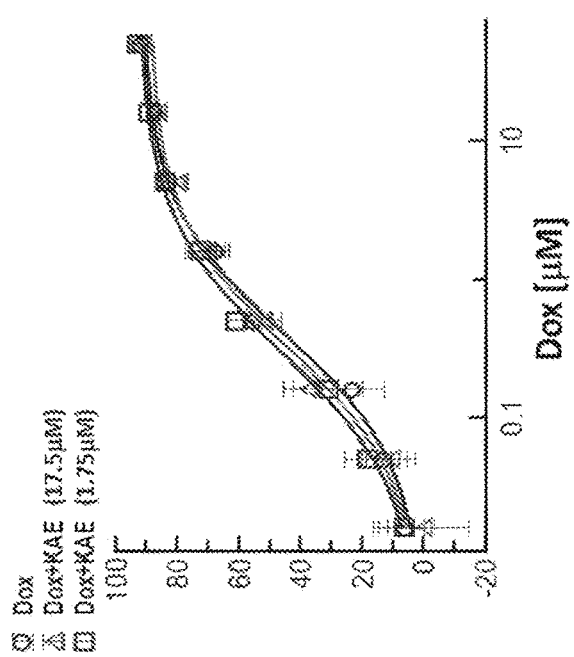

MDA-MB-231 cells co-treated with increasing concentrations of doxorubicin and either dexrazoxane, ambroxol, kaempferol (FIG. 29A), mesalamine, N-acetyl cysteine, or vitexin (FIG. 29B) showed no significant difference in the percentage of cell death as compared to cells that were treated with doxorubicin in the absence of a protective agent. These results indicate that the pharmaceutical compositions described herein do not confer a protective benefit to MDA-MB-231 breast cancer cells, as measured by the in vitro assay.

Example 22. Protectants do not Inhibit Doxorubicin-Mediated Death of Lung Cancer Cells A549 cells (lung cancer) were cultured for 1 day before performing experiments. Samples treated with either increasing concentrations of Doxorubicin (e.g., 0 µM, 0.016 µM, 0.05 µM, 0.16 µM, 0.5 µM, 1.6 µM, 5 LIM, 16 µM, or 50 µM), or co-treated with increasing concentrations of doxorubicin and the indicated drug for 72 hours. Cells were subsequently lysed with CellTiter-Glo reagent to identify metabolically active (e.g., viable) cells, wherein the luminescence measured from the lysed cell suspension is directly proportional to the number of viable cells present in the culture. Percentage cell death was quantified by measuring the decrease in luminescence. XLFit was used for curve fitting. Averages from triplicate are graphed and standard deviation is shown as error bars.

A549 cells co-treated with increasing concentrations of doxorubicin and either dexrazoxane, ambroxol, kaempferol, mesalamine, N-acetyl cysteine, or vitexin showed no significant difference in the percentage of cell death as compared to cells that that were treated with doxorubicin in the absence of a protective agent. These results indicate that the pharmaceutical compositions described herein do not confer a protective benefit to A549 lung cancer cells, as measured by the in vitro assay.

Example 23. Acute Toxicity of Various Protectants (Including Vitexin) on Electrophysiology Cell samples were prepared by differentiating induced pluripotent stem cells into cardiomyocytes. Cells were cultured for 4 days post-differentiation, changing media at 3 day, before performing experiments. Samples were either mock-treated with 0.1% DMSO, or treated with increasing concentrations of the indicated drug for at least 20 minutes. Cardiomyocytes were treated with the hERG potassium channel blocker E4031 as a control. Following treatment, the beat period and field potential duration (FPD) were measured in each sample using the MEA.

At lower drug concentration, Cardiomyocytes exposed to either dexrazoxane, ambroxol, chenodeoxycholic acid, deferoxamine, N-acetyl cysteine, naringenin, or vitexin exhibited no appreciable difference in beat period or field potential duration, as compared to control samples. At higher concentrations, cardiomyocytes exposed to either chenodeoxycholic acid or naringenin exhibited beating cessation from acute drug toxicity.

Example 24. Long Term Toxicity of Various Protectants (Including Vitexin) on Electrophysiology Cell samples were prepared by differentiating induced pluripotent stem cells into cardiomyocytes. Cells were cultured for 4 days post-differentiation, changing media at day 3, before performing experiments. Samples were either mock-treated with 0.1% DMSO, or treated with various concentrations of the indicated drug. Following treatment, the percentage of active electrodes in each sample was measured for at least 5 days. Percentage of active electrodes was quantified and graphed in a time course.

Cardiomyocytes exposed to either ambroxol, kaempferol, mesalamine, or vitexin showed no observable decrease in the number of active electrodes relative to the mock-treated sample. Cardiomyocytes exposed to the clinically-approved cardioprotectant dexrazoxane exhibited a long-term, dose-dependent cardiotoxic effect. Cardiomyocytes exposed to either 167 µM or 500 µM dexrazoxane exhibited about a 25% or 50% reduction in the number of active electrodes at about 2 days post-treatment, respectively. At about 3 days post-treatment, cardiomyocytes exposed to either 167 µM or 500 µM dexrazoxane exhibited about a 50% or 100% reduction in the number of active electrodes, respectively.

Example 25. Treatment of Breast Cancer in a Patient with Heart Disease by Oral Administration of a Pill Containing Doxorubicin and Vitexin A patient, with a history of heart disease, is diagnosed with breast cancer. Due to an increased risk for heart failure, the patient is unable to receive the standard treatment regimen of doxorubicin, which is known to induce cardiotoxicity. Instead, the caregiver administers a co-formulation of doxorubicin (10 mg) and vitexin (100 mg). An echocardiogram is performed and blood flow rate is measured to determine if the therapy has a cardiotoxic effect in the patient. The patient shows no indication of cardiac dysfunction. Exhibiting no signs of cardiotoxicity, the patient is able accept higher doses of treatment over the next several weeks. The patient subsequently undergoes a tissue biopsy which shows no indication of breast cancer.

Example 26. Treatment of Liver Cancer Las a Patient by Intravenous Administration of Doxorubicin, Dexrazoxane and Vitexin A patient is diagnosed with, liver cancer. The caregiver administers to the patient a co-formulation of doxorubicin (5 mg/mL) and dexrazoxane (50 mg/mL). An electrocardiogram is performed to determine if the dexrazoxane is successfully mitigating cardiotoxic effects in the patient. The patient presents with a 20 ms QT prolongation. To enhance the activity of dexrazoxane, the caregiver administers to the patient a co-formulation of doxorubicin (5 mg/mL) and vitexin (100 mg/mL). Following treatment, an electrocardiogram is performed, and the patient exhibits no signs of QT prolongation. The patient is able to continue receiving treatment over several weeks after which a tissue biopsy is performed to confirm the liver cancer has been eradicated.

Example 27. Treatment of Lung Cancer in a Patient with Bradycardia by Oral Administration of a Pill Containing Doxorubicin and Myricetin A patient is diagnosed with stage II lung cancer, and presents with bradycardia. Due to an increased risk for heart failure, the patient is unable to receive the standard treatment regimen of doxorubicin, which is known to affect cardiac contraction and induce bradycardia. Instead, the caregiver administers a co-formulation of doxorubicin (10 mg) and myricetin (100 mg). An electrocardiogram is used to monitor the patient's heart rate. The patient shows no indication of cardiac dysfunction. Exhibiting no signs of cardiotoxicity, the patient is able accept higher doses of treatment over the next several weeks. The lung cancer is down-staged to stage 1, and the cancer is successfully removed with surgery. Upon follow-up, a tissue biopsy is performed and shows no sign of cancer.

Example 28. Treatment of Liver Cancer in a Patient by Intravenous Administration of a Solution Containing Doxorubicin, Dexrazoxane and Myricetin A patient is diagnosed with liver cancer. The caregiver administers to the patient a co-formulation of doxorubicin (5 mg/mL) and dexrazoxane (50 mg/mL). An electrocardiogram, is performed to determine if the dexrazoxane is successfully mitigating cardiotoxic effects in the patient. The patient presents with a 20 ms QT prolongation. To enhance the activity of dexrazoxane, the caregiver administers to the patient a co-formulation of doxorubicin (5 mg/mL) and myricetrin (50 mg/mL). Following treatment, an electrocardiogram is performed, and the patient exhibits no signs of QT prolongation. The patient is able to continue receiving treatment over several weeks after which a tissue biopsy is performed to confirm the liver cancer has been eradicated.

Example 29. Treatment of Lung Cancer in a Patient with Bradycardia by Oral Administration of a Pill Containing Myricetin A patient is diagnosed with stage II lung cancer, and presents with bradycardia. Due to an increased risk for heart failure, the patient is unable to receive the standard treatment regimen of doxorubicin, which is known to affect cardiac contraction and induce bradycardia. Instead, the caregiver administers myricetin (100 mg) 24 hours before administration of doxorubicin (10 mg). An electrocardiogram is used to monitor the patient's heart rate. The patient shows no indication of cardiac dysfunction. Exhibiting no signs of cardiotoxicity, the patient is able accept higher doses of treatment over the next several weeks. The lung cancer is down-staged to stage 1, and the cancer is successfully removed with surgery. Upon follow-up, a tissue biopsy is performed and shows no sign of cancer.

Example 30. Treatment of Liver Cancer in a Patient by Intravenous Administration of a Solution Containing Doxorubicin, Dexrazoxane and Myricetin A patient is diagnosed with liver cancer. The caregiver administers to the patient a co-formulation of doxorubicin (5 mg/mL) and dexrazoxane (50 mg/mL). An electrocardiogram is performed to determine if the dexrazoxane is successfully mitigating cardiotoxic effects in the patient. The patient presents with a 20 ms QT prolongation. To enhance the activity of dexrazoxane, the caregiver administers to the patient a myricetin (100 mg) 2.4 hours prior to administration of doxorubicin (5 mg/mL) and (100 mg/mL) intravenously. Following treatment, an electrocardiogram is performed, and the patient exhibits no signs of QT prolongation. The patient is able to continue receiving treatment over several weeks after which a tissue biopsy is performed to confirm the liver cancer has been eradicated.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A method for preventing, reducing, or eliminating cardiotoxicity induced by an anthracycline or salt thereof in a subject, the method comprising administering to the subject an effective amount of a protective agent prior to or simultaneously with the anthracycline or salt thereof, wherein the administration of the protective agent provides an effective amount of myricetin in the subject, thereby preventing, reducing, or eliminating the cardiotoxicity induced by the anthracycline or salt thereof in the subject.

2. The method of claim 1, wherein the protective agent is myricetin or derivative thereof.

3. The method of claim 1, wherein the protective agent is administered intravenously.

4. The method of claim 1, wherein the subject suffers from cancer.

5. The method of claim 1, further comprising administering an effective amount of a second protective agent prior to or simultaneously with the anthracycline or salt thereof.

6. The method of claim 5, wherein the second protective agent is dexrazoxane or derivative thereof.

7. The method of claim 1, wherein the anthracycline is selected from the group consisting of doxorubicin, daunorubicin, epirubicin, idarubicin, mitoxantrone, and valrubicin.

8. The method of claim 1, wherein the protective agent is administered to the subject at least about 5 minutes before the administration of the anthracycline or salt thereof.

9. The method of claim 1, wherein the protective agent and the anthracycline or salt thereof are administered simultaneously.

10. The method of claim 9, wherein the protective agent and the anthracycline or salt thereof are co-formulated in a liquid composition.

11. The method of claim 1, wherein the cardiotoxicity comprises one or more of cardiac tissue damage, electrophysiological dysfunction, contractile dysfunction, mitochondrial toxicity, DNA double strand break in cardiomyocytes, apoptosis, and oxidative stress.

12. The method of claim 11, wherein the electrophysiological dysfunction comprises QT prolongation or QTc prolongation, and/or wherein the contractile dysfunction comprises reduced ejection fraction (EF) or reduced fractional shortening (FS).

13. The method of claim 1, wherein the subject has a decreased QTc interval after administering the protective agent.

14. A method of treating cancer in a subject without inducing cardiotoxicity or with reduced cardiotoxicity, comprising administering to the subject an effective amount of an anthracycline or salt thereof, wherein the subject has an effective amount of myricetin, thereby preventing, reducing, or eliminating the cardiotoxicity induced by the anthracycline or salt thereof in the subject.

15. The method of claim 14, wherein the method further comprises administering to the subject an effective amount of myricetin or derivative thereof prior to the administration of the anthracycline or salt thereof.

16. The method of claim 15, wherein the effective amount of myricetin or derivative thereof is administered to the subject at least about 5 minutes prior to the administration of the anthracycline or salt thereof.

17. The method of claim 14, wherein the anthracycline is selected from the group consisting of doxorubicin, daunorubicin, epirubicin, idarubicin, mitoxantrone, and valrubicin.

18. The method of claim 14, wherein the cardiotoxicity comprises one or more of cardiac tissue damage, electrophysiological dysfunction, contractile dysfunction, mitochondrial toxicity, DNA double strand break in cardiomyocytes, apoptosis, and oxidative stress.

19. The method of claim 18, wherein the electrophysiological dysfunction comprises QT prolongation or QTc prolongation, and/or wherein the contractile dysfunction comprises reduced ejection fraction (EF) or reduced fractional shortening (FS).

* * * * *